United States Patent [19]
Kappler et al.

[11] Patent Number: 5,820,866
[45] Date of Patent: Oct. 13, 1998

[54] PRODUCT AND PROCESS FOR T CELL REGULATION

[75] Inventors: John W. Kappler; Philippa Marrack, both of Denver, Colo.

[73] Assignee: National Jewish Center for Immunology and Respiratory Medicine, Denver, Colo.

[21] Appl. No.: 207,481

[22] Filed: Mar. 4, 1994

[51] Int. Cl.$^6$ .......................... A61K 39/385; C07K 14/74
[52] U.S. Cl. ..................................... 424/192.1; 424/185.1; 424/193.1; 435/69.7; 435/69.8; 530/395; 530/403; 536/23.4; 536/23.5
[58] Field of Search ............................. 424/185.1, 193.1, 424/192.1; 530/300, 328, 350, 395, 868, 403; 435/69.7, 69.8, 69.3; 536/23.5, 23.4

[56] References Cited

U.S. PATENT DOCUMENTS

| | | | |
|---|---|---|---|
| 4,400,376 | 8/1983 | Sanderson | 424/88 |
| 4,478,823 | 10/1984 | Sanderson | 424/88 |
| 5,130,297 | 7/1992 | Sharma et al. | 514/8 |
| 5,194,425 | 3/1993 | Sharma et al. | 514/8 |
| 5,260,422 | 11/1993 | Clark et al. | 530/403 |
| 5,284,935 | 2/1994 | Clark et al. | 530/403 |

FOREIGN PATENT DOCUMENTS

| | | | |
|---|---|---|---|
| 0 665 289 A2 | 8/1995 | European Pat. Off. | C12N 9/88 |
| WO 93/09810 | 5/1993 | WIPO . | |
| 95/11702 | 5/1995 | WIPO | A61K 39/385 |
| 95/23814 | 9/1995 | WIPO | C07K 19/00 |
| 96/04314 | 2/1996 | WIPO | C07K 19/00 |
| 96/17939 | 6/1996 | WIPO | C12N 15/38 |

OTHER PUBLICATIONS

Chen, Y. et al., J. Immunology 152:2874–81, "Naturally-processed peptides longer than nine amino acid residues bind to the Class I MHC molecule HLA–A2.1 with high affinity and in different conformations", 1994.

Kang, X. et al., Cancer Res. 57:202–205, "Induction of melanoma reactive T cells by stimulator cells expressing melanoma epitope–major histocompatibility complex Class I Fusion proteins", Jan. 15, 1997.

Kozono, H. et al., Nature 369:151–154, "Production of soluble MHC Class I proteins with covalently–bound single peptides", May 12, 1994.

Mottez, E. et al., J. Exp. Med. 181:493–502, "Cells expressing a major histocompatibility complex Class I molecule with a single covalently–bound peptide are highly immunogenic", Feb. 1995.

Urban, R. G. et al., P.N.A.S. (USA) 91:1534–1538, "A subset of HLA–B27 molecules contains peptides much longer than nonamers", Feb. 1994.

Brown et al., "Three–Dimensional Structure of the Human Class II Histocompatibility Antigen HLA–DR1", pp. 33–39, 1993, *Nature*, vol. 364, Jul.

*Primary Examiner*—Thomas M. Cunningham
*Attorney, Agent, or Firm*—Sheridan Ross P.C.

[57] ABSTRACT

The present invention relates to a product and process for regulating the activity of T cells using major histocompatibility complexes (MHC) stably linked to antigenic peptides. Disclosed is an antigenic peptide covalently linked to a major histocompatibility complex (MHC) protein by a novel linker, thereby enabling the formation of a stable peptide-MHC complex, alone or in combination with additional MHC protein chains, capable of being recognized by a T cell receptor (TCR). Also disclosed is a nucleic molecule having a sequence encoding a Peptide-L-MHC molecule comprising an antigenic peptide joined by a linker to an MHC segment. The invention is additionally directed to formulations comprising an antigenic peptide joined by a linker to an MHC segment anchored in a lipid-containing substrate. Pharmaceutical reagents are also disclosed which contain an antigenic peptide joined by a linker to an MHC segment combined with a suitable carrier that is capable of presenting the Peptide-L-MHC molecule so that it is capable of being recognized by a T cell receptor.

57 Claims, 12 Drawing Sheets

Transfected Cells Express IA$^b$ Bound to the E$_\alpha$ Peptide
FIG. 4A – B10.A(5R) Spleen Cells
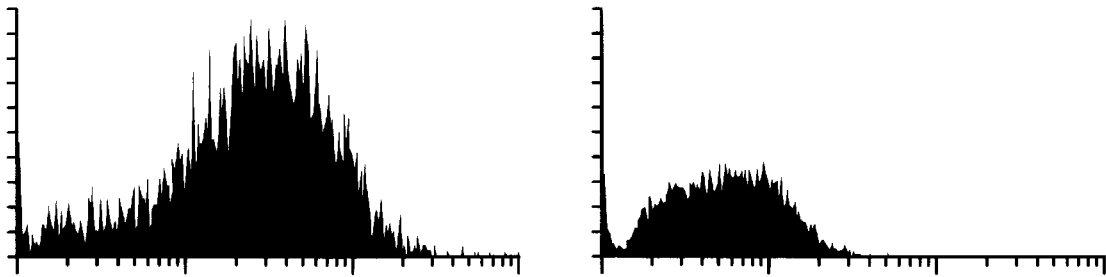
FIG. 4B – Transfected M12.C3 Lymphoma B cells
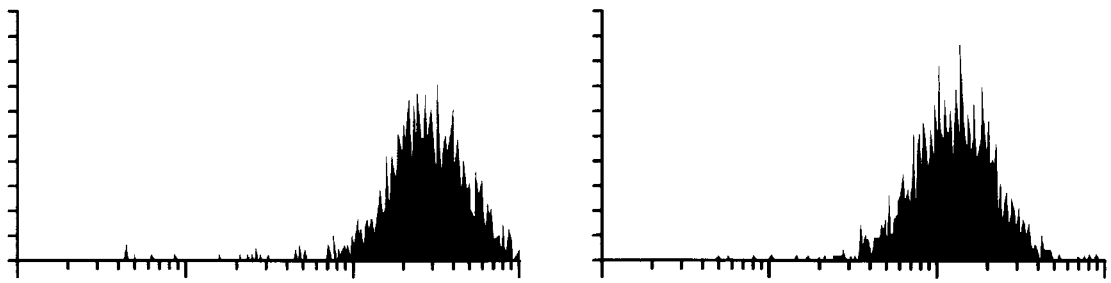
FIG. 4C – Untransfected M12.C3 Lymphoma B cells
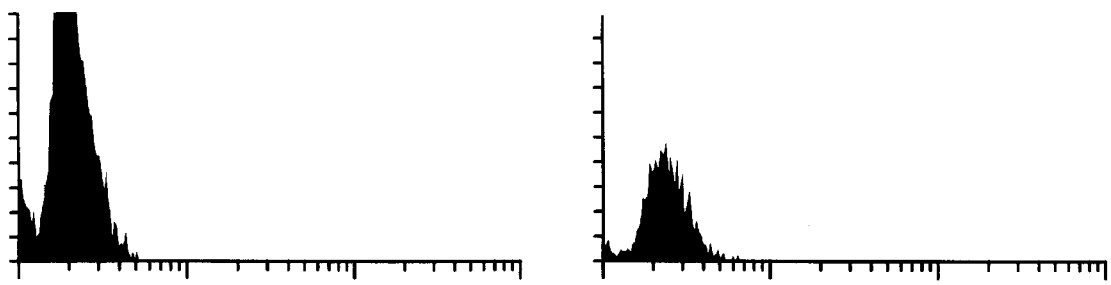
Staining With
Anti-IA$^b$
Staining With
Anti-IA$^b$-E$_\alpha$ Peptide Fibroblasts Transfected With the Genes for IA$^b$ and E$\alpha$ Peptide React With Antibodies to the Complex
FIG. 7A – No Antibody
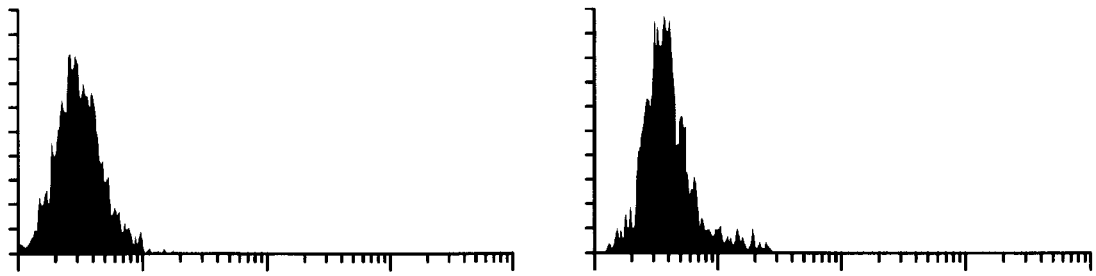
FIG. 7B – Anti-IA$^b$
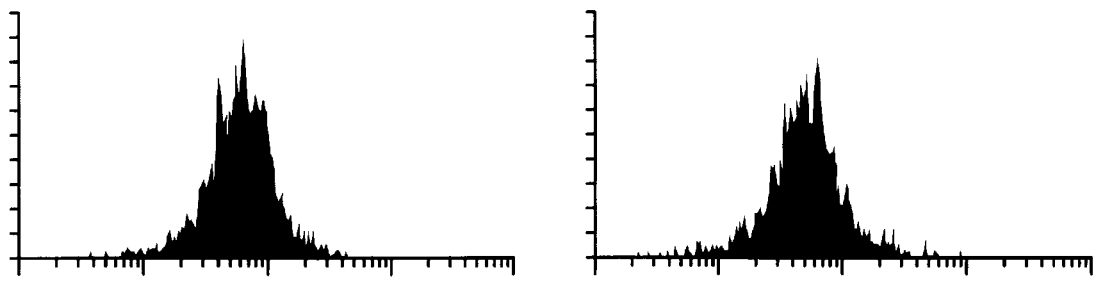
FIG. 7C – Anti-IA$^b$-E$_\alpha$ Peptide
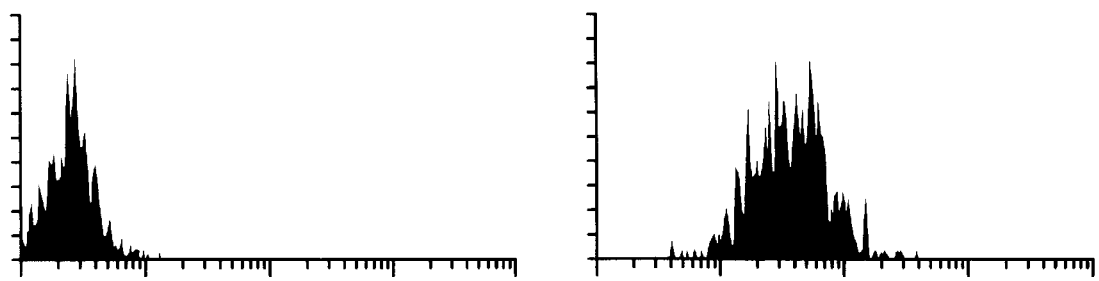
Fibroblasts Bearing IA$^b$
Fibroblasts Bearing IA$^b$-E$\alpha$ Peptide

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Arg  Ala  Asp  Leu  Ile  Ala  Tyr  Leu  Lys  Gln  Ala  Thr  Lys
1                   5                        10
```

(2) INFORMATION FOR SEQ ID NO:2:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Val  His  Ala  Ala  His  Ala  Glu  Ile  Asn  Glu  Ala  Gly  Arg
1                   5                        10
```

(2) INFORMATION FOR SEQ ID NO:3:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Arg  Ala  Asp  Leu  Ile  Ala  Tyr  Leu  Lys  Gln  Ala  Thr  Lys
1                   5                        10
```

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Val  His  Ala  Ala  His  Ala  Glu  Ile  Asn  Glu  Ala  Gly  Arg
1                   5                        10
```

(2) INFORMATION FOR SEQ ID NO:5:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Ala  Ser  Phe  Glu  Ala  Gln  Gly  Ala  Leu  Ala  Asn  Ile  Ala  Val  Asp  Lys
1                   5                        10                            15
Ala
```

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:6:

Gly Gly Gly Gly Ser Leu Val Pro Arg Gly Ser Gly Gly Gly Gly Ser
1               5                   10                  15

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Gly Gly Gly Gly Ser Gly Gly Gly Gly Ser
1               5                   10

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Leu Val Pro Arg Gly Ser
1               5

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

TCCTCGAGAA ATGGCCACAA TTGGAG                        26

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

TTGGTACCTT AATTCTCTTT AGTTTC                       26

( 2 ) INFORMATION FOR SEQ ID NO:11:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

CCGGGAATTC AGCATGGTGT GGCTCC    26

( 2 ) INFORMATION FOR SEQ ID NO:12:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:12:

CCGCATGCTT ACGTTGTTCT TGCAGA    26

( 2 ) INFORMATION FOR SEQ ID NO:13:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:13:

TCCTCGAGAG GATGCCGTGC AGCAGAG    27

( 2 ) INFORMATION FOR SEQ ID NO:14:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:14:

TTGGTACCTT AAGTTTCTGG TCAGCTC    27

( 2 ) INFORMATION FOR SEQ ID NO:15:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:15:

TACGGAATTC TTAGAGATGG CTCTGCAGA    29

( 2 ) INFORMATION FOR SEQ ID NO:16:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:16:

CCGCATGCTT ACTTGCTCCG GGCAGACT    28

( 2 ) INFORMATION FOR SEQ ID NO:17:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:17:

TACGGAATTC AGCATGGTGT GGCTCCC                27

( 2 ) INFORMATION FOR SEQ ID NO:18:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:18:

ACCGGACGAA GTTTATCCGT TAGTCCAGTC GGGCCCTCAG AGACTGGTT            49

( 2 ) INFORMATION FOR SEQ ID NO:19:

( i ) SEQUENCE CHARACTERISTICS:
    ( A ) LENGTH: 887 base pairs
    ( B ) TYPE: nucleic acid
    ( C ) STRANDEDNESS: single
    ( D ) TOPOLOGY: linear ( i i ) MOLECULE TYPE: DNA ( i x ) FEATURE:
    ( A ) NAME/KEY: CDS
    ( B ) LOCATION: 58..819

( x i ) SEQUENCE DESCRIPTION: SEQ ID NO:19:

```
TTTTACTGTT TTCGTAACAG TTTTGTAATA AAAAAACCTA TAAATACGGA ATTCAGC                57

ATG GTG TGG CTC CCC AGA GTT CCC TGT GTG GCA GCT GTG ATC CTG TTG            105
Met Val Trp Leu Pro Arg Val Pro Cys Val Ala Ala Val Ile Leu Leu
 1               5                  10                  15

CTG ACA GTG CTG AGC CCT CCA GTG GCT TTG GTC AGA GAC TCC CGG GCT            153
Leu Thr Val Leu Ser Pro Pro Val Ala Leu Val Arg Asp Ser Arg Ala
             20                  25                  30

GAC CTG ATT GCC TAT TTG AAG CAG GCC ACC AAG GGA GGT GGT GGC TCA            201
Asp Leu Ile Ala Tyr Leu Lys Gln Ala Thr Lys Gly Gly Gly Gly Ser
                 35                  40                  45

CTA GTG CCA CGG GGC TCT GGA GGA GGT GGG TCC AGA CCA TGG TTT TTG            249
Leu Val Pro Arg Gly Ser Gly Gly Gly Gly Ser Arg Pro Trp Phe Leu
     50                  55                  60

GAA TAC TGT AAA TCT GAG TGT CAT TTC TAC AAC GGG ACG CAG CGC GTA            297
Glu Tyr Cys Lys Ser Glu Cys His Phe Tyr Asn Gly Thr Gln Arg Val
 65                  70                  75                  80

CGG CTT CTG GTA AGA TAC TTC TAC AAC CTC GAG GAG AAC CTG CGC TTC            345
Arg Leu Leu Val Arg Tyr Phe Tyr Asn Leu Glu Glu Asn Leu Arg Phe
                 85                  90                  95

GAC AGC GAC GTG GGC GAG TTC CGC GCG GTG ACC GAG CTG GGT CGA CCA            393
Asp Ser Asp Val Gly Glu Phe Arg Ala Val Thr Glu Leu Gly Arg Pro
                100                 105                 110

GAC GCC GAG AAC TGG AAC AGC AGC CGG GAG TTC CTG GAG CAA AAG CGG            441
Asp Ala Glu Asn Trp Asn Ser Gln Pro Glu Phe Leu Glu Gln Lys Arg
            115                 120                 125

GCC GAG GTG GAC ACG GTG TGC AGA CAC AAC TAT GAG ATC TTC GAT AAC            489
```

| Ala | Glu | Val | Asp | Thr | Val | Cys | Arg | His | Asn | Tyr | Glu | Ile | Phe | Asp | Asn |
| | | | | 130 | | | | 135 | | | | 140 | | | |

| TTC | CTT | GTG | CCG | CGG | AGA | GTT | GAG | CCT | ACG | GTG | ACT | GTG | TAC | CCC | ACA | 537 |
| Phe | Leu | Val | Pro | Arg | Arg | Val | Glu | Pro | Thr | Val | Thr | Val | Tyr | Pro | Thr | |
| 145 | | | | | 150 | | | | 155 | | | | | | 160 | |

| AAG | ACG | CAG | CCC | CTG | GAA | CAC | CAC | AAC | CTC | CTG | GTC | TGC | TCT | GTG | AGT | 585 |
| Lys | Thr | Gln | Pro | Leu | Glu | His | His | Asn | Leu | Leu | Val | Cys | Ser | Val | Ser | |
| | | | | 165 | | | | 170 | | | | | | 175 | | |

| GAC | TTC | TAC | CCT | GGC | AAC | ATT | GAA | GTC | AGA | TGG | TTC | CGG | AAT | GGC | AAG | 633 |
| Asp | Phe | Tyr | Pro | Gly | Asn | Ile | Glu | Val | Arg | Trp | Phe | Arg | Asn | Gly | Lys | |
| | | | 180 | | | | | 185 | | | | | 190 | | | |

| GAG | GAG | AAA | ACA | GGA | ATT | GTG | TCC | ACG | GGC | CTG | GTC | CGA | AAT | GGA | GAC | 681 |
| Glu | Glu | Lys | Thr | Gly | Ile | Val | Ser | Thr | Gly | Leu | Val | Arg | Asn | Gly | Asp | |
| | | 195 | | | | | 200 | | | | | 205 | | | | |

| TGG | ACC | TTC | CAG | ACA | CTG | GTG | ATG | CTG | GAG | ACG | GTT | CCT | CAG | AGT | GGA | 729 |
| Trp | Thr | Phe | Gln | Thr | Leu | Val | Met | Leu | Glu | Thr | Val | Pro | Gln | Ser | Gly | |
| 210 | | | | | | 215 | | | | 220 | | | | | | |

| GAG | GTT | TAC | ACC | TGC | CAG | GTG | GAG | CAT | CCC | AGC | CTG | ACC | GAC | CCT | GTC | 777 |
| Glu | Val | Tyr | Thr | Cys | Gln | Val | Glu | His | Pro | Ser | Leu | Thr | Asp | Pro | Val | |
| 225 | | | | | 230 | | | | | 235 | | | | | 240 | |

| ACG | GTC | GAG | TGG | AAA | GCA | CAG | TCC | ACA | TCT | GCA | CAG | AAC | AAG | | | 819 |
| Thr | Val | Glu | Trp | Lys | Ala | Gln | Ser | Thr | Ser | Ala | Gln | Asn | Lys | | | |
| | | | | 245 | | | | | 250 | | | | | | | |

TAAGCATGCG GGGATCCGGT TATTAGTACA TTTATTAAGC GCTAGATTCT GTGCGTTGTT    879

GATTTACA    887

( 2 ) INFORMATION FOR SEQ ID NO:20:

( i ) SEQUENCE CHARACTERISTICS:
        ( A ) LENGTH: 254 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

| Met | Val | Trp | Leu | Pro | Arg | Val | Pro | Cys | Val | Ala | Ala | Val | Ile | Leu | Leu |
| 1 | | | | 5 | | | | 10 | | | | | | 15 | |

| Leu | Thr | Val | Leu | Ser | Pro | Pro | Val | Ala | Leu | Val | Arg | Asp | Ser | Arg | Ala |
| | | | 20 | | | | 25 | | | | | 30 | | | |

| Asp | Leu | Ile | Ala | Tyr | Leu | Lys | Gln | Ala | Thr | Lys | Gly | Gly | Gly | Gly | Ser |
| | | | 35 | | | | 40 | | | | | 45 | | | |

| Leu | Val | Pro | Arg | Gly | Ser | Gly | Gly | Gly | Ser | Arg | Pro | Trp | Phe | Leu |
| | | 50 | | | | 55 | | | | | 60 | | | | |

| Glu | Tyr | Cys | Lys | Ser | Glu | Cys | His | Phe | Tyr | Asn | Gly | Thr | Gln | Arg | Val |
| 65 | | | | 70 | | | | 75 | | | | | | 80 | |

| Arg | Leu | Leu | Val | Arg | Tyr | Phe | Tyr | Asn | Leu | Glu | Glu | Asn | Leu | Arg | Phe |
| | | | | 85 | | | | 90 | | | | | 95 | | |

| Asp | Ser | Asp | Val | Gly | Glu | Phe | Arg | Ala | Val | Thr | Glu | Leu | Gly | Arg | Pro |
| | | | 100 | | | | 105 | | | | | 110 | | | |

| Asp | Ala | Glu | Asn | Trp | Asn | Ser | Gln | Pro | Glu | Phe | Leu | Glu | Gln | Lys | Arg |
| | | 115 | | | | | 120 | | | | | 125 | | | |

| Ala | Glu | Val | Asp | Thr | Val | Cys | Arg | His | Asn | Tyr | Glu | Ile | Phe | Asp | Asn |
| | | 130 | | | | | 135 | | | | | 140 | | | |

| Phe | Leu | Val | Pro | Arg | Arg | Val | Glu | Pro | Thr | Val | Thr | Val | Tyr | Pro | Thr |
| 145 | | | | | 150 | | | | 155 | | | | | | 160 |

| Lys | Thr | Gln | Pro | Leu | Glu | His | His | Asn | Leu | Leu | Val | Cys | Ser | Val | Ser |
| | | | | 165 | | | | 170 | | | | | | 175 | |

```
Asp Phe Tyr Pro Gly Asn Ile Glu Val Arg Trp Phe Arg Asn Gly Lys
            180                 185                 190

Glu Glu Lys Thr Gly Ile Val Ser Thr Gly Leu Val Arg Asn Gly Asp
            195                 200                 205

Trp Thr Phe Gln Thr Leu Val Met Leu Glu Thr Val Pro Gln Ser Gly
    210                 215                 220

Glu Val Tyr Thr Cys Gln Val Glu His Pro Ser Leu Thr Asp Pro Val
225                 230                 235                 240

Thr Val Glu Trp Lys Ala Gln Ser Thr Ser Ala Gln Asn Lys
            245                 250
```

( 2 ) INFORMATION FOR SEQ ID NO:21:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

```
GGGGCACCGT GATCACTCGG TGGTGGAGGG AACCACCGGA CGAAGTTTAT          50
```

( 2 ) INFORMATION FOR SEQ ID NO:22:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

```
TTTTGGTAC CAGACCTGGG TGGAGGAGGT CTCGGGGCAC CGTGATCACT CG        52
```

( 2 ) INFORMATION FOR SEQ ID NO:23:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

```
TACGGAATTC TTAGAGATGG CTCTGCAGAT                                30
```

( 2 ) INFORMATION FOR SEQ ID NO:24:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

```
AGAGTCGTAC CCGTCGTACA TGCCTCAAAG GCGGGAGTCA GGGCCCCGAC GAGT      54
```

( 2 ) INFORMATION FOR SEQ ID NO:25:

( i ) SEQUENCE CHARACTERISTICS:
        ( A ) LENGTH: 893 base pairs (B) TYPE: nucleic acid
(C) STRANDEDNESS: single
(D) TOPOLOGY: linear (ii) MOLECULE TYPE: DNA (ix) FEATURE:
    (A) NAME/KEY: CDS
    (B) LOCATION: 61..825

(xi) SEQUENCE DESCRIPTION: SEQ ID NO:25:

```
TTTTACTGTT TTCGTAACAG TTTTGTAATA AAAAAACCTA TAAATACGGA ATTCTTAGAG                60

ATG GCT CTG CAG ATC CCC AGC CTC CTC CTC TCA GCT GCT GTG GTG GTG               108
Met Ala Leu Gln Ile Pro Ser Leu Leu Leu Ser Ala Ala Val Val Val
 1               5                  10                  15

CTG ATG GTG CTG AGC AGC CCC GGG ACT GAG GGC GGA AAC TCC GTA CAT               156
Leu Met Val Leu Ser Ser Pro Gly Thr Glu Gly Gly Asn Ser Val His
             20                  25                  30

GCT GCC CAT GCT GAG ATC AAT GAG GCT GGC AGA GGA GGT GGG GGC TCA               204
Ala Ala His Ala Glu Ile Asn Glu Ala Gly Arg Gly Gly Gly Gly Ser
         35                  40                  45

CTA GTG CCC CGA GGC TCT GGA GGT GGA GGC TCC GAA AGG CAT TTC GTG               252
Leu Val Pro Arg Gly Ser Gly Gly Gly Gly Ser Glu Arg His Phe Val
     50                  55                  60

GTC CAG TTC AAG GGC GAG TGC TAC TAC ACC AAC GGG ACG CAG CGC ATA               300
Val Gln Phe Lys Gly Glu Cys Tyr Tyr Thr Asn Gly Thr Gln Arg Ile
 65                  70                  75                  80

CGG CTC GTG ACC AGA TAC ATC TAC AAC CGG GAG GAG TAC GTG CGC TAC               348
Arg Leu Val Thr Arg Tyr Ile Tyr Asn Arg Glu Glu Tyr Val Arg Tyr
                 85                  90                  95

GAC AGC GAC GTG GGC GAG TAC CGC GCG GTG ACC GAG CTG GGG CGG CCA               396
Asp Ser Asp Val Gly Glu Tyr Arg Ala Val Thr Glu Leu Gly Arg Pro
            100                 105                 110

GAC GCC GAG TAC TGG AAC AGC CAG CCG GAG ATC CTG GAG CGA ACG CGG               444
Asp Ala Glu Tyr Trp Asn Ser Gln Pro Glu Ile Leu Glu Arg Thr Arg
        115                 120                 125

GCC GAG GTG GAC ACG GCG TGC AGA CAC AAC TAC GAG GGG CCG GAG ACC               492
Ala Glu Val Asp Thr Ala Cys Arg His Asn Tyr Glu Gly Pro Glu Thr
    130                 135                 140

AGC ACC TCC CTG CGG CGG CTT GAA CAG CCC AAT GTC GCC ATC TCC CTG               540
Ser Thr Ser Leu Arg Arg Leu Glu Gln Pro Asn Val Ala Ile Ser Leu
145                 150                 155                 160

TCC AGG ACA GAG GCC CTC AAC CAC CAC AAC ACT CTG GTC TGT TCG GTG               588
Ser Arg Thr Glu Ala Leu Asn His His Asn Thr Leu Val Cys Ser Val
                165                 170                 175

ACA GAT TTC TAC CCA GCC AAG ATC AAA GTG CGC TGG TTC AGG AAT GGC               636
Thr Asp Phe Tyr Pro Ala Lys Ile Lys Val Arg Trp Phe Arg Asn Gly
            180                 185                 190

CAG GAG GAG ACA GTG GGG GTC TCA TCC ACA CAG CTT ATT AGG AAT GGG               684
Gln Glu Glu Thr Val Gly Val Ser Ser Thr Gln Leu Ile Arg Asn Gly
        195                 200                 205

GAC TGG ACC TTC CAG GTC CTG GTC ATG CTG GAG ATG ACC CCT CAT CAG               732
Asp Trp Thr Phe Gln Val Leu Val Met Leu Glu Met Thr Pro His Gln
    210                 215                 220

GGA GAG GTC TAC ACC TGC CAT GTG GAG CAT CCC AGC CTG AAG AGC CCC               780
Gly Glu Val Tyr Thr Cys His Val Glu His Pro Ser Leu Lys Ser Pro
225                 230                 235                 240

ATC ACT GTG GAG TGG AGG GCA CAG TCC GAG TCT GCC CGG AGC AAG                   825
Ile Thr Val Glu Trp Arg Ala Gln Ser Glu Ser Ala Arg Ser Lys
                245                 250                 255

TAAGCATGCG GGGATCCGGT TATTAGTACA TTTATTAAGC GCTAGATTCT GTGCGTTGTT             885
```

GATTTACA                                                                                                            893

( 2 ) INFORMATION FOR SEQ ID NO:26:

( i ) SEQUENCE CHARACTERISTICS:
        ( A ) LENGTH: 255 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Met Ala Leu Gln Ile Pro Ser Leu Leu Leu Ser Ala Ala Val Val Val
  1               5                  10                  15
Leu Met Val Leu Ser Ser Pro Gly Thr Glu Gly Gly Asn Ser Val His
             20                  25                  30
Ala Ala His Ala Glu Ile Asn Glu Ala Gly Arg Gly Gly Gly Gly Ser
             35                  40                  45
Leu Val Pro Arg Gly Ser Gly Gly Gly Ser Glu Arg His Phe Val
         50                  55                  60
Val Gln Phe Lys Gly Glu Cys Tyr Tyr Thr Asn Gly Thr Gln Arg Ile
 65                  70                  75                  80
Arg Leu Val Thr Arg Tyr Ile Tyr Asn Arg Glu Glu Tyr Val Arg Tyr
                 85                  90                  95
Asp Ser Asp Val Gly Glu Tyr Arg Ala Val Thr Glu Leu Gly Arg Pro
                100                 105                 110
Asp Ala Glu Tyr Trp Asn Ser Gln Pro Glu Ile Leu Glu Arg Thr Arg
                115                 120                 125
Ala Glu Val Asp Thr Ala Cys Arg His Asn Tyr Glu Gly Pro Glu Thr
            130                 135                 140
Ser Thr Ser Leu Arg Arg Leu Glu Gln Pro Asn Val Ala Ile Ser Leu
145                 150                 155                 160
Ser Arg Thr Glu Ala Leu Asn His His Asn Thr Leu Val Cys Ser Val
                    165                 170                 175
Thr Asp Phe Tyr Pro Ala Lys Ile Lys Val Arg Trp Phe Arg Asn Gly
                180                 185                 190
Gln Glu Glu Thr Val Gly Val Ser Ser Thr Gln Leu Ile Arg Asn Gly
                195                 200                 205
Asp Trp Thr Phe Gln Val Leu Val Met Leu Glu Met Thr Pro His Gln
    210                 215                 220
Gly Glu Val Tyr Thr Cys His Val Glu His Pro Ser Leu Lys Ser Pro
225                 230                 235                 240
Ile Thr Val Glu Trp Arg Ala Gln Ser Glu Ser Ala Arg Ser Lys
                245                 250                 255
```

( 2 ) INFORMATION FOR SEQ ID NO:27:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

CCGTGATCAC TCGGGGGTGG AGGAGACGGT CGGAGTAACT AGAGTCGTAC CCGTC                     55

( 2 ) INFORMATION FOR SEQ ID NO:28:

( i ) SEQUENCE CHARACTERISTICS:
   ( A ) LENGTH: 51 base pairs
   ( B ) TYPE: nucleic acid
   ( C ) STRANDEDNESS: single
   ( D ) TOPOLOGY: linear ( i i ) MOLECULE TYPE: DNA ( x i ) SEQUENCE DESCRIPTION: SEQ ID NO:28:

GGCTCACTAG TGCCCCGAGG CTCTGGAGGT GGAGGCTCCG AAAGGCATTT C    51

( 2 ) INFORMATION FOR SEQ ID NO:29:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:29:

GGCGTACGAA CGAATGAACG AGGCCCGTCT GAG    33

( 2 ) INFORMATION FOR SEQ ID NO:30:

( i ) SEQUENCE CHARACTERISTICS:
      ( A ) LENGTH: 420 base pairs
      ( B ) TYPE: nucleic acid
      ( C ) STRANDEDNESS: single
      ( D ) TOPOLOGY: linear ( i i ) MOLECULE TYPE: DNA ( i x ) FEATURE:
      ( A ) NAME/KEY: CDS
      ( B ) LOCATION: 58..420

( x i ) SEQUENCE DESCRIPTION: SEQ ID NO:30:

TTTTACTGTT TTCGTAACAG TTTTGTAATA AAAAAACCTA TAAATACGGA ATTCAGC    57

```
ATG  GTG  TGG  CTC  CCC  AGA  GTT  CCC  TGT  GTG  GCA  GCT  GTG  ATC  CTG  TTG    105
Met  Val  Trp  Leu  Pro  Arg  Val  Pro  Cys  Val  Ala  Ala  Val  Ile  Leu  Leu
 1              5                        10                       15

CTG  ACA  GTG  CTG  AGC  CCT  CCA  GTG  GCT  TTG  GTC  AGA  GAC  TCC  AGA  CCA    153
Leu  Thr  Val  Leu  Ser  Pro  Pro  Val  Ala  Leu  Val  Arg  Asp  Ser  Arg  Pro
               20                       25                       30

TGG  TTT  TTG  GAA  TAC  TTT  TAC  TGT  TTT  CGT  AAC  AGT  TTT  GTA  ATA  AAA    201
Trp  Phe  Leu  Glu  Tyr  Phe  Tyr  Cys  Phe  Arg  Asn  Ser  Phe  Val  Ile  Lys
          35                       40                       45

AAA  CCT  ATA  AAT  ACG  GAA  TTC  AGC  ATG  GTG  TGG  CTC  CCC  AGA  GTT  CCC    249
Lys  Pro  Ile  Asn  Thr  Glu  Phe  Ser  Met  Val  Trp  Leu  Pro  Arg  Val  Pro
     50                       55                       60

TGT  GTG  GCA  GCT  GTG  ATC  CTG  TTG  CTG  ACA  GTG  CTG  AGC  CCT  CCA  GTG    297
Cys  Val  Ala  Ala  Val  Ile  Leu  Leu  Leu  Thr  Val  Leu  Ser  Pro  Pro  Val
 65                       70                       75                       80

GCT  TTG  GTC  AGA  GAC  TCC  CGG  GCT  GAC  CTG  ATT  GCC  TAT  TTG  AAG  CAG    345
Ala  Leu  Val  Arg  Asp  Ser  Arg  Ala  Asp  Leu  Ile  Ala  Tyr  Leu  Lys  Gln
                    85                       90                       95

GCC  ACC  AAG  GGA  GGT  GGT  GGC  TCA  CTA  GTG  CCA  CGG  GGC  TCT  GGA  GGA    393
Ala  Thr  Lys  Gly  Gly  Gly  Gly  Ser  Leu  Val  Pro  Arg  Gly  Ser  Gly  Gly
               100                      105                      110

GGT  GGG  TCC  AGA  CCA  TGG  TTT  TTG  GAA                                        420
Gly  Gly  Ser  Arg  Pro  Trp  Phe  Leu  Glu
               115                      120
```

( 2 ) INFORMATION FOR SEQ ID NO:31:

(i) SEQUENCE CHARACTERISTICS:
  (A) LENGTH: 121 amino acids
  (B) TYPE: amino acid
  (D) TOPOLOGY: linear (ii) MOLECULE TYPE: protein (xi) SEQUENCE DESCRIPTION: SEQ ID NO:31:

| Met | Val | Trp | Leu | Pro | Arg | Val | Pro | Cys | Val | Ala | Ala | Val | Ile | Leu | Leu |
|---|---|---|---|---|---|---|---|---|---|---|---|---|---|---|---|
| 1 | | | | 5 | | | | | 10 | | | | | 15 | |

| Leu | Thr | Val | Leu | Ser | Pro | Pro | Val | Ala | Leu | Val | Arg | Asp | Ser | Arg | Pro |
|---|---|---|---|---|---|---|---|---|---|---|---|---|---|---|---|
| | | | 20 | | | | | 25 | | | | | 30 | | |

| Trp | Phe | Leu | Glu | Tyr | Phe | Tyr | Cys | Phe | Arg | Asn | Ser | Phe | Val | Ile | Lys |
|---|---|---|---|---|---|---|---|---|---|---|---|---|---|---|---|
| | | | 35 | | | | 40 | | | | | 45 | | | |

| Lys | Pro | Ile | Asn | Thr | Glu | Phe | Ser | Met | Val | Trp | Leu | Pro | Arg | Val | Pro |
|---|---|---|---|---|---|---|---|---|---|---|---|---|---|---|---|
| | 50 | | | | | 55 | | | | | 60 | | | | |

| Cys | Val | Ala | Ala | Val | Ile | Leu | Leu | Thr | Val | Leu | Ser | Pro | Pro | Val |
|---|---|---|---|---|---|---|---|---|---|---|---|---|---|---|
| 65 | | | | | 70 | | | | 75 | | | | | 80 |

| Ala | Leu | Val | Arg | Asp | Ser | Arg | Ala | Asp | Leu | Ile | Ala | Tyr | Leu | Lys | Gln |
|---|---|---|---|---|---|---|---|---|---|---|---|---|---|---|---|
| | | | | | 85 | | | | 90 | | | | | 95 | |

| Ala | Thr | Lys | Gly | Gly | Gly | Gly | Ser | Leu | Val | Pro | Arg | Gly | Ser | Gly | Gly |
|---|---|---|---|---|---|---|---|---|---|---|---|---|---|---|---|
| | | | 100 | | | | | 105 | | | | | 110 | | |

| Gly | Gly | Ser | Arg | Pro | Trp | Phe | Leu | Glu |
|---|---|---|---|---|---|---|---|---|
| | | 115 | | | | | 120 | |

(2) INFORMATION FOR SEQ ID NO:32:

(i) SEQUENCE CHARACTERISTICS:
  (A) LENGTH: 420 base pairs
  (B) TYPE: nucleic acid
  (C) STRANDEDNESS: single
  (D) TOPOLOGY: linear (ii) MOLECULE TYPE: DNA (ix) FEATURE:
  (A) NAME/KEY: CDS
  (B) LOCATION: 61..420

(xi) SEQUENCE DESCRIPTION: SEQ ID NO:32:

```
TTTTACTGTT  TTCGTAACAG  TTTTGTAATA  AAAAAACCTA  TAAATACGGA  ATTCTTAGAG       60

ATG  GCT  CTG  CAG  ATC  CCC  AGC  CTC  CTC  CTC  TCA  GCT  GCT  GTG  GTG  GTG      108
Met  Ala  Leu  Gln  Ile  Pro  Ser  Leu  Leu  Leu  Ser  Ala  Ala  Val  Val  Val
 1              5                        10                       15

CTG  ATG  GTG  CTG  AGC  AGC  CCA  GGG  ACT  GAG  GGC  GGA  AAC  TCC  GAA  AGG      156
Leu  Met  Val  Leu  Ser  Ser  Pro  Gly  Thr  Glu  Gly  Gly  Asn  Ser  Glu  Arg
              20                        25                        30

CAT  TTC  GTG  GTC  TTT  TAC  TGT  TTT  CGT  AAC  AGT  TTT  GTA  ATA  AAA  AAA      204
His  Phe  Val  Val  Phe  Tyr  Cys  Phe  Arg  Asn  Ser  Phe  Val  Ile  Lys  Lys
              35                        40                        45

CCT  ATA  AAT  ACG  GAA  TTC  TTA  GAG  ATG  GCT  CTG  CAG  ATC  CCC  AGC  CTC      252
Pro  Ile  Asn  Thr  Glu  Phe  Leu  Glu  Met  Ala  Leu  Gln  Ile  Pro  Ser  Leu
        50                        55                        60

CTC  CTC  TCA  GCT  GCT  GTG  GTG  GTG  CTG  ATG  GTG  CTG  AGC  AGC  CCC  GGG      300
Leu  Leu  Ser  Ala  Ala  Val  Val  Val  Leu  Met  Val  Leu  Ser  Ser  Pro  Gly
 65                  70                        75                        80

ACT  GAG  GGC  GGA  AAC  TCC  GTA  CAT  GCT  GCC  CAT  GCT  GAG  ATC  AAT  GAG      348
Thr  Glu  Gly  Gly  Asn  Ser  Val  His  Ala  Ala  His  Ala  Glu  Ile  Asn  Glu
              85                        90                        95

GCT  GGC  AGA  GGA  GGT  GGA  GGC  TCA  CTA  GTG  CCC  CGA  GGC  TCT  GGA  GGT      396
Ala  Gly  Arg  Gly  Gly  Gly  Gly  Ser  Leu  Val  Pro  Arg  Gly  Ser  Gly  Gly
              100                       105                       110
```

```
GGA GGC TCC GAA AGG CAT TTC GTG                                                420
Gly Gly Ser Glu Arg His Phe Val
        115                 120
```

(2) INFORMATION FOR SEQ ID NO:33:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:33:

```
Met Ala Leu Gln Ile Pro Ser Leu Leu Ser Ala Ala Val Val Val
 1               5                  10                 15
Leu Met Val Leu Ser Ser Pro Gly Thr Glu Gly Gly Asn Ser Glu Arg
            20                  25                  30
His Phe Val Val Phe Tyr Cys Phe Arg Asn Ser Phe Val Ile Lys Lys
            35                  40                  45
Pro Ile Asn Thr Glu Phe Leu Glu Met Ala Leu Gln Ile Pro Ser Leu
        50                  55                  60
Leu Leu Ser Ala Ala Val Val Val Leu Met Val Leu Ser Ser Pro Gly
 65                 70                  75                 80
Thr Glu Gly Gly Asn Ser Val His Ala Ala His Ala Glu Ile Asn Glu
                85                  90                  95
Ala Gly Arg Gly Gly Gly Gly Ser Leu Val Pro Arg Gly Ser Gly Gly
            100                 105                 110
Gly Gly Ser Glu Arg His Phe Val
            115                 120
```

(2) INFORMATION FOR SEQ ID NO:34:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

```
CACTGATCCT CGAGGGGGTG ACCGGTCCGG AGGGGTACCA ATTCCAG                47
```

(2) INFORMATION FOR SEQ ID NO:35:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

```
AAATACGGAA TTCGGGTCGA CGGAGATCTG GGCATGCGGG GATCCGG                47
```

(2) INFORMATION FOR SEQ ID NO:36:

(i) SEQUENCE CHARACTERISTICS:
        (A) LENGTH: 35 base pairs
        (B) TYPE: nucleic acid
        (C) STRANDEDNESS: single
        (D) TOPOLOGY: linear ( i i ) MOLECULE TYPE: DNA ( x i ) SEQUENCE DESCRIPTION: SEQ ID NO:36:

CCCGAGCTCG GGAATTCTTA GAGATGGCTC TGCAG                                              35

( 2 ) INFORMATION FOR SEQ ID NO:37:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:37:

TTACAACGG TCACGTGGGA CTCGGAGTTT CGATCGAAGC CTCAGAGGCG GG                            52

( 2 ) INFORMATION FOR SEQ ID NO:38:

( i ) SEQUENCE CHARACTERISTICS:
        ( A ) LENGTH: 1013 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 63..956

( x i ) SEQUENCE DESCRIPTION: SEQ ID NO:38:

```
CAGGAAACAG CTATGACCAT GATTACGAAT TTAATACGAC TCACTATAGG GAATTCTTAG              60

AG ATG GCT CTG CAG ATC CCC AGC CTC CTC CTC TCG GCT GCT GTG GTG               107
   Met Ala Leu Gln Ile Pro Ser Leu Leu Leu Ser Ala Ala Val Val
    1               5                  10                  15

GTG CTG ATG GTG CTG AGC AGC CCA GGG ACT GAG GGC GGA GAC TCC GAA              155
Val Leu Met Val Leu Ser Ser Pro Gly Thr Glu Gly Gly Asp Ser Glu
                20                  25                  30

GCT AGC TTT GAG GCT CAG GGT GCA CTG GCC AAC ATT GCT GTC GAC AAG              203
Ala Ser Phe Glu Ala Gln Gly Ala Leu Ala Asn Ile Ala Val Asp Lys
            35                  40                  45

GCT GGA GGT GGT GGA TCC GGT GGA GGG GGA AGT GGA GGT GGA GGG TCT              251
Ala Gly Gly Gly Gly Ser Gly Gly Gly Gly Ser Gly Gly Gly Gly Ser
        50                  55                  60

GAA AGG CAT TTC GTG TAC CAG TTC ATG GGC GAG TGC TAC TTC ACC AAC              299
Glu Arg His Phe Val Tyr Gln Phe Met Gly Glu Cys Tyr Phe Thr Asn
    65                  70                  75

GGG ACG CAG CGC ATA CGA TAT GTG ACC AGA TAC ATC TAC AAC CGG GAG              347
Gly Thr Gln Arg Ile Arg Tyr Val Thr Arg Tyr Ile Tyr Asn Arg Glu
80                  85                  90                  95

GAG TAC GTG CGC TAC GAC AGC GAC GTG GGC GAG CAC CGC GCG GTG ACC              395
Glu Tyr Val Arg Tyr Asp Ser Asp Val Gly Glu His Arg Ala Val Thr
                100                 105                 110

GAG CTG GGG CGG CCA GAC GCC GAG TAC TGG AAC AGC CAG CCG GAG ATC              443
Glu Leu Gly Arg Pro Asp Ala Glu Tyr Trp Asn Ser Gln Pro Glu Ile
            115                 120                 125

CTG GAG CGA ACG CGG GCC GAG GTG GAC ACG GTG TGC AGA CAC AAC TAC              491
Leu Glu Arg Thr Arg Ala Glu Val Asp Thr Val Cys Arg His Asn Tyr
        130                 135                 140

GAG GGG CCG GAG ACC CAC ACC TCC CTG CGG CGG CTT GAA CAG CCC AAT              539
Glu Gly Pro Glu Thr His Thr Ser Leu Arg Arg Leu Glu Gln Pro Asn
    145                 150                 155
```

| | | | | | | | | | | | | | | | |
|---|---|---|---|---|---|---|---|---|---|---|---|---|---|---|---|
| GTC | GTC | ATC | TCC | CTG | TCC | AGG | ACA | GAG | GCC | CTC | AAC | CAC | CAC | AAC | ACT | 587
| Val | Val | Ile | Ser | Leu | Ser | Arg | Thr | Glu | Ala | Leu | Asn | His | His | Asn | Thr |
| 160 | | | | | 165 | | | | | 170 | | | | | 175 |
| CTG | GTC | TGC | TCA | GTG | ACA | GAT | TTC | TAC | CCA | GCC | AAG | ATC | AAA | GTG | CGC | 635
| Leu | Val | Cys | Ser | Val | Thr | Asp | Phe | Tyr | Pro | Ala | Lys | Ile | Lys | Val | Arg |
| | | | | 180 | | | | | 185 | | | | | 190 | |
| TGG | TTC | CGG | AAT | GGC | CAG | GAG | GAG | ACG | GTG | GGG | GTC | TCA | TCC | ACA | CAG | 683
| Trp | Phe | Arg | Asn | Gly | Gln | Glu | Glu | Thr | Val | Gly | Val | Ser | Ser | Thr | Gln |
| | | | 195 | | | | | 200 | | | | | 205 | | |
| CTT | ATT | AGG | AAT | GGG | GAC | TGG | ACC | TTC | CAG | GTC | CTG | GTC | ATG | CTG | GAG | 731
| Leu | Ile | Arg | Asn | Gly | Asp | Trp | Thr | Phe | Gln | Val | Leu | Val | Met | Leu | Glu |
| | | 210 | | | | | 215 | | | | | 220 | | | |
| ATG | ACC | CCT | CGG | CGG | GGA | GAG | GTC | TAC | ACC | TGT | CAC | GTG | GAG | CAT | CCC | 779
| Met | Thr | Pro | Arg | Arg | Gly | Glu | Val | Tyr | Thr | Cys | His | Val | Glu | His | Pro |
| | | 225 | | | | | 230 | | | | | 235 | | | |
| AGC | CTG | AAG | AGC | CCC | ATC | ACT | GTG | GAG | TGG | AGG | GCA | CAG | TCT | GAG | TCT | 827
| Ser | Leu | Lys | Ser | Pro | Ile | Thr | Val | Glu | Trp | Arg | Ala | Gln | Ser | Glu | Ser |
| 240 | | | | | 245 | | | | | 250 | | | | | 255 |
| GCC | TGG | AGC | AAG | ATG | TTG | AGC | GGC | ATC | GGG | GGC | TGC | GTG | CTT | GGG | GTG | 875
| Ala | Trp | Ser | Lys | Met | Leu | Ser | Gly | Ile | Gly | Gly | Cys | Val | Leu | Gly | Val |
| | | | | 260 | | | | | 265 | | | | | 270 | |
| ATC | TTC | CTC | GGG | CTT | GGC | CTT | TTC | ATC | CGT | CAC | AGG | AGT | CAG | AAA | GGA | 923
| Ile | Phe | Leu | Gly | Leu | Gly | Leu | Phe | Ile | Arg | His | Arg | Ser | Gln | Lys | Gly |
| | | | 275 | | | | | 280 | | | | | 285 | | |
| CCT | CGA | GGC | CCT | CCT | CCA | GCA | GGG | CTC | CTG | CAG | TGAGAATTCG | | GAAGCTTGGC | | | 976
| Pro | Arg | Gly | Pro | Pro | Pro | Ala | Gly | Leu | Leu | Gln | | | | | |
| | | 290 | | | | | 295 | | | | | | | | |

ACTGGCCGTC GTTTTACAAC GTCGTGACTG GGAAAAC       1013

(2) INFORMATION FOR SEQ ID NO:39:

(i) SEQUENCE CHARACTERISTICS:
        (A) LENGTH: 298 amino acids
        (B) TYPE: amino acid
        (D) TOPOLOGY: linear (ii) MOLECULE TYPE: protein (xi) SEQUENCE DESCRIPTION: SEQ ID NO:39:

| | | | | | | | | | | | | | | |
|---|---|---|---|---|---|---|---|---|---|---|---|---|---|---|
| Met | Ala | Leu | Gln | Ile | Pro | Ser | Leu | Leu | Leu | Ser | Ala | Ala | Val | Val |
| 1 | | | | 5 | | | | | 10 | | | | | 15 |
| Leu | Met | Val | Leu | Ser | Ser | Pro | Gly | Thr | Glu | Gly | Gly | Asp | Ser | Glu | Ala |
| | | | 20 | | | | 25 | | | | | 30 | | |
| Ser | Phe | Glu | Ala | Gln | Gly | Ala | Leu | Ala | Asn | Ile | Ala | Val | Asp | Lys | Ala |
| | | | 35 | | | | | 40 | | | | | 45 | | |
| Gly | Gly | Gly | Gly | Ser | Gly | Gly | Gly | Gly | Ser | Gly | Gly | Gly | Gly | Ser | Glu |
| | 50 | | | | | 55 | | | | | 60 | | | | |
| Arg | His | Phe | Val | Tyr | Gln | Phe | Met | Gly | Glu | Cys | Tyr | Phe | Thr | Asn | Gly |
| 65 | | | | | 70 | | | | | 75 | | | | | 80 |
| Thr | Gln | Arg | Ile | Arg | Tyr | Val | Thr | Arg | Tyr | Ile | Tyr | Asn | Arg | Glu | Glu |
| | | | | 85 | | | | | 90 | | | | | 95 | |
| Tyr | Val | Arg | Tyr | Asp | Ser | Asp | Val | Gly | Glu | His | Arg | Ala | Val | Thr | Glu |
| | | | | 100 | | | | | 105 | | | | | 110 | |
| Leu | Gly | Arg | Pro | Asp | Ala | Glu | Tyr | Trp | Asn | Ser | Gln | Pro | Glu | Ile | Leu |
| | | | 115 | | | | | 120 | | | | | 125 | | |
| Glu | Arg | Thr | Arg | Ala | Glu | Val | Asp | Thr | Val | Cys | Arg | His | Asn | Tyr | Glu |
| | | 130 | | | | | 135 | | | | | 140 | | | |
| Gly | Pro | Glu | Thr | His | Thr | Ser | Leu | Arg | Arg | Leu | Glu | Gln | Pro | Asn | Val |
| 145 | | | | | 150 | | | | | 155 | | | | | 160 |

| Val | Ile | Ser | Leu | Ser | Arg | Thr | Glu | Ala | Leu | Asn | His | His | Asn | Thr | Leu |
|---|---|---|---|---|---|---|---|---|---|---|---|---|---|---|---|
| | | | | 165 | | | | | 170 | | | | | 175 | |
| Val | Cys | Ser | Val | Thr | Asp | Phe | Tyr | Pro | Ala | Lys | Ile | Lys | Val | Arg | Trp |
| | | | 180 | | | | | 185 | | | | | 190 | | |
| Phe | Arg | Asn | Gly | Gln | Glu | Glu | Thr | Val | Gly | Val | Ser | Ser | Thr | Gln | Leu |
| | | 195 | | | | | 200 | | | | | 205 | | | |
| Ile | Arg | Asn | Gly | Asp | Trp | Thr | Phe | Gln | Val | Leu | Val | Met | Leu | Glu | Met |
| | | 210 | | | | 215 | | | | | 220 | | | | |
| Thr | Pro | Arg | Arg | Gly | Glu | Val | Tyr | Thr | Cys | His | Val | Glu | His | Pro | Ser |
| 225 | | | | | 230 | | | | 235 | | | | | | 240 |
| Leu | Lys | Ser | Pro | Ile | Thr | Val | Glu | Trp | Arg | Ala | Gln | Ser | Glu | Ser | Ala |
| | | | | 245 | | | | | 250 | | | | | 255 | |
| Trp | Ser | Lys | Met | Leu | Ser | Gly | Ile | Gly | Gly | Cys | Val | Leu | Gly | Val | Ile |
| | | | 260 | | | | | 265 | | | | | 270 | | |
| Phe | Leu | Gly | Leu | Gly | Leu | Phe | Ile | Arg | His | Arg | Ser | Gln | Lys | Gly | Pro |
| | | 275 | | | | | 280 | | | | | 285 | | | |
| Arg | Gly | Pro | Pro | Pro | Ala | Gly | Leu | Leu | Gln | | | | | | |
| | 290 | | | | | 295 | | | | | | | | | |

( 2 ) INFORMATION FOR SEQ ID NO:40:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

GGTGGCCTAG GTGGTGGAGG TCGGAACAGC TGTCGTTACA ACCGGTCACG    50

( 2 ) INFORMATION FOR SEQ ID NO:41:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

GGTGGATCCG GTGGAGGGGG AAGTGGAGGT GGAGGGTCTG AAAGGCATTT CGTG    54

( 2 ) INFORMATION FOR SEQ ID NO:42:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

CGGTTCGAAG GCTTAAGAGT GACGTCCTCG GGACG    35

( 2 ) INFORMATION FOR SEQ ID NO:43:

( i ) SEQUENCE CHARACTERISTICS:
        ( A ) LENGTH: 143 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
    ( A ) NAME/KEY: CDS
    ( B ) LOCATION: 15..143

( x i ) SEQUENCE DESCRIPTION: SEQ ID NO:43:

```
GGGAATTCTT AGAG ATG GCT CTG CAG ATC CCC AGC CTC CTC CTC TCG GCT        50
               Met Ala Leu Gln Ile Pro Ser Leu Leu Leu Ser Ala
                1                5                    10

GCT GTG GTG GTG CTG ATG GTG CTG AGC AGC CCA GGG ACT GAG GGC GGA        98
Ala Val Val Val Leu Met Val Leu Ser Ser Pro Gly Thr Glu Gly Gly
         15                   20                  25

GAC TCC GAA AGG CAT TTC GTG TAC CAG TTC ATG GGC GAG TGC TAC           143
Asp Ser Glu Arg His Phe Val Tyr Gln Phe Met Gly Glu Cys Tyr
     30                   35                  40
```

( 2 ) INFORMATION FOR SEQ ID NO:44:

( i ) SEQUENCE CHARACTERISTICS:
        ( A ) LENGTH: 215 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
    ( A ) NAME/KEY: CDS
    ( B ) LOCATION: 15..215

( x i ) SEQUENCE DESCRIPTION: SEQ ID NO:44:

```
GGGAATTCTT AGAG ATG GCT CTG CAG ATC CCC AGC CTC CTC CTC TCG GCT        50
               Met Ala Leu Gln Ile Pro Ser Leu Leu Leu Ser Ala
                1                5                    10

GCT GTG GTG GTG CTG ATG GTG CTG AGC AGC CCA GGG ACT GAG GGC GGA        98
Ala Val Val Val Leu Met Val Leu Ser Ser Pro Gly Thr Glu Gly Gly
         15                   20                  25

GAC TCC GAA GCT AGC TTT GAG GCT CAG GGT GCA CTG GCC AAC ATT GCT       146
Asp Ser Glu Ala Ser Phe Glu Ala Gln Gly Ala Leu Ala Asn Ile Ala
     30                   35                  40

GTC GAC AAG GCT GGA GGT GGT GGA TCC GGT GGA GGG GGA AGT GGA GGT       194
Val Asp Lys Ala Gly Gly Gly Gly Ser Gly Gly Gly Gly Ser Gly Gly
 45                  50                  55                  60

GGA GGG TCT GAA AGG CAT TTC                                            215
Gly Gly Ser Glu Arg His Phe
                 65
```

( 2 ) INFORMATION FOR SEQ ID NO:45:

( i ) SEQUENCE CHARACTERISTICS:
        ( A ) LENGTH: 67 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

```
Met Ala Leu Gln Ile Pro Ser Leu Leu Leu Ser Ala Ala Val Val Val
 1                5                    10                  15

Leu Met Val Leu Ser Ser Pro Gly Thr Glu Gly Gly Asp Ser Glu Ala
             20                  25                  30

Ser Phe Glu Ala Gln Gly Ala Leu Ala Asn Ile Ala Val Asp Lys Ala
         35                  40                  45

Gly Gly Gly Gly Ser Gly Gly Gly Gly Ser Gly Gly Gly Gly Ser Glu
```

```
            50                    55                     60
Arg His Phe
65
```

PRODUCT AND PROCESS FOR T CELL REGULATION

This invention was made in part with government support under USPHS Grant AI 118785 and USPHS Grant AI 22295, both awarded by the National Institutes of Health. The government has certain rights to this invention.

FIELD OF THE INVENTION

The present invention relates to a product and process for regulating the activity of T cells using major histocompatibility complexes (MHC) stably linked to antigenic peptides.

BACKGROUND

A wide variety of medical treatments require regulation of the immune response in a patient. Such treatments include, for example, treatments for autoimmune diseases, immunodeficiency diseases, immunoproliferative diseases, and treatments involving the transplantation of organs and skin. Traditional reagents and methods used to regulate an immune response in a patient often result in unwanted side effects. For example, immunosuppressive reagents such as cyclosporin A, azathioprine, and prednisone are used to suppress the immune system of a patient with an autoimmune disease or patients receiving transplants. Such reagents, however, suppress a patient's entire immune response, thereby crippling the ability of the patient to mount an immune response against infectious agents not involved in the original disease. Due to such harmful side effects and the medical importance of immune regulation, reagents and methods to regulate specific parts of the immune system have been the subject of study for many years.

Introduction of an antigen into a host initiates a series of events culminating in an immune response. In addition, self-host antigens can result in activation of the immune response. A major portion of the immune response is regulated by presentation of antigen by major histocompatibility complexes (MHCs). MHCs bind to peptide fragments derived from antigens to form complexes that are recognized by T cell receptors on the surface of T cells, giving rise to the phenomenon of MHC-restricted T cell recognition. The ability of a host to react to a given antigen (responsiveness) is influenced by the spectrum of MHC proteins expressed by the host. Responsiveness correlates to the ability of specific peptide fragments to bind to particular MHC proteins.

T cell receptors (TCRs) recognize antigens that are bound by MHC. Recognition of MHC complexed with peptide (MHC-peptide complex) by TCR can effect the activity of the T cell bearing the TCR. Thus, MHC-peptide complexes are important in the regulation of T cell activity and thus, in regulating an immune response.

Prior to the present invention, MHC-peptide complexes have proven to be difficult to produce and, therefore, expensive to make in large quantities. The peptides, derived synthetically or in vivo, did not bind to MHC in a manner that allowed for a stable and reliable complex required for medical uses. MHC-peptide complexes are currently produced by isolating MHC protein from large numbers of cells presenting membrane-bound MHC protein and mixing in solution the isolated MHC protein with purified peptides. Separation of the MHC protein is a laborious, multi-step process and requires a large number of cells to obtain sufficient amounts of MHC protein. In addition, considerable effort is required to obtain purified peptide to mix with the MHC protein. Moreover, the association between individual peptides and MHC has been shown to be unstable.

Particular MHC-peptide complexes and methods of making them have been suggested by various investigators, including Clark et al., U.S. Pat. No. 5,260,422, issued Nov. 9, 1993; Sharma et al., U.S. Pat. No. 5,194,425, issued Mar. 16, 1993; Sharma et al., U.S. Pat. No. 5,130,297, issued Jul. 14, 1992; Nag et al., PCT Application No. WO 93/09810, published May 27, 1993; and Sanderson, U.S. application Ser No. 4,400,376, published Aug. 23, 1983. Prior investigators, however, have only disclosed the use of soluble, as opposed to membrane bound, MHC-peptide complexes. Moreover, methods to produce such complexes suffered from the unpredictable and unstable association of peptides with MHC.

As such, there is a need for a product and process that allows for the cost-effective production of large quantities of both soluble and membrane bound MHC-peptide complexes wherein the peptides are stably associated with the MHC proteins.

SUMMARY

The present invention relates to an antigenic peptide covalently linked to a major histocompatibility complex (MHC) protein by a novel linker, thereby enabling the formation of a stable MHC-peptide complex, that is capable of being recognized by a T cell receptor (TCR), alone or in combination with additional MHC protein chains. Such stable complexes are useful for therapeutic purposes and experimental purposes.

One aspect of the present invention includes a Peptide-L-MHC molecule comprising a peptide, a linker, and an MHC segment. The peptide portion of the Peptide-L-MHC molecule is linked to the MHC segment by the linker. Also included is a method to produce Peptide-L-MHC molecule of the present invention.

One embodiment of the present invention includes a Peptide-L-MHC molecule comprising a peptide, a linker and an MHC segment comprising an MHC class I $\alpha$ chain. In a preferred embodiment, the Peptide-L-MHC molecule further includes an MHC class I $\beta$2m subunit that associates with the MHC class I $\alpha$ chain to form a Peptide-L-MHC$_{\alpha+\beta 2m}$ composition having a functional peptide binding site.

Another embodiment of the present invention includes a Peptide-L-MHC molecule comprising a peptide, a linker and an MHC segment comprising an MHC class II $\beta$ chain. In a preferred embodiment, the Peptide-L-MHC molecule further comprises an MHC class II $\alpha$ chain that associates with the MHC class II $\beta$ chain to form a Peptide-L-MHC$_{\alpha+\beta}$ composition having a functional peptide binding site.

The present invention is also directed to formulations comprising Peptide-L-MHC molecules combined with suitable carriers such that the formulations are capable of effecting an immune response. Such formulations are useful as pharmaceutical reagents for the treatment of diseases including autoimmune diseases, immunostimulatory diseases, immunoproliferation diseases and graft-host rejection. The formulations are also useful as experimental reagents. In one embodiment, compositions and molecules of the present invention are anchored to the plasma membranes of cells that are incapable of stimulating a T cell response. Cells incapable of stimulating a T cell response include red blood cells, fibroblasts, pluripotent progenitor cells, epithelial cells and neural cells.

In another embodiment, compositions and molecules of the present invention are anchored in plasma membranes of cells that are capable of stimulating a T cell response. Cells capable of stimulating a T cell response include macrophages, B cells and dendritic cells.

One embodiment of the present invention includes Peptide-L-MHC$_{\alpha+\beta 2m}$ compositions anchored to the plasma membrane of cells that are capable of stimulating a T cell response and to cells that are incapable of stimulating an immune response. Another embodiment of the present invention includes Peptide-L-MHC$_{\alpha+\beta}$ compositions anchored to the plasma membrane of cells that are capable of stimulating a T cell response and to cells that are incapable of stimulating an immune response.

Another aspect of the present invention includes a nucleic acid molecule having a sequence encoding a Peptide-L-MHC molecule comprising a peptide joined by a linker to an MHC segment. The present invention also includes recombinant molecules and recombinant cells that include nucleic acid molecules of the present invention and a method to produce nucleic acid molecules of the present invention.

BRIEF DESCRIPTION OF THE FIGURES

FIG. 4 illustrates the expression of IA$^b$-Ea protein by M12.C3 cells.

FIG. 7 illustrates the expression of IA$^b$-Ea protein on fibroblast cells.

DETAILED DESCRIPTION

Figure 1:
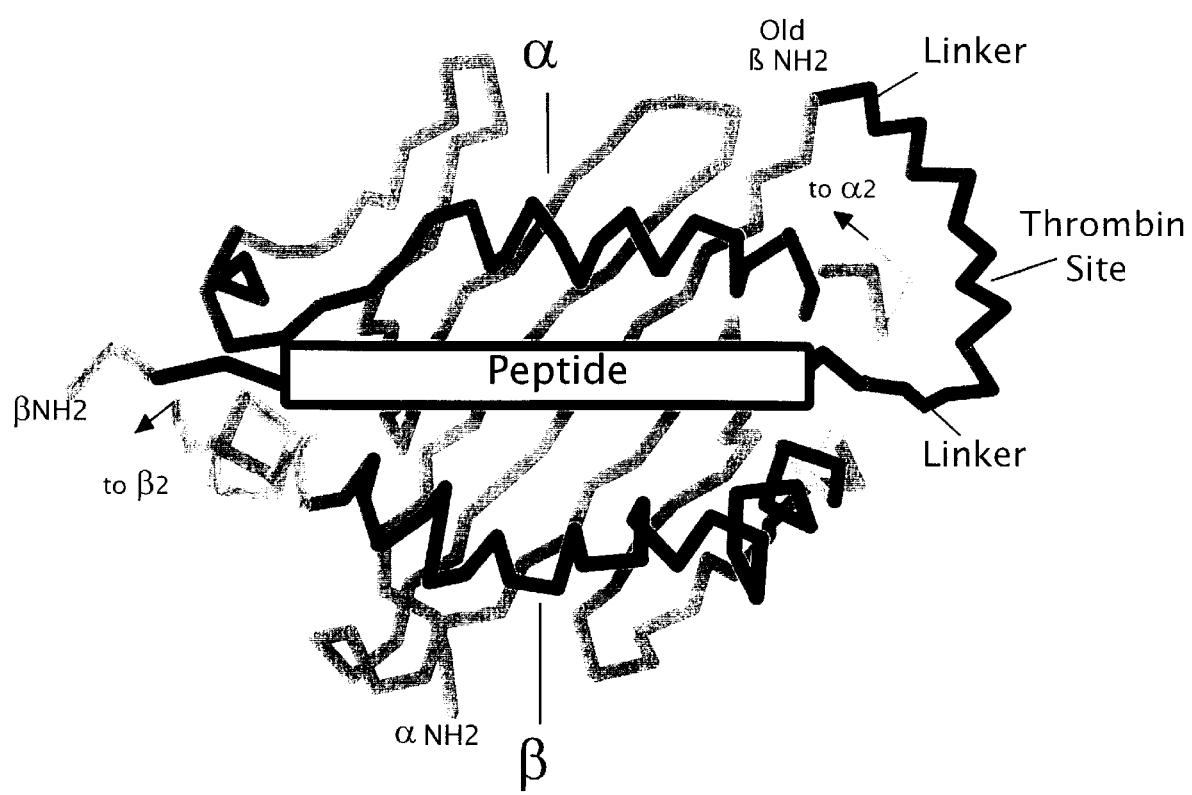
FIG. 1 is a schematic representation of a peptide covalently associated with the binding site of an MHC protein a linker.

The present invention relates to a novel product and process for regulating an immune response. The present invention includes a novel Peptide-L-MHC molecule having at least three components: (1) an antigenic peptide (Peptide) capable of effecting an immune response; (2) a linker (L); and (3) a major histocompatibility complex (MHC) segment. The peptide is linked to the MHC segment by the linker. The invention is particularly advantageous in that it provides an antigenic peptide covalently linked to an MHC protein by a linker, thereby facilitating the formation of a stable MHC-peptide complex, alone or in combination with additional MHC protein chains, that is capable of being recognized by an α/β T cell receptor (TCR). Novel Peptide-L-MHC molecules of the present invention can form a functional peptide binding site alone or in combination with an additional MHC protein chain such that the molecule is capable of being bound by a T cell receptor. Particular embodiments of Peptide-L-MHC molecules that are capable of being bound by a T cell receptor include a Peptide-L-MHC$_{\alpha+\beta 2m}$ composition and a Peptide-L-MHC$_{60\ +\beta}$ composition as described in detail below. A representation of an antigenic peptide bound to a binding site of an MHC protein and covalently associated with the MHC protein is shown in FIG. 1.

The major histocompatibility complex is a collection of genes encoding glycoproteins called major histocompatibility complex (MHC) proteins. In vivo, the primary function of an MHC protein is to present antigen in a form capable of being recognized by a TCR. An MHC protein is bound to an antigen in the form of an antigenic peptide to form an MHC-peptide complex. As used herein, "MHC-peptide complex" refers to any MHC protein having an antigenic peptide bound to one or more of the MHC protein's peptide binding sites.

As used herein, "TCR recognition" refers to the ability of a TCR to bind to an MHC peptide complex. The presentation of antigen by an MHC protein to the T cell normally leads to a T cell response that is clone specific. Normal T cells are distinguished from T cell hybridomas which may differ from normal T cells in their activation reactions. As used herein, "antigen presentation" refers to presenting antigen in such a manner that at least a portion of the antigen is available to be bound by a TCR. A T cell response occurs when a TCR recognizes an MHC protein bound to an antigenic peptide, thereby altering the activity of the T cell bearing the TCR. As used herein, a "T cell response" can refer to the activation, induction of anergy, or death of a T cell that occurs when the TCR of the T cell is bound by an MHC-peptide complex. As used herein, "activation" of a T cell refers to induction of signal transduction pathways in the T cell resulting in production of cellular products (e.g., interleukin-2) by that T cell. "Anergy" refers to the diminished reactivity by a T cell to an antigen. Activation and anergy can be measured by, for example, measuring the amount of IL-2 produced by a T cell after and MHC-peptide complex has bound to the cell's TCR. Anergic cells will have decreased IL-2 production when compared with stimulated T cells. Another method for measuring the diminished activity of anergic T cells includes measuring intracellular and or extracellular calcium mobilization by a T cell upon engagement of its TCR's. As used herein, "T cell death" refers to the permanent cessation of substantially all functions of the T cell.

MHC proteins are classified in two categories: class I and class II MHC proteins. An MHC class I protein is an integral membrane protein comprising a glycoprotein heavy chain having three extracellular domains (i.e., $\alpha_1$, $\alpha_2$ and $\alpha_3$ and two intracellular domains (i.e., a transmembrane domain (TM) and a cytoplasmic domain (CYT)). The heavy chain is noncovalently associated with a soluble subunit called β2-microglobulin (β2m). An MHC class II protein is a heterodimeric integral membrane protein comprising one α and one β chain in noncovalent association. The α chain has two extracellular domains ($\alpha_1$ and $\alpha_2$), and two intracellular domains (a TM domain and a CYT domain). The β chain contains two extracellular domains ($\beta_1$ and $\beta_2$), and a TM and CYT domain.

Antigenic peptides associate with an MHC protein by binding to a peptide binding site of an MHC protein. As used herein, the term "peptide binding site" refers to the portion of an MHC protein capable of binding peptide. Peptide binding sites can be internal binding sites (e.g., peptide binding grooves) or external binding sites (e.g., binding sites on the external surface of an MHC protein). The conformation of a peptide binding site is capable of being altered upon binding of an antigenic peptide to enable proper alignment of amino acid residues important for TCR binding to the MHC protein and or peptide.

The domain organization of class I and class II proteins form the peptide binding site. In one embodiment of the present invention, a peptide binding site includes a peptide binding groove. A peptide binding groove refers to a portion of an MHC protein which forms a cavity in which a peptide can bind. A peptide binding groove of a class I protein can comprise portions of the $\alpha_1$ and $\alpha_2$ domains. A binding groove of a class II protein can comprise portions of the $\alpha_1$ and $\beta_1$ domains capable of forming two β-pleated sheets and two α helices. Without being bound by theory, it is believed that a first portion of the $\alpha_1$ domain forms a first β-pleated sheet and a second portion of the $\alpha_1$ domain forms a first a helix. A first portion of the $\beta_1$ domain forms a second β-pleated sheet and a second portion of the $\beta_1$ domain forms a second a helix. The x-ray crystallographic structure of class II protein with a peptide engaged in the binding groove of the protein indicates that one or both ends of the engaged peptide can project beyond the MHC protein (Brown et al., pp. 33–39, 1993, *Nature,* Vol. 364). Thus, the ends of the $\alpha_1$ and $\beta_1$ α helices of class II apparently form an open cavity such that the ends of the peptide bound to the binding groove are not buried in the cavity. Moreover, the x-ray crystallographic structure of class II proteins indicates that the N-terminal end of the MHC β chain apparently projects from the side of the MHC protein in an unstructured manner since the first 4 amino acid residues of the β chain could not be assigned by x-ray crystallography.

In another embodiment, a peptide binding site includes an external peptide binding site in which an external surface of an MHC protein (which does not include a substantial portion of a peptide binding groove) is capable of being bound by an antigenic peptide. Such external surfaces can include any amino acid side-chain available for binding by an antigenic peptide on the external surface of the MHC protein. An external binding site on a class I protein can include the external surface of at least a portion of an α chain or β2m subunit. An external binding site on a class II protein can include the external surface of at least a portion of an α chain or β chain. Preferably, the external binding site of a class II protein includes: the $\alpha_1$ domain or $\alpha_2$ domain of the α chain; the $\beta_1$ domain or $\beta_2$ domain of the β chain; or a combination of these domains.

In yet another embodiment, a binding site can also comprise a "combined binding site" having portions of an external binding site and portions of a binding groove which can be bound by an antigenic peptide.

One embodiment of the present invention is a Peptide-L-MHC molecule, the description of which can be best conveyed by individually discussing the various components of the novel Peptide-L-MHC. An MHC segment of the present invention can be any portion of an MHC protein that is sufficient to form, either alone or in combination with the appropriate portion of an MHC protein chain, a peptide binding site capable of presenting antigenic peptide in a manner that is able to be recognized by a TCR.

In one embodiment, an MHC segment of a Peptide-L-MHC molecule of the present invention can comprise at least a portion of a class I MHC protein, at least a portion of a class II MHC protein, or a hybrid thereof. As used herein, a "hybrid" refers to the attachment of at least a portion of a class I MHC protein to at least a portion of a class II MHC protein, to form a single MHC functional protein. According to the present invention, "at least a portion" refers to a portion of an MHC protein capable of forming a peptide binding site or capable of forming a binding site upon addition of another chain of an MHC protein. Preferred MHC segments of the present invention include segments having at least a portion of a class I protein, and segments having at least a portion of a class II MHC protein.

One embodiment of the present invention is a soluble Peptide-L-MHC molecule. Soluble molecules of the present invention include Peptide-L-MHC molecules that are not contained in a lipid-containing substrate. A secreted Peptide-L-MHC molecule can be produced using an MHC segment that lacks sufficient amino acid sequences capable of anchoring the molecule into a lipid-containing substrate, such as an MHC transmembrane domain and or an MHC cytoplasmic domain.

In another embodiment, a Peptide-L-MHC molecule is capable of being bound by a lipid-containing substrate, preferably by a plasma membrane of a cell that produces the Peptide-L-MHC molecule. As used herein, the term "anchored" refers to the insertion of a protein in a lipid-containing substrate such that any extracellular domains are on the outside of the substrate. A Peptide-L-MHC molecule of the present invention capable of being bound by a lipid-containing substrate is referred to herein as a membrane-bound Peptide-L-MHC molecule. An MHC segment useful in the production of a membrane-bound Peptide-L-MHC molecule can include any amino acid sequence capable of anchoring a protein into a lipid-containing substrate combined with the extracellular domains of the MHC protein. Preferably, the MHC segment contains at least one MHC transmembrane domain and at least a portion of at least one MHC cytoplasmic domain.

In another embodiment, an MHC segment of the present invention can include at least a portion of a single chain such as a class I α chain; a class II α chain; a class II β chain; or hybrids thereof. Hybrids can include any combination of such portions, such as a single chain comprising a portion of a class I α chain attached to a portion of a class II β chain. Peptide-L-MHC molecules containing such MHC segments can be combined with an appropriate distinct MHC protein chain capable of associating with the Peptide-L-MHC molecule to form a complex having a function peptide binding site.

A preferred class I α chain of the present invention contains class I $\alpha_1$, $\alpha_2$ and $\alpha_3$ domains. A preferred class II α chain of the present invention contains class II $\alpha_1$ and $\alpha_2$ domains. A preferred class II β chain contains $\beta_1$ and $\beta_2$ domains. A preferred hybrid MHC segment of the present invention includes at least portions of a class I α chain and a class II β chain.

Preferred embodiments of an MHC segment of the present invention include segment having a class II β chain which includes a $\beta_1$ domain, a $\beta_2$ domain, and a segment having a class II β chain which includes a $\beta_1$ domain, a β chain transmembrane domain and a β chain cytoplasmic domain.

An antigenic peptide of the present invention can comprise any peptide that is capable of binding to an MHC protein in a manner such that the MHC-peptide complex can bind to TCR and effect a T cell response. A peptide of the present invention can be synthesized by a cell, externally or internally hydrolyzed, or a post-translation modification product.

Examples of antigenic peptides can be include: an antigenic peptide synthesized inside of a cell; an antigenic peptide synthesized outside of a cell; an antigenic peptide hydrolyzed inside of a cell; or an antigenic peptide hydrolyzed outside of a cell. Such examples include antigenic peptides derived from exogenous antigens which enter a cell and exogenous antigens which remain outside of a cell.

Antigenic peptides that are produced by hydrolysis of antigens undergo hydrolysis prior to binding of the antigen to an MHC protein. Class I MHC proteins typically present antigenic peptides derived from proteins actively synthesized by a cell. In contrast, class II MHC proteins typically present antigenic peptides derived from exogenous protein that enter a cell's endocytic pathway. Intracellular trafficking permits an antigenic peptide to become associated with an MHC protein. The resulting MHC-peptide complex then travels to the surface of the cell where it is available for interaction with a TCR.

In one embodiment, an externally derived antigenic peptide can become associated with unoccupied MHC proteins on the surface of cell. Such antigenic peptides can be generated by, for example, proteolytic digestion of proteins in extracellular fluids such as serum. The MHC-peptide complex can then be presented to a TCR. In another embodiment, antigenic peptides that are not hydrolyzed can associate with unoccupied MHC proteins on the surface of a T cell and can be presented to a TCR.

Another embodiment of the present invention is a groove-binding antigenic peptide, which is an antigenic peptide that is capable of binding to a peptide binding groove of an MHC protein in such a manner that the resulting Peptide-MHC complex can bind to a TCR. It is believed that the binding of an antigenic peptide to an MHC peptide binding groove can control the spatial arrangement of MHC and or antigenic peptide amino acid residues recognized by a TCR. Such spatial control may be due in part to hydrogen bonds formed between a peptide and an MHC protein. Preferably, the length of a groove-binding antigenic peptide extends from about 5 to about 40 amino acid residues, more preferably from about 6 to about 30 amino acid residues, and even more preferably from about 8 to about 20 amino acid residues.

Preferred groove-binding antigenic peptides include those that bind to MHC protein involved in autoimmune diseases, immunodeficiency diseases, immunoproliferation diseases, and graft-host rejection. More preferred groove specific peptides of the present invention include Arg-Ala-Asp-Leu-Ile-Ala-Tyr-Leu-Lys-Gln-Ala-Thr-Lys (SEQ ID NO:1),Val-His-Ala- Ala-His-Ala-Glu-Ile-Asn-Glu-Ala-Gly-Arg(SEQ ID NO:2),Arg-Ala-Asp-Leu-Ile-Ala-Tyr-Leu-Lys-Gln-Ala-Thr-Lys, (SEQ ID NO:3) Val-His-Ala-Ala-His-Ala-Glu-Ile-Asn-Glu-Ala-Gly-Arg (SEQ ID NO:4) and Ala-Ser-Phe-Glu-Ala-Gln-Gly-Ala-Leu-Ala-Asn-Ile-Ala-Val-Asp-Lys-Ala (SEQ ID NO:5) and functional equivalents thereof.

As stated above, antigenic peptides useful in the present invention can either bind to a binding groove, to an external binding site, or to a combined binding site. External antigenic peptides of the present invention can bind to both a TCR and an MHC protein in such a manner that a T cell response occurs. Peptides useful in the present invention include superantigens, a family of T cell stimulatory proteins that are capable of binding MHC protein and TCR to induce a T cell response. A superantigen is believed to bind to at least a portion of the α chain of class II, the β chain of class II, or a combination of the α and β chains of class II. Superantigens are also believed to bind to at least a portion of a $V_\beta$ domain of a TCR.

Preferred external peptides of the present invention include polypeptides having a molecular weight of at least about 5 kD, more preferably at least about 15 kD, and even more preferably at least about 20 kD. Suitable antigenic peptides of the present invention include peptides comprising at least a portion of an antigen selected from a group consisting of autoantigens, infectious agents, toxins, allergens, or mixtures thereof. Preferred autoantigens of the present invention include, but are not limited to, antigens which result in the development of systemic lupus, rheumatoid arthritis, myasthenia gravis, multiple sclerosis, and insulin dependent diabetes mellitus.

Preferred infectious agents of the present invention include, but are not limited to, bacteria, viruses, and eukaryotic parasites. Preferred animal parasites include protozoan parasites, helminth parasites (such as nematodes, cestodes, trematodes, ectoparasites and fungi.

Preferred allergens of the present invention include, but are not limited to plant, animal, bacterial, parasitic allergens and metal-based allergens that cause contact ensitivity. More preferred allergens include weed, grass, tree, peanut, mite, flea, and cat antigens.

Preferred toxins of the present invention include, but are not limited to, staphylococcal enterotoxins, toxic shock syndrome toxin, retroviral antigens, streptococcal antigens, mycoplasma, mycobacterium, and herpes viruses. Retroviral antigens include antigens derived from human immunodeficiency virus. Even more preferred toxins include SEA, SEB, $SE_{1-3}$, SED, and SEE.

A Peptide-L-MHC molecule of the present invention contains a novel linker which comprises an amino acid sequence that covalently associates an MHC segment with an antigenic peptide. Covalent bonds are formed between the antigenic peptide and the linker, and between the linker and the MHC segment. The linker is distinguished from a peptide linkage which refers to the chemical interaction between two amino acids.

Prior to the development of novel Peptide-L-MHC molecules of the present invention, MHC-peptide complexes suffered from unpredictable and unstable association of peptides with MHC proteins. In their native state, antigenic peptides associate with MHC proteins in a noncovalent manner resulting in an inherently unstable MHC-peptide complex. In addition, MHC-peptide complexes derived from mixing antigenic peptides and MHC proteins in vitro suffer even greater instability problems because the formation and stability of the complexes can be affected by the equilibrium between the complex and non-complexed peptides. The instability of both native and man-made MHC-peptide complexes limits the use of the complexes as reliable reagents for medical and or experimental use. The novel linker of the present invention alleviates such problems and allows for the production of MHC-peptide complexes that are uniquely suitable for use as therapeutic and experimental agents. The ability to attach an antigenic peptide to an MHC segment via a linker to produce a functional MHC-peptide complex is unexpected because the association of antigenic peptide with the MHC peptide binding site is considered to be a tight and carefully defined fit. As such, a skilled artisan would predict that a linker would hinder the ability of an antigenic peptide to bind to an MHC peptide binding site by, for example, stearic hindrance due to the size or location of a linker relative to an antigenic peptide and a peptide binding site, or to amino acid charge interactions between a linker and an MHC protein. A skilled artisan would also predict that a linker would hinder the interaction of an MHC protein bound by antigenic peptide with a TCR by stearic hindrance and/or amino acid charge interactions. Despite such prevalent beliefs in the field, the present inventors have identified and produced linkers that do not substantially hinder the association of an antigenic peptide with an MHC binding site and, moreover, stabilize the association of the peptide with the MHC.

A linker useful in the production of a Peptide-L-MHC molecule can comprise any amino acid sequence that facilitates the binding of an antigenic peptide to an MHC protein. A linker can facilitate antigenic peptide binding by, for example, maintaining an antigenic peptide within a certain distance of an MHC peptide binding site to promote efficient binding. The linker enhances the ability of a combined aggregate of antigenic peptide and MHC protein to act as a unit in triggering a desired immune response. Preferably, a linker of the present invention is capable of facilitating the binding of the antigenic peptide portion of a Peptide-L-MHC molecule to the MHC protein segment of either a Peptide-L-MHC$_{\alpha+\beta}$ composition or a Peptide-L-MHC$_{\alpha+\beta 2m}$ composition (as defined in detail below) that is capable of being recognized by a TCR.

According to the present invention, a linker of the present invention stabilizes the association of an antigenic peptide with an MHC peptide binding site, resulting in the formation of a stable composition that can be recognized by a TCR. As used herein, the term "stability" refers to the maintenance of the association of a peptide with an MHC peptide binding site in the presence of forces that typically cause the dissociation of complexed peptide and MHC protein. The stability of a peptide bound to an MHC peptide binding site can be measured in a variety of ways known to those skilled in the art. For example, an MHC-peptide complex can be passed over an high pressure liquid chromatography (HPLC) sizing column and analyzed for maintenance of the complex. In addition, MHC-peptide complexes can be incubated in increasing concentrations of sodium dodecyl sulfate (SDS) for an appropriate amount of time, at an appropriate temperature, and analyzed for maintenance of the complex. Suitable concentrations of SDS include from about 0.01% SDS to about 5% SDS. The stability of Peptide-L-MHC molecules (including, but not limited to Peptide-L-MHC$_{\alpha+\beta 2m}$ compositions, or Peptide-L-MHC$_{\alpha+\beta}$ compositions) preferably is substantially the same as or greater than the stability of a native form of the complex. Preferably, the stability of such molecules and compositions are measured by passage of such proteins over HPLC sizing columns and comparing the peak location of eluant proteins with comparable native protein (i.e., peptide bound MHC protein that does not possess a linker) passed over the same or a substantially similar column.

A linker useful in the production of a Peptide-L-MHC molecule can comprise any amino acid sequence that does not substantially hinder interaction of an antigenic peptide with an MHC protein or hinder interaction of an MHC protein bound by peptide with a TCR.

The length of a linker of the present invention is preferably sufficiently short (i.e., small enough in size) such that the linker does not substantially inhibit binding between the antigenic peptide and the MHC segment of a Peptide-L-MHC molecule or inhibit TCR recognition. Preferably, the length of a linker of the present invention is from about 1 amino acid residue to about 40 amino acid residues, more preferably from about 5 amino acid residues to about 30 amino acid residues, and even more preferably from about 8 amino acid residues to about 20 amino acid residues.

In addition, the amino acid composition of a linker of the present invention is substantially neutral such that the linker does not inhibit MHC-peptide complex formation or TCR recognition by the complex. As used herein, the term "neutral" refers to amino acid residues sufficiently uncharged or small in size so that they do not prevent interaction of a linker with an MHC segment. Preferred amino acid residues for linkers of the present invention include, but are not limited to glycine, alanine, leucine, serine, valine, threonine, and proline residues. More preferred linker amino acid residues include glycine, serine, leucine, valine, and proline residues. Linker compositions can also be interspersed with additional amino acid residues, such as arginine residues.

Linker amino acid residues of the present invention can occur in any sequential order such that there is no interference with binding of an antigenic peptide to an MHC protein or of the resulting MHC-peptide complex with a TCR. Linkers having the amino acid sequence Gly-Gly-Gly-Gly-Ser-Leu-Val-Pro-Arg-Gly-Ser-Gly-Gly-Gly-Gly-Ser (SEQ ID NO: 6)and Gly-Gly-Gly-Gly-Ser (SEQ ID NO: 7)Gly-Gly-Gly-Gly-Ser are particularly preferred.

One embodiment of the present invention relates to a linker having an amino acid sequence that contains a target site for an enzyme capable of cleaving proteins. Such linkers are hereinafter referred to as "processable linkers". Processable linkers can be designed to inhibit TCR recognition of a Peptide-L-MHC molecule until such Peptide-L-MHC molecule reaches a targeted site of action (i.e., a site of inflammation). At the site of action, the processable linker could be cleaved by an enzyme present at the site, thereby transforming the inactive Peptide-L-MHC molecule into an active form capable of being recognized by a TCR. The Peptide-L-MHC could be inactive prior to cleavage due to an antigenic peptide being unable to bind to an MHC protein or due to the inability of a TCR to recognize the MHC protein bound by the antigenic peptide. Charge and/or stearic hindrance can be eliminated once the linker is cleared, thereby allowing the MHC-peptide complex to be recognized by a TCR. A processable linker can further comprise an immunogenic sequence representing a foreign determinant that can be removed by cleaving serum enzyme target sites also contained on the linker.

Preferred processable linkers of the present invention include linkers containing target sites for enzymes such as collagenases, metalloproteases, serine proteases, cysteine proteases, kallikriens, thrombin, and plasminogen activators. A preferred processable linker of the present invention includes a linker having a thrombin cleavage site of Leu-Val-Pro-Arg-Gly-Ser-(SEQ ID NO:8).

Suitable linkers useful in the present invention can be designed using various methods. For example, x-ray crystallographic data of an MHC protein can be used to design a linker of suitable length and charge such that the linker does not interfere with TCR recognition of the MHC-peptide complex. Suitable linkers can also be identified by producing large numbers of different Peptide-L-MHC molecules having different combinations of antigenic peptides, linkers and MHC segments and determining if those molecules, alone or in combination with other distinct MHC protein chains, can be recognized by a TCR. In addition, linkers know to function well with one particular Peptide-L-MHC molecule can be combined with other antigenic peptide and MHC segment combinations, and tested for the ability of the resulting Peptide-L-MHC molecule to affect a T cell response, either alone or in combination with other MHC protein chains.

A Peptide-L-MHC molecule of the present invention can, either alone or in combination with another MHC protein chain, form a peptide binding site. A Peptide-L-MHC molecule of the present invention can be combined with a distinct MHC protein chain, thereby forming a composition having a peptide binding site. Such a composition is capable of being recognized by a TCR. In one embodiment of the present invention, a Peptide-L-MHC molecule having an MHC segment comprising an MHC class I α chain is associated with at least a portion of a class I β2m subunit to form a Peptide-L-MHC$_{\alpha+\beta 2m}$ composition having a functional peptide binding site. Association between the Peptide-L-MHC molecule and the β2m subunit can be covalent or noncovalent.

In another embodiment, a Peptide-L-MHC molecule of the present invention having an MHC segment comprising an MHC class II β chain is associated with at least a portion of an MHC class II α chain to form a Peptide-L-MHC$_{α+β}$ composition having a functional peptide binding site. Association between the Peptide-L-MHC molecule and the class II β chain can be covalent or noncovalent.

In a further embodiment, a Peptide-L-MHC molecule of the present invention can include an effector component, such as a label or a toxin. The effector component can be conjugated either to the MHC segment or to the peptide of a Peptide-L-MHC molecule. Suitable toxins include, but are not limited to: double chain toxins (i.e., toxins having A and B chains), such as diphtheria toxin, ricin toxin, Pseudomonas exotoxin, modeccin toxin, abrin toxin, and shiga toxin; single-chain toxins, such as pokeweed antiviral protein, alpha-amanitin, and ribosome inhibiting proteins; and chemical toxins, such as melphalan, methotrexate, nitrogen mustard, doxorubicin and daunomycin. Suitable labels include, but are not limited to fluorescent labels, biotin, at least a portion of an immunoglobulin protein, metallic compounds, luciferin, radiolabels and enzymes.

Another aspect of the present invention relates to a nucleic acid molecule that encodes a protein of the present invention comprising the Peptide-L-MHC molecules disclosed herein. According to the present invention, references to nucleic acids also refer to nucleic acid molecules. A nucleic acid molecule can be DNA, RNA, or hybrids or derivatives of either DNA or RNA. Nucleic acid molecules of the present invention can include regulatory regions that control expression of the nucleic acid molecule (e.g., transcription or translation control regions), full-length or partial coding regions, and combinations thereof. Any portion of a nucleic acid molecule of the present invention can be produced by: (1) isolating the molecule from its natural milieu; (2) using recombinant DNA technology (e.g., PCR amplification, cloning); or (3) using chemical synthesis methods. A nucleic acid of the present invention can include functional equivalents of natural nucleic acid molecules encoding an MHC segment or a peptide, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a protein of the present invention capable of forming compositions that can be recognized by T cell receptors. Preferred functional equivalents include sequences capable of hybridizing under stringent conditions, to at least a portion of a Peptide-L-MHC molecule encoding nucleic acid molecule (according to conditions described in Sambrook et al., *Molecular Cloning: A Laboratory Manual*, Cold Spring Harbor Labs Press, 1989, which is incorporated herein by reference in its entirety). As guidance in determining what particular modifications can be made to any particular nucleic acid molecule, one of skill in the art should consider several factors that, without the need for undue experimentation, permit a skilled artisan to appreciate workable embodiments of the present invention. For example, such factors include modifications to nucleic acid molecules done in a manner so as to maintain particular functional regions of the encoded proteins including, a working peptide binding domain, a TCR binding domain and a linker that does not substantially interfere with desired binding interactions. Functional tests for these various characteristics (e.g., binding studies) allows one of skill in the art to determine what modifications to nucleic acid sequences would be appropriate and which would not.

One embodiment of the present invention includes a nucleic acid molecule encoding a Peptide-L-MHC molecule having at least three components: (1) an MHC segment; (2) a peptide; and (3) a linker. Suitable and preferred segments, peptides and linkers for use in the present invention are heretofore disclosed. A nucleic acid molecule of the present invention comprises at least one nucleic acid sequence encoding an MHC segment, covalently attached (by base pair linkage) to at least one nucleic acid sequence encoding a linker, which is itself covalently attached (by base pair linkage) to at least one nucleic acid sequence encoding an antigenic peptide. The nucleic acid sequences are attached in such a manner that the sequences are transcribed in-frame, thereby producing a functional Peptide-L-MHC molecule capable of forming a peptide binding site, alone or in combination with another MHC protein chain.

Preferred nucleic acid molecules encoding Peptide-L-MHC molecules include: nucleic acid sequences encoding an MHC class I α chain, a linker and an antigenic peptide, wherein the peptide is linked to the class I α chain by the linker; and an MHC class II β chain, a linker and an antigenic peptide, wherein the peptide is linked to the class II β chain by the linker. Particularly preferred nucleic acid molecules encode IEβ$^k$ or a functional equivalent thereof; IAβ$^d$ or a functional equivalent thereof; and IAβ$^b$ or a functional equivalent thereof. A portion of each nucleic acid molecule encoding a component (i.e., an MHC segment, a linker, or an antigenic peptide) of a Peptide-L-MHC molecule can be covalently associated (using standard recombinant DNA methods) to any other sequence encoding at least a portion of a distinct component to produce a Peptide-L-MHC molecule of the present invention. A nucleic acid sequence encoding a linker is preferably covalently associated (by base pair linkage, e.g., ligated) to a nucleic acid sequence encoding an MHC segment and encoding a linker. In one embodiment, the 3' end (end encoding the C-terminus) of a nucleic acid molecule encoding an antigenic peptide of the present invention is ligated to the 5' end (end encoding the N-terminus) of a nucleic acid molecule encoding a linker of the present invention and the 3' end of the nucleic acid sequence encoding the linker is ligated to the 5' end of a nucleic acid molecule encoding an MHC segment. Particular embodiments of nucleic acid molecules encoding Peptide-LMHC of the present invention are shown in Tables 2–6. The construction of such molecules is described in detail in the Examples. Also shown in FIG. 1 are restriction enzyme sites and sequences that regulate transcription.

In another embodiment, nucleic acid molecules of the present invention include a nucleic acid molecule encoding a Peptide-L-MHC$_{α+β}$ composition, wherein the sequence encoding the MHC class II α chain can be on the same or on a separate nucleic acid molecule as the sequence encoding an MHC class II β chain. For example, a nucleic acid molecule encoding a Peptide-L-MHC$_{α+β}$ composition can contain: a sequence encoding a MHC class I MHC$_α$-L-Peptide molecule ligated to a sequence encoding a β2m subunit; a sequence encoding an MHC class II MHC$_β$-L-Peptide molecule ligated to a sequence encoding an MHC class II α chain encoding sequence; or a sequence encoding an MHC class II MHC$_α$-L-Peptide molecule ligated to a sequence encoding an MHC class II β chain encoding sequence.

In other embodiments, a nucleic acid sequence is used that encodes for a signal or leader segment that is capable of promoting secretion of a Peptide-L-MHC molecule from the cell that produces the molecule. Nucleic acid sequences encoding the leader or signal segments are covalently associated (by base pair linkage) to the 5' end of a nucleic acid molecule. The leader or signal segments can be segments which naturally are associated with an MHC segment or are heterologous. Preferred segments are naturally associated segments. To obtain membrane-bound embodiments, nucleic acid sequences are used that contain at least one transmembrane segment capable of anchoring a Peptide-L-MHC molecule to a lipid-containing substrate, such segments including at least a portion of an MHC transmembrane domain and at least a portion of an MHC cytoplasmic domain. A nucleic acid sequence encoding a transmembrane segment is covalently associated (by base pair linkage) to the 3' end of a nucleic acid sequence encoding the extracellular portion of a Peptide-L-MHC molecule. The transmembrane segment can be a segment naturally associated with the MHC segment or heterologous. Preferred transmembrane segments include segments that are naturally associated with an MHC segment. A nucleic acid molecule encoding a Peptide-L-MHC capable of being membrane-bound contains at least one nucleic acid sequence encoding a segment ligated to the 3' end of an extracellular domain in a manner such that the transmembrane encoding sequence is transcribed in-frame.

Another embodiment of the present invention is a fusion protein that includes a Peptide-L-MHC molecule containing-domain attached to a fusion segment. Inclusion of a fusion segment as part of a Peptide-L-MHC molecule of the present invention can enhance the molecule's stability during production, storage and or use. Furthermore, a fusion segment can function as a tool to simplify purification of a Peptide-L-MHC molecule, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of the Peptide-L-MHC molecule. Linkages between fusion segments and Peptide-L-MHC molecule can be made to be susceptible to cleavage to enable straight-forward recovery of the Peptide-L-MHC molecules. Fusion proteins are preferably produced by culturing a recombinant cell transformed with a fusion nucleic acid sequence that encodes a protein including the fusion segment attached to either the carboxyl and or amino terminal end of a Peptide-L-MHC molecule.

Particularly preferred nucleic acid molecules include: N-IE$^{kd}$-MCC having sequences encoding a moth cytochrome C (91-103) peptide, a linker and an IEβ$^k$ protein (described in detail in Example 1); N-IA$^d$-OVA having sequences encoding the cOVA (327-339) peptide, a linker and an IAβ$^d$ protein (described in detail in Example 1); and N-IA$^b$-Ea having sequences encoding an IEα$^d$ (56-73) peptide, a linker and an IAβ$^b$ protein (described in detail in Example 2).

The present invention also includes a recombinant molecule comprising a nucleic acid sequence encoding a Peptide-L-MHC molecule operatively linked to a vector capable of being expressed in a host cell. As used herein, "operatively linked" refers to insertion of a nucleic acid sequence into an expression vector in such a manner that the sequence is capable of being expressed when transformed into a host cell. As used herein, an "expression vector" is an RNA or DNA vector capable of transforming a host cell and effecting expression of an appropriate nucleic acid sequence, preferably replicating within the host cell. An expression vector can be either prokaryotic or eukaryotic, and typically is a virus or a plasmid.

Recombinant molecules of the present invention include pIE$^{kd}$-MCC (described in detail in Example 1); pIA$^d$-OVA (described in detail in Example 1); pM12-IA$^b$-EA (described in detail in Example 2); and pFIB-IA$^b$-Ea (described in detail in Example 2).

Construction of desired expression vectors can be performed by methods known to those skilled in the art and expression can be in eukaryotic or prokaryotic systems. Procaryotic systems typically used are bacterial strains including, but not limited to various strains of *E. coli*, various strains of *bacilli* or various species of Pseudomonas. In prokaryotic systems, plasmids are used that contain replication sites and control sequences derived from a species compatible with a host cell. Control sequences can include, but are not limited to promoters, operators, enhancers, ribosome binding sites, and Shine-Dalgarno sequences. Expression systems useful in eukaryotic host cells comprise promoters derived from appropriate eukaryotic genes. Useful mammalian promoters include early and late promoters from SV40 or other viral promoters such as those derived from baculovirus, polyoma virus, adenovirus, bovine papilloma virus or avian sarcoma virus. Expression vectors of the present invention include any vectors that function (i.e., direct gene expression) in recombinant cells of the present invention including bacterial, yeast, other fungal, insect, and mammalian cells. Particularly preferred expression vectors of the present invention include dual promoter baculovirus transfer vectors, and vectors containing class II promoters, β-actin promoters, globin promoters, or epithelial cell specific promoters.

An expression system can be constructed from any of the foregoing control elements operatively linked to the nucleic acid sequences of the present invention using methods known to those of skill in the art. (see, for example, Sambrook et al., ibid.)

Host cells of the present invention can be: cells naturally capable of producing MHC protein; or cells that are capable of producing MHC protein when transfected with a nucleic acid molecule encoding an MHC protein. Host cells of the present invention include, but are not limited to bacterial, fungal, insect and mammalian cells. Suitable host cells include mammalian cells capable of stimulating a T cell response, preferably antigen presenting cells including dendritic cells, macrophages and B lymphocytes, as well as cells that are not capable of stimulating a T cell response, preferably fibroblasts, red blood cells, pluripotent progenitor cells, epithelial cells and neural cells.

One particular embodiment involves a host cell transformed with a recombinant molecule encoding a Peptide-L-MHC molecule, wherein the MHC segment of the molecule is a class II β chain. The host cell can also be co-transformed with a recombinant molecule encoding an MHC class II α chain capable of associating with the Peptide-L-MHC molecule to form a Peptide-L-MHC$_{α+β}$ composition.

In one aspect of the present invention, recombinant cells can be used to produce at least one Peptide-L-MHC molecule by culturing such cells under conditions effective to produce such molecules, and recovering the molecules. Effective conditions to produce a recombinant molecule include, but are not limited to appropriate culture media, bioreactor, temperature, pH and oxygen conditions. Depending on the expression vector used for production, resultant molecules can either remain within the recombinant cell, be retained on the outer surface of the recombinant cell, or be secreted into the culture medium. As used herein, the term "recovering the protein" refers to collecting the fermentation medium containing the protein and or recombinant cells. Recovery need not imply additional steps of separation or purification. Peptide-L-MHC molecules of the present invention can be purified using a variety of standard protein purification techniques such as, but not limited to affinity chromatography, ion exchange chromatography, filtration, centrifugation, electrophoresis, hydrophobic interaction chromatography, gel filtration chromatography, chromatofocusing and differential solubilization. Isolated Peptide-L-MHC molecules are preferably retrieved in "substantially pure" form. As used herein, "substantially pure" refers to a purity that allows for the effective use of the molecule as a heretofore described pharmaceutical composition or experimental reagent.

Soluble Peptide-L-MHC molecules of the present invention can be purified using, for example, immunoaffinity chromatography. Peptide-L-MHC molecules anchored in a lipid-containing substrate can be recovered by, for example, density gradient centrifugation techniques.

One aspect of the present invention relates to the use of Peptide-L-MHC molecules as formulations for therapeutic or experimental use. A Peptide-L-MHC molecule of the present invention can be used to produce a pharmaceutical reagent. Such pharmaceutical reagents are useful for administration to patients suffering from diseases such as autoimmune diseases, immunodeficiency diseases, and immunoproliferative diseases, or from graft-host rejection. A pharmaceutical reagent includes a Peptide-L-MHC molecule associated with a suitable carrier. A Peptide-L-MHC molecule of the present invention can also be used to produce an experimental reagent. An experimental reagent is a reagent useful for the development of drugs and for the study of different aspects of an immune response. An experimental reagent includes a Peptide-L-MHC molecule associated with a suitable carrier.

As used herein, a "carrier" refers to any substance suitable as a vehicle for delivering a molecule or composition to a suitable in vitro or in vivo site of action. As such, carriers can act as an excipient for formulation of a pharmaceutical or experimental reagent containing a Peptide-L-MHC molecule. Preferred carriers are capable of maintaining Peptide-L-MHC molecules in a form that is capable of being recognized by a T cell receptor. Examples of such carriers include, but are not limited to water, phosphate buffered saline, Ringer's solution, dextrose solution, serum-containing solutions, Hank's solution and other aqueous physiologically balanced solutions. Aqueous carriers can also contain suitable auxiliary substances required to approximate the physiological conditions of the recipient, for example, enhancement of chemical stability and isotonicity. Suitable auxiliary substances include, for example, sodium acetate, sodium chloride, sodium lactate, potassium chloride, calcium chloride, sorbitan monolaurate, triethanolamine oleate, and other substances used to produce phosphate buffer, Tris buffer, and bicarbonate buffer. Auxiliary substances can also include preservatives, such as thimerosal, m or o-cresol, formalin and benzyl alcohol. Preferred auxiliary substances for aerosol delivery include surfactant substances nontoxic to a recipient, for example, esters or partial esters of fatty acids containing from about 6 to about 22 carbon atoms. Examples of esters include, caproic, octanoic, lauric, palmitic, stearic, linoleic, linolenic, olesteric, and oleic acids. Formulations of the present invention can be sterilized by conventional methods and/or lyophilized.

Carriers of the present invention can also include adjuvants including, but not limited to, Freund's adjuvant; other bacterial cell wall components; aluminum-based salts; calcium-based salts; silica; polynucleotides; toxoids; serum proteins; viral coat proteins; and other bacterial-derived preparations.

Useful carriers for membrane-bound Peptide-L-MHC molecules include any artificial or natural lipid-containing substrate, preferably cells, cellular membranes, liposomes and micelles. Cellular carriers of the present invention include cells essentially incapable of stimulating T cells, such as cells that lack secondary proteins capable of mediating T cell activation, as well as cells that stimulate T cells and that have secondary proteins that mediate T cell activity. Preferred mammalian cells of the present invention include, but are not limited to antigen presenting cells, fibroblasts, red blood cells, pluripotent progenitor cells, epithelial cells, and neural cells. Antigen presenting cells are cells that typically express MHC proteins on their cell surface and that are capable of processing antigens. Preferred antigen presenting cells include, for example, dendritic cells, macrophages and B lymphocytes.

In one embodiment of the present invention, a membrane-bound Peptide-L-MHC molecule is attached to artificial and/or natural lipid-containing carriers to produce formulations capable of suppressing T cell activity. Without being bound by theory, it is believed that T cells require distinct signals for activation. One such signal is delivered through a TCR, following the receptor's binding with peptide presented in the context of MHC protein such as to a Peptide-L-MHC of the present invention. It is, however, believed that signaling through the TCR alone is insufficient to optimally activate a T cell. As such, the absence of a second signal from a surface protein other than the TCR can result in T cell suppression which herein refers to one of the following: (1) failure to activate the T cell; (2) induction of a T cell into an anergic state; or (3) killing of the T cell.

A variety of non-TCR proteins on the surface of a T cell can, in conjunction with Peptide-L-MHC molecule binding to TCR, mediate signal transduction resulting in T cell activation. An example of a non-TCR signal transduction protein is the T cell protein CD28. CD28 is believed to co-stimulate a T cell with TCR, resulting in T cell activation. CD28 is the receptor for the protein B7 which is found on antigen presenting cells. As such, it is believed that binding to TCR by an MHC-peptide complex and to CD28 by a B7 protein can result in T cell activation. Conversely, the absence of CD28 binding to B7 in the presence of TCR binding by a peptide-MHC complex, does not result in activation of a T cell.

Preferred lipid-containing carriers for formulations capable of suppressing T cell activity include, for example micelles, liposomes, cells and cellular membranes essentially incapable of stimulating a T cell response. More preferred carriers include mammalian cells, such as red blood cells, fibroblast cells, pluripotent progenitor cells, epithelial cells and neural cells.

In another embodiment, a membrane-bound Peptide-L-MHC molecule is used to produce formulations capable of stimulating T cell activity As used herein, T cell stimulation refers to the activation of a T cell resulting in biological function, such as IL-2 production or cytotoxic activity. Preferably, lipid-containing carriers, such as micelles, liposomes, cells and cellular membranes essentially capable of stimulating a T cell response, are used to produce formulations that are capable of stimulating T cell activity. More preferred carriers include mammalian antigen presenting cells, such as dendritic cells, macrophages and B lymphocytes.

In yet another embodiment, a soluble Peptide-L-MHC molecule is used to produce formulations capable of suppressing T cell activity. Preferred carriers for soluble Peptide-L-MHC molecules include physiologically balanced solutions, and a more preferred carrier is phosphate buffered saline.

Pharmaceutical reagents of the present invention can be administered to any animal, preferably to mammals, and even more preferably humans. Acceptable protocols to administer pharmaceutical formulations in an effective manner include individual dose size, number of doses, frequency of dose administration, and mode of administration. Modes of delivery can include any method compatible with prophylactic or treatment of a disease. Modes of delivery include, but are not limited to, parenteral, oral, intravenous, topical or local administration such as by aerosol or transdermally.

A pharmaceutical reagent of the present invention is useful for the treatment of any disease caused in part by abnormal stimulation or suppression of an immune response. Such diseases include autoimmune diseases, immunodeficiency diseases, and immunoproliferative diseases. A pharmaceutical reagent of the present invention is also useful for treatments involving the transplantation of organs and skin. Autoimmune diseases include, for example, systemic lupus, myasthenia gravis, rheumatoid arthritis, insulin dependent diabetes mellitus and experimental allergic encephalomyelitis. Immunodeficient diseases include, for example, human AIDs, hypogammaglobulinemia, DiGeorge Syndrome, chronic mucocutaneous candidiasis, GVH disease, combined immunodeficiency disease, Nezelof's Syndrome, episodic lymphopenia, and immunodeficiencies related to thymomas, eczema, thrombocytopenia, adenosine diaminase deficiency and dwarfism. Immunoproliferative diseases include, for example, lymphomas and leukemias. In addition, a pharmaceutical reagent of the present invention capable of stimulating a T cell response is useful for the treatment of specific disorders such as tumors, allergic responses and inflammation.

Pharmaceutical reagents containing soluble protein of the present invention and/or membrane-bound protein anchored in a lipid-containing substrate incapable of stimulating a T cell response, are particularly useful for the treatment of autoimmune diseases, immunoproliferative diseases and in transplantation procedures. Pharmaceutical reagents containing membrane-bound protein anchored in a lipid-containing substrate capable of stimulating a T cell response, are particularly useful for the treatment of immunodeficiency diseases.

Experimental reagents of the present invention includes a formulation useful for, for example, screening for peptides capable of regulating T cell activity, antibodies that bind MHC protein complexed with peptide, for TCR's capable of binding MHC protein complexed with peptide, and for T cells bearing TCR capable of binding MHC protein complexed to peptide.

A method to screen for peptides capable of regulating T cell activity includes: (1) contacting a T cell with a reagent selected from the group consisting of, (i) a Peptide-L-MHC molecule comprising an antigenic peptide joined by a linker to an MHC segment, wherein said MHC segment is capable of forming a binding groove, (ii) a formulation in which the Peptide-L-MHC molecule of (i) is anchored to the plasma membrane of a cell essentially incapable of stimulating a T cell response, and (iii) a formulation in which said Peptide-L-MHC molecule of (i) is anchored to the plasma membrane of a cell capable of stimulating a T cell response, wherein the T cell to be contacted is capable of recognizing the MHC segment of the reagent; and (2) determining if the id reagent stimulates IL-2 activity or alters signal transduction.

The following experimental results are provided for purposes of illustration and are not intended to limit the scope of the invention.

EXAMPLES

Example 1

This Example demonstrates that genes coding for peptides covalently associated to MHC Class II proteins by a linker can be expressed as stable soluble proteins capable of being recognized by T cells.

Murine class II genes encoding the extracellular domains of an IE α chain protein (IEα$^d$), an IE β chain protein (IEβ$^k$), IA α chain protein (IAα$^d$), and an IA β chain (IAβ$^d$) protein, were prepared using polymerase chain reaction (PCR) amplification of cloned cDNA templates. To allow for secretion of fully assembled αβ dimers, these genes were truncated at the last codon prior to codons encoding the transmembrane and cytoplasmic portions of the proteins. Primers used for PCR amplification of the IEα$^d$ gene were 5' TCCTCGAGAAATGGCCACAATTGGAG 3' (SEQ ID NO:9) and 3' CTTTGATTTCTCTTAATTCCATGGTT 5' (SEQ ID NO: 10). Primers used for PCR amplification of the IEβ$^k$ gene were 5' CCGGGAATTCAGCATGGTGTG-GCTCC 3' (SEQ ID NO:11) and 3' AGACGTTCTTGTTG-CATTCGTACGCC 5' (SEQ ID NO:12). The alignment of the primers with their respective cDNA templates is shown in Table 1 (SEQ ID NO:9, SEQ ID NO:10, SEQ ID NO:11, SEQ ID NO:12, SEQ ID NO:13, SEQ ID NO:14, SEQ ID NO:15, and SEQ ID NO:16).

Genes encoding IAα$^d$ and IAβ$^d$ proteins were also produced by PCR amplification. Primers used for PCR amplification of the IAα$^d$ gene were 5' TCCTCGAGAGGATGC-CGTGCAGCAGAG 3' (SEQ ID NO:13)and 3' CTCGACTGGTCTTTGAATTCCATGGTT 5' (SEQ ID NO:14) Primers used for PCR amplification of the IAβ$^d$ gene were 5' TACGGAATTCTTAGAGATGGCTCTG-CAGA 3' (SEQ ID NO:15) and 3' TCAGACGGGCCTCGT-TCATTCGTACGCC 5' (SEQ ID NO:16). The alignment of the primers with their respective cDNA templates is shown in Table 1 (SEQ ID NO:9, SEQ ID NO:10, SEQ ID NO:11, SEQ ID NO:12, SEQ ID NO:13, SEQ ID NO:14, SEQ ID NO:15 and SEQ ID NO:16). The restriction enzyme sites used for cloning the IEα$^d$, IEβ$^k$, IAα$^d$ and IAβ$^d$ genes into new multiple cloning sites (MCS) of a baculovirus transfer vector are also shown in Table 1 (SEQ ID NO:9, SEQ ID NO:10, SEQ ID NO:11, SEQ ID NO:12, SEQ ID NO:13, SEQ ID NO:14, SEQ ID NO:15, and SEQ ID NO:16).

TABLE 1

```
          5'-TCCTCGAGAAATGGCCACAATTGGAG-3'
Eα^d        XhoI      MetAlaThrIleGlyAlaLeu//LeuLeuProGluThrLysGluAsn***  KpnI
                                                   3'-CTTTGATTTCTCTTAATTCCATGGTT-5'

5'CCGGGAATTCAGCATGGTGTGGCTCC-3'
Eβ^k         EcoRI    MetValTrpLeuProArg//GLnSerThrSerAlaGlnAsnLys***  SphI
                                                   3'-AGACGTTCTTGTTFCATTCGTACGCC-5'

5'-TCCTCGAGAGGATGCCGTGCAGCAGAG-3'
Aα^d        XhoI      MetProCysSerArgAlaLeu//ProMetSerGluLeuThrGluThr***  KpnI
                                                   3'-CTCGACTGGTCTTTGAATTCCATGGTT-5'

5'-TACGGAATTCTTAGAGATGGCTCTGCAGA-3'
Aβ^d         EcoRI    MetAlaLeuGInIleProSer//GlnSerGluSerAlaArgSerLys***SphI
                                                   3'-TCAGACGGGCCTCGTTCATTCGTACGCC-5'
```

Using PCR amplification, a hybrid IEβ$^k$ nucleic acid molecule was produced containing sequences encoding amino acid residues 91-103 of moth cytochrome c (MCC Peptide (91-103), a linker containing a thrombin cleavage site, and the IEβ$^k$ gene. The hybrid molecule was prepared as follows. Referring to Table 2 (SEQ ID NO:19 and SEQ ID NO:20), a first fragment (fragment 234-328) was produced encoding the leader and the first three codons of the β1 domain of IEβ$^k$, and the first 11 codons of the MCC peptide using Primer #234 (5' TACGGAATTCAGCATG-GTGTGGCTCCC 3') (SEQ ID NO:17) and Primer #328 (5' A C C G G A C G A A G T T T A T C C G T T A G T C - CAGTCGGGCCCTCAGAGACTGGTT 3') (SEQ ID NO:18) on an IEβ$^k$ cDNA template. Primer #234 (SEQ ID NO:17)contains an EcoRI

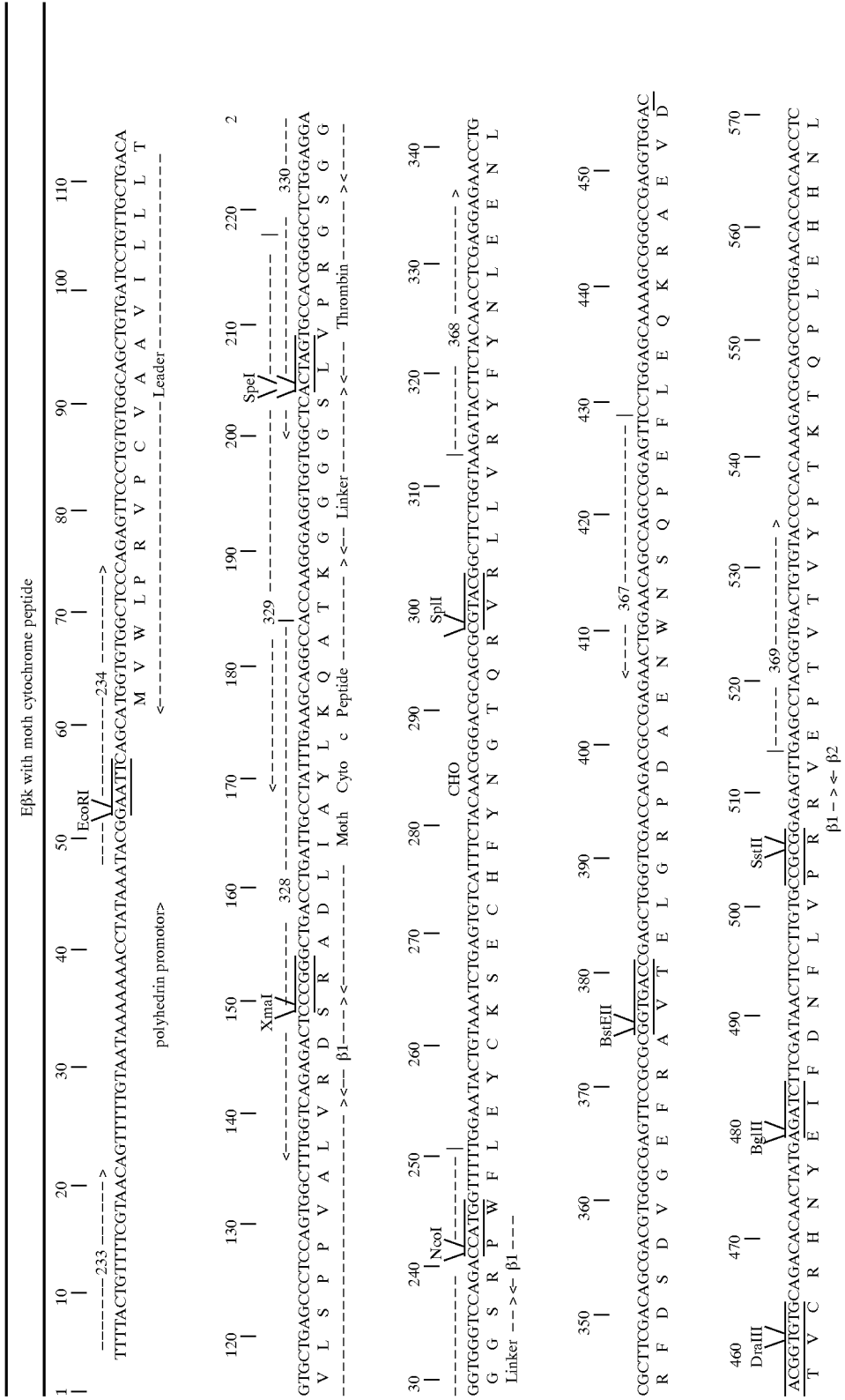

TABLE 2-continued

Eβk with moth cytochrome peptide

```
      580       590       600       610       620       630       640       650       660       670       680
       |         |         |         |         |         |         |         |         |         |         |
CTGGTCTGCTCTGTGAGTGACTTCTACCCTGGCAACATTGAAGTCAGAGTGTGGTTCCGGAATGGCAAGGAGGAGAAAACAGGAATTGTGTCCACGGGCCTGGTCGAAATGGAGAC
 L   V   C   S   V   S   D   F   Y   P   G   N   I   E   V   R   W   F   R   N   G   K   E   E   K   T   G   I   V   S   T   G   L   V   R   N   G   D
                                                             <----- 374 ------|

690       700       710       720       730       740       750       760       770       780       790
       |         |         |         |         |         |         |         |         |         |         |
TGGACCTTCCAGACACTGTGATGCTGGAGACGGTTCCTCAGAGTGGAGAGGTTTACACCTGCCAGGTGGAGCATCCAGCCTGACCGACCCTGTCACGGTCGAGTGGAAAGCA
 W   T   F   Q   T   F   L   V   M   L   E   T   V   P   Q   S   G   E   V   Y   T   C   Q   V   E   H   P   S   L   T   D   P   V   T   V   E   W   K   A
                  |------ 371 ------>

800       810       820       830       840       850       860       870       880       890
       |         |         |         |         |         |         |         |         |         |
CAGTCCACATCTGCACAGAACAAGTAAGCATGCGGGGATCCGGTTATTAGTACATTTATTAAGCGCTAGATTCTGTGCGTTGTTGATTTACA
 Q   S   T   S   A   Q   N   K   *                                                                SphI
 <------ 221 ------|                                                             <---- 232 ---|
 ------ β2 ------>
``` restriction enzyme site and Primer #328 (SEQ ID NO:18) contains an XmaI restriction enzyme site. Fragment 234-328 was used as a template for a second PCR fragment (fragment 234-329) in which fragment 234-328 was extended by adding sequences encoding the remainder of the MCC peptide and the first 10 codons of the linker were added using Primer #329 (5' GGGGCACCGTGATCACTCG-GTGGTGGAGGGAACCACCGGACGAAGTTTAT 3') (SEQ ID NO:22). Primer #329 (SEQ ID NO:22) contains an SpeI site. Fragment 234-329 was used as a template for a third PCR fragment (fragment 234-330) in which fragment 234-329 was extended by adding sequences encoding the remainder of the linker and residues 4-8 of the β1 domain using Primer #330 (5' TTTTTGGTACCAGACCTGGGTG-GAGGAGGTCTCGGGGCACCGTGATCACTCG 3')(SEQ ID NO:22). Primer #330 (SEQ ID NO:22) contains a SpeI site and an NcoI site. Fragment 234-330 was then digested with EcoRI and NcoI and cloned into EcoRI and NcoI digested pBACp1OH vector that had the IEα$^d$ cloned after the P10 promoter and IEβ$^k$ cloned after the polyhedrin promoter (described in detail below). The nucleic acid molecule having sequences encoding a moth cytochrome C (91-103) peptide, a linker and an IEβ$^k$ gene encoding the IEβ$^k$ β1 and β2 domains is referred to as N-IE$^{kd}$-MCC.

Using PCR amplification, a hybrid IAβ$^d$ nucleic acid molecule was produced containing sequences encoding amino acid residues 327-339 of chicken ovalbumin (cOVA Peptide (327-339), a linker containing a thrombin cleavage site, and the IAβ$^d$ gene. The hybrid molecule was prepared as follows. Referring to Table 3(SEQ ID NO:25 and SEQ ID NO:26), a first fragment (fragment 261-331) was produced encoding the leader and the first 3 codons of the β1 domain of IAβ$^d$ and the first 7 codons of the cOVA peptide using Primer #261 (5' TACGGAATTCTTAGAGATGGCTCTG-CAGAT 3')(SEQ ID NO:23) and Primer #331 (5' A G A G T C G T A C C C G T C G T A C A T G C C T - CAAAGGCGGGAGTCAGGGCCCCGACGAGT 3') (SEQ ID NO:24) on an IAβ$^d$ cDNA template. Primer #261 (SEQ ID NO:23) contains an EcoRI

TABLE 3

Aβd with Chicken Ovalbumin peptide

```
1         10        20        30        40        50        60        70        80        90        100       110
|         |         |         |         |         |         |         |         |         |         |         |
TTTTACTGTTTTCGTAACAGTTTTGTAATAAAAACCTATAAATACGGAATTCTTAGAGATCTGCAGATCCCAGCCTCCTCTCAGCTGCTGTGTGGTGCTGATG
<----- 233 ----->                                   |---- EcoRI
                                                    |---- 261 ----------->
                                                                                      M  A  L  Q  I  P  S  L  L  L  S  A  A  V  V  V  L  M
                                                                                      <----- Leader -----

120       130       140       150       160       170       180       190       200       210       220
|         |         |         |         |         |         |         |         |         |         |
GTGCTGAGCAGCCCGGACTGAGGGCGAAACTCCGTACATGCTGGAAGCAATGAGGCTGGCAGAGAGGTGGGGGCTGGGGGCTCTGAGGTGCCCGAGGCTCTGAGGT
        |---- XmaI                              >  <--- β1 ---->                                  |---- SpeI
        |---- 331 ----------->                                                                    |---- 333 -----
                                                                                                   <---Thrombin--><---
  V  L  S  S  P  G  T  E  G  G  G  N  S  V  H  A  A  E  I  N  E  A  G  R  G  G  G  S  L  V  P  R  G  S  G  G
                              <---- cOVA Peptide ----->                           <----- Linker ----->

230       240       250       260       270       280       290       300       310       320       330       340
|         |         |         |         |         |         |         |         |         |         |         |
GGAGGCTCCGAAAGGCATTTCGTGGTCCAGTTCAAGGGCGAGTGCTACTACCAAGGGACGCAGCGCATACGGCTCGTGACCAGATACATCTACAACCGGGAGGAGTACGTG
                                                                                        <--- Sheet 2 ----->
  G  G  S  E  R  H  F  V  V  Q  F  K  G  E  C  Y  Y  T  N  G  T  Q  R  I  R  L  V  T  R  Y  I  Y  N  R  E  E  Y  V
  Linker ---><---- β1 ---- >                        <---- CHO ---->

350       360       370       380       390       400       410       420       430       440       450
|         |         |         |         |         |         |         |         |         |         |
CGCTACGACAGCGACGTGGGCGAGTACCGCGCGGTGACCGAGCTGGGGCGGCCAGACGCCGAGTACTGGAACAGCCAGCCGGAGATCCTGGAGCGAACGGGCCGAGGTGGAC
                               |--- BstEII
                               |---- 270 ----->
  R  Y  D  S  D  V  G  E  Y  R  A  V  T  E  L  G  R  P  D  A  E  Y  W  N  S  Q  P  E  I  L  E  R  T  R  A  E  V  D
                               <- Sheet 4 ->                                            <----- Helix ----->

460       470       480       490       500       510       520       530       540       550       560       570
|         |         |         |         |         |         |         |         |         |         |         |
ACGGCGTGCAGACAACTACGAGGGCCCGAGACCAGCACCTCCCTGCGGCGGCTTGAACAGCCAATGTGCAGCCCATTCCCTGTCCAGGACAGGCCCTCAACCACCACAAC
  |--- Dra III                                                               (EcoNI)
                                                                              |---- 272 ----->
                                                                        <---- 271 ---->
  T  A  C  R  H  N  Y  E  G  P  E  T  S  T  S  L  R  R  L  E  Q  P  N  V  A  I  S  L  S  R  T  E  A  L  N  H  H  N
  <---- Sheet 3 ---->                        <------- Helix -------->  <-- β2 -->              <----- Helix -----
```

TABLE 3-continued

Aβd with Chicken Ovalbumin peptide

```
     580         590         600         610         620         630         640         650         660         670         680
      |           |           |           |           |           |           |           |           |           |           |
ACTCTGGTCTGTTCGGTGACAGATTTCTACCCAGCCAAGATCAAAGTGCGCTGGTTCAGGAATGGCCAGGAGACAGTGGGGTCTCATCCACACAGCTTATTAGGAATGGG
 T  L  V  C  S  V  T  D  F  Y  P  A  K  I  K  V  R  W  F  R  N  G  Q  E  E  T  V  G  V  S  S  T  Q  L  I  R  N  G 690         700         710         720         730         740         750         760         770         780         790
      |           |           |           |           |           |           |           |           |           |      BstXI |
                                                                                                                           \/
GACTCGACCTTCCAGGTCCTGGTCATGGAGATGACCCCTCATCAGGGAGAGGTCTACACCTGCCATGTGGAGCATCCAGCCTGAAGAGCCCATCACTGTGGAGTGGAGG
 D  W  T  F  Q  V  L  V  M  L  E  M  T  P  H  Q  G  E  V  Y  T  C  H  V  E  H  P  S  L  K  S  P  I  T  V  E  W  R 800         810         820         830         840         850         860         870         880         890
      |           |           |      SphI |           |           |           |           |           |           |
                                       \/
GCACAGTCCGAGTCTGCCCGAGCAAGTAAGCATGCGGGGATCCGGTTATTAGTACATTTATTAATTAAGCGCTAGAATTCTGTGCGTTGTTGATTTTACA
 A  Q  S  E  S  A  R  S  K  *
       <----- 259 -----> <----- 232 ----->
       <--- β2 --->
``` site and Primer #331 (SEQ ID NO:24)contains an XmaI site. Fragment 261-331 was used as a template for a second PCR fragment (fragment 261-332) in which the fragment 261-331 was extended by adding sequences encoding the remainder of the cOVA peptide and the first 8 codons of the linker were added using Primer #332 (5' CCGTGAT-CACTCGGGGGTGGAGGAGACGGTCGGAG-TAACTAGAGTCGTACCCGTC 3')(SEQ ID NO:27). Primer #332 (SEQ ID NO:27) contains an SpeI site.

Using PCR amplification, a third fragment (fragment 333-259) was produced which containing sequences encoding the IA$\beta^d$ β1 domain (minus the first three codons) and a portion of the IA$\beta^d$ β2 domain. Fragment 333-259 was produced using Primer #333 (5' GGCTCACTAGTGC-CCCGAGGCTCTGGAGGTGGAGGCTC-CGAAAGGCATTTC 3')(SEQ ID NO:28) and Primer #259 (5' GGCGTACGAACGAATGAACGAGGCCCGTCTGAG 3')(SEQ ID NO:29) on an IA$\beta^d$ cDNA template. Primer #333 (SEQ ID NO:28) contains an SpeI site and Primer #259 (SEQ ID NO:29) contains an SphI site.

Fragment 261-332 and fragment 333-259 were mixed in solution and used as PCR templates for Primer #261 (SEQ ID NO:23) and Primer #259 (SEQ ID NO:29) to form fragment 261-259 encoding the IA$\beta^d$ leader, the cOVA peptide, the linker and the IA$\beta^d$ protein. Fragment 261-259 was digested with EcoRI and SphI and cloned after the polyhedrin promoter of a pBACp1OH vector which had the IA$\alpha^d$ gene already cloned after the P10 promoter (described in detail below). The nucleic acid molecule having sequences encoding the cOVA (327-339) peptide, a linker and an IA$\beta^d$ protein including the β1 and β2 domains is referred to as N-IA$^d$-OVA.

Table 4 (SEQ ID NO:30 and SEQ ID NO:31; SEQ ID NO:32 and SEQ ID NO:33) lists the nucleic acid and protein sequences of the IE$\beta^k$-MCC and IA$\beta^d$-OVA from the promoters (described below), through the leaders, peptides and linkers, and into the β1 domains. Similar sequences are shown for IE$\beta^k$ or IA$\beta^d$ without nucleic acid sequences encoding antigenic peptide or linker.

TABLE 4

IE$\beta^k$

TTTTACTGTTTTCGTAACAGTTTTGTAATAAAAAAACCTATAAATACGGAATTCAGCATGGTGTGGCTCCCCAGAGTTCCCTGT
                                                                Met Val Trp Leu Pro Arg Val Pro Cys
————————————————    polyhedrin promoter    ————————>Eco RI    <——————————————————————

GTGGCAGCTGTGATCCTGTTGCTGACAGTGCTGAGCCCTCCAGTGGCTTTGGTCAGAGACTCCAGACCATGGTTTTTGGAATAC
Val Ala Ala Val Ile Leu Leu Leu Thr Val Leu Ser Pro Pro Val Ala Leu Val Arg Asp Ser Arg Pro Trp Phe Leu Glu Tyr
——— Leader      ————————————————————————————————————————><——————————————E$\beta^k$(β1)    ——————

Moth Cyto C Peptide Covalently Linked to IE$_\beta^k$

*TTTTACTGTTTTCGTAACAGTTTTGTAATAAAAAAACCTATAAATACGGAATTCAGCATGGTGTGGCTCCCCAGAGTTCCCTGT
                                                                Met Val Trp Leu Pro Arg Val Pro Cys
————————————————    polyhedrin promoter    ————————>Eco RI    <——————————————————————

GTGGCAGCTGTGATCCTGTTGCTGACAGTGCTGAGCCCTCCAGTGGCTTTGGTCAGAGACTCCCGGGCTGACCTGATTGCCTAT
Val Ala Ala Val Ile Leu Leu Leu Thr Val Leu Ser Pro Pro Val Ala Leu Val Arg Asp Ser Arg Ala Asp Leu Ile Ala Tyr
——— Leader      ————————————————————————————————————————>< E$\beta^k$(β1) ><——————— Moth Cyto C TTGAAGCAGGCCACCAAGGGAGGTGGTGGCTCACTAGTGCCACGGGGCTCTGGAGGAGGTGGGTCCAGACCATGGTTTTTGGAA
Leu Lys Gln Ala Thr Lys Gly Gly Gly Gly Ser Leu Val Pro Arg Gly Ser Gly Gly Gly Gly Ser Arg Pro Trp Phe Leu Glu
   Peptide     (91–103)    ><—— Linker    ———><——— Thrombin ———><——— Linker    ———><——— E$\beta^k$(β1)    ——————

IA$_\beta^d$

TTTTACTGTTTTCGTAACAGTTTTGTAATAAAAAAACCTATAAATACGGAATTCTTAGAGATGGCTCTGCAGATCCCCAGCCTC
                                                                Met Ala Leu Gln Ile Pro Ser Leu
————————————————    polyhedrin promoter    ————————>Eco RI    <——————————————————————

CTCCTCTCAGCTGCTGTGGTGGTGCTGATGGTGCTGAGCAGCCCAGGGACTGAGGGCGGAAACTCCGAAAGGCATTTCGTGGTC
Leu Leu Ser Ala Ala Val Val Val Leu Met Val Leu Ser Ser Pro Gly Thr GLu Gly GLy Asn Ser Glu Arg His Phe Val Val
—————— Leader    ——————————————————————————————————————————><—————————— A$\beta^d$(β1)    ——————— cOVA Peptide Covalently Linked to IA$_\beta^d$

TTTTACTGTTTTCGTAACAGTTTTGTAATAAAAAAACCTATAAATACGGAATTCTTAGAGATGGCTCTGCAGATCCCCAGCCTC
                                                                Met Ala Leu Gln Ile Pro Ser Leu
————————————————    polyhedrin promoter    ————————>Eco RI    <——————————————————————

CTCCTCTCAGCTGCTGTGGTGGTGCTGATGGTGCTGAGCAGCCCCGGGACTGAGGGCGGAAACTCGTACATGCTGCCCATGCT
 Leu Leu Ser Ala Ala Val Val Val Leu Met Val Leu Ser Ser Pro Gly Thr GLu Gly Gly Asn SerVal His Ala Ala His Ala
 —————— Leader    ————————————————————————————————————————————><A$\beta^d$(β1)   ><——————————— cOVA
GAGATCATCGAGGCTGGCAGAGGAGGTGGAGGCTCACTAGTGCCCCGAGGCTCTGGAGGTGGAGGCTCCGAAAGGCATTTCGTG
Glu Ile Asn Glu Ala Gly Arg Gly Gly Gly Gly Ser Leu Val Pro Arg Gly Ser Gly Gly Gly Gly Ser Glu Arg His Phe Val
    Peptide (327–339)    ——><—— Linker    ———><——— Thrombin    ———><—— Linker    ———><—— A$\beta^d$(β1)    ———

The nucleic acid sequences encoding the α and β chains of IE and IA (IE$\alpha^d$, IE$\beta^k$, IE$\beta^k$-MCC, IA$\alpha^d$, IA$\beta^d$, and IA$\beta^d$-OVA sequences) were cloned into the P10 and polyhedrin MCS's of the dual promoter baculovirus transfer vector, pBACp1OH (Pharmingen). The vector was altered using oligonucleotides and PCR amplification to replace both the EcoRI and BglII sites after the PIO promoter and the BamHI site after the polyhedrin promoter with new MCS's. The DNA sequences through the new MCS's were:

```
                    XhoI      BstEII      MroI      KpnI
P10-    CACTGATCCTCGAGGGGGTGACCGGTCCGGAGGGGTACCAATTCCAG  (SEQ ID NO:34)

EcoRI    SalI    BglII    SphI    BamHI
Polyhedrin-AAATACGGAATTCGGGTCGACGGAGATCTGGGCATGCGGGGATCCGG  (SEQ ID NO:35)
```

To form the recombinant molecule pIE$^{kd}$-MCC encoding an IE$^{kd}$ αβ dimer containing the MCC peptide and the linker, the gene encoding the IEα$^d$ protein was ligated into the XhoI and KpnI sites following the P10 promoter, and the IEβ$^k$-MCC nucleic acid molecule was ligated into the EcoRI and NcoI sites after the polyhedrin promoter. The same procedure was performed to ligate the gene encoding the IEβ$^k$ protein into pBACp1OPH to form the recombinant molecule pIE$^{kd}$ encoding an IE$^{kd}$ αβ dimer.

To form the recombinant molecule pIA$^d$-OVA encoding an IA$^d$ αβ dimer containing the cOVA peptide and the linker, the gene encoding the IAα$^d$ protein was ligated into the EcoRI and SphI sites after the polyhedrin promoter and the IAβ$^d$-OVA nucleic acid molecule was ligated into the EcoRI and SphI sites after the polyhedrin promoter. The same procedure was used to ligate the gene encoding the IAβ$^d$ protein into pBACp1OPH to form the recombinant molecule P-IA$^d$ encoding an IA$^d$ αβ dimer. pIE$^{kd}$-MCC, pIE$^{kd}$, pIA$^d$-OVA and pIA$^d$ were separately recombined into the Baculogold baculovirus (Pharmingen) in SF9 cells by co-transfection to produce recombinant stocks of virus. The initial recombinant virus stocks were cloned by infection of SF9 cells at limiting dilution in 96-well plates. A large viral stock of a clone was produced for subsequent large scale protein production of secreted IE$^{kd}$MCC, IE$^{kd}$, IA$^d$-OVA and IA$^d$ protein.

Recombinant viral stocks containing pIE$^{kd}$-MCC, pIE$^{kd}$, pIA$^d$-OVA and pIA$^d$ recombinant molecules were expressed in baculovirus infected insect cells to produce secreted protein. High 5 insect cells (Invitrogen) at 5–10×10$^5$/ml in TMN-FH media were infected at a multiplicity of infection of 5–10 with baculovirus carrying pIE$^{kd}$, pIA$^d$, pIE$^{k/d}$-MCC, or pIA$^d$-OVA recombinant molecules. Five to six days later culture supernatants were harvested by centrifugation.

The secreted proteins were immunoaffinity purified using immobilized anti-β-chain monoclonal antibodies (14-4-4 specific for IEβ$^k$, and M5/114 specific for IAβ$^d$). The protein was eluted with a basic buffer at pH 10.5 and immediately neutralized. SDS-PAGE analysis was performed to measure relative amounts of protein recovery. The results showed in all cases equimolar α and β-chain in the eluted protein indicating initial secretion of αβ heterodimers. The overall yield was 0.5 to 1.5mg/liter of culture media.

Figure 2A:
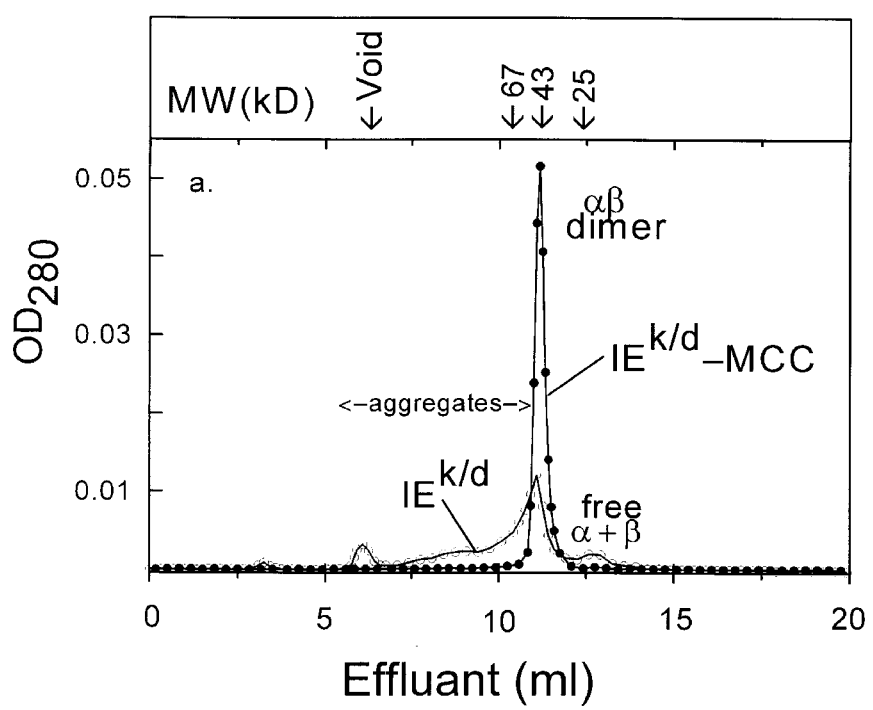
FIG. 2 illustrates the stabilization of soluble MHC class II molecules by covalently attached peptides.
Figure 2B:
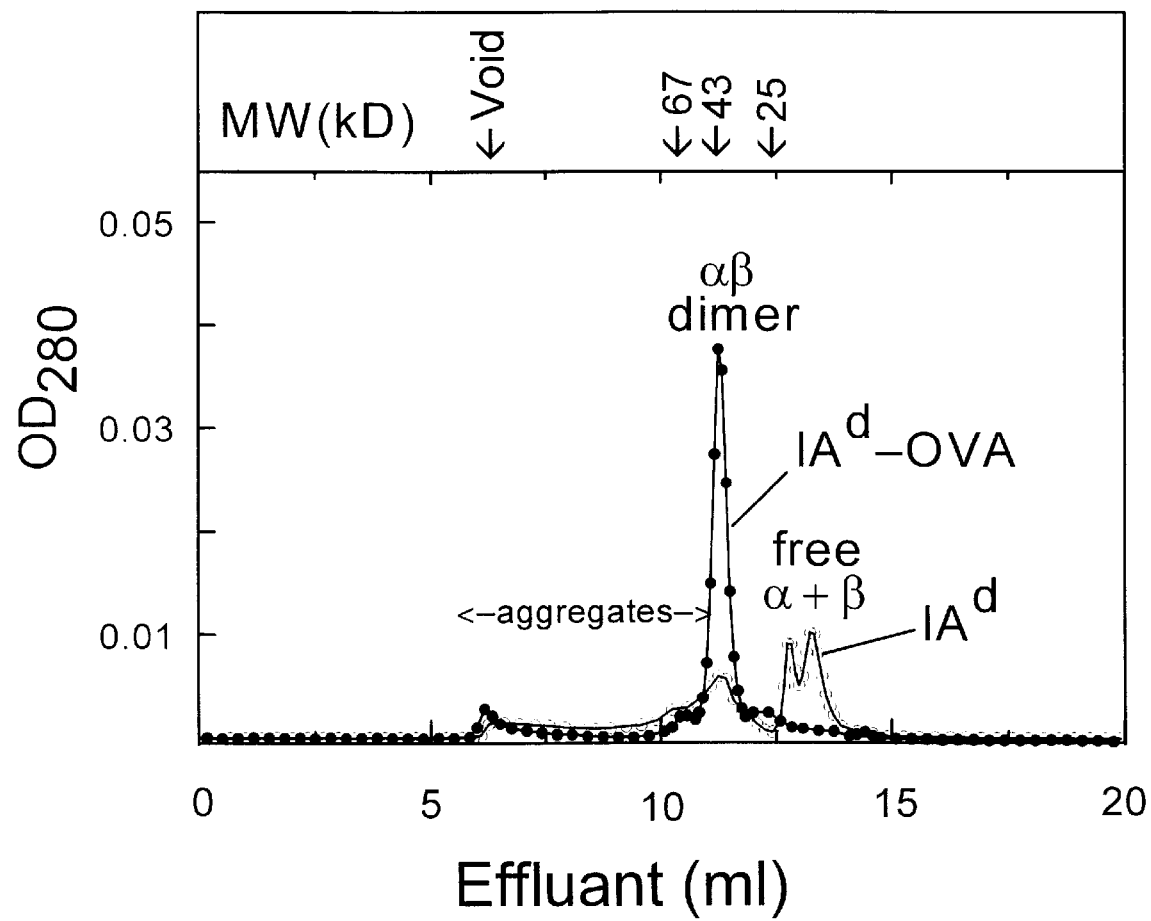

The stability of the immunoaffinity purified αβ dimers were analyzed by HPLC gel filtration. For gel filtration analysis, ~50ug of each protein in 20ul was loaded on a Shodex Protein KW-804 HPLC gel filtration column of dimensions 8mm×300mm (total volume ~15ml). The column was eluted at 0.5ml/min. in PBS and the OD$_{280}$ of the eluate followed. The four elution profiles shown were normalized to the same total OD$_{280}$. Referring to FIG. 2, the elution positions of molecular weight standards are shown at the top of the Figure: bovine serum albumin, 67kD; ovalbumin, 43kD; and chymotypsinogen, 25kD. In FIG. 2a, IE$^{dk}$ is represented as ○--○; IE$^{k/d}$-MCC is represented as ●--●. In FIG. 2b, IA$^d$ is represented as ○--○; and IA$^d$-OVA is represented as ●--●

The results shown in FIG. 2b indicate that both IE$^{k/d}$ and IA$^d$ protein showed high molecular weight aggregates and apparent size heterogeneity even in the αβ dimer peak. IA$^d$ appeared particularly unstable with considerable dissociation by free α and β chains after elution from the immunoaffinity column. The lack of stability of the IE$^{k/d}$ and IA$^d$ proteins is believed to be, in large part due to the lack of antigenic peptide bound to the binding groove of the two proteins.

In contrast, IE$^{k/d}$-MCC protein was greatly stabilized by the covalently attached MCC peptide, migrating sharply as a uniform αβ heterodimer (see FIG. 2a). Likewise, although IA$^d$-OVA still formed some high molecular weight aggregates, it also was considerably stabilized by the covalently attached OVA peptide with most of the protein migrating as a uniform αβ heterodimer. This stabilization suggests that the peptides were engaged by the peptide binding grooves of IE$^{kd}$-MCC and IA$^d$-OVA protein. Results from this experiment indicate that both IE$^{k/d}$-MCC and IA$^d$-OVA protein have peptide bound to their binding grooves and that both proteins are stable than IE$^{kd}$ and IA$^d$ proteins which do not have peptide bound their binding grooves.

The stability of MHC protein interaction with peptide was also measured by incubating IE$^{k/d}$-MCC and IA$^d$-OVA protein in 1% SDS at room temperature or 94° C. When the IE$^{k/d}$-MCC protein was tested in this manner, its chains remained associated at room temperature, but not at 94° C. In contrast, the IA$^d$-OVA α and β chains dissociated at both temperatures. These results suggest that peptide alone is sufficient to stabilize the IE$^{k/d}$-MCC protein in 1% SDS. However, peptide is not sufficient to stabilize the IA$^d$-OVA protein, perhaps due to the absence of the α and β-chain transmembrane regions.

The IE$^{k/d}$-MCC and IA$^d$-OVA protein were then tested for their ability to present peptide, by measuring IL-2 production by T cell hybridomas following incubation with immobilized IE$^{k/d}$-MCC and IA$^d$-OVA protein. Immunoaffinity purified IE$^{dk}$, IA$^d$, IEdk-MCC, and IA$^d$-OVA were prepared as described above. In addition, an attempt was made to produce IE$^{dk}$ and IA$^d$ MHC-peptide complexes by mixing: (1) synthetically produced MCC (88-103) peptide mixed with Ie$^{dk}$ protein (IE$^{dk}$+MCC); and (2) synthetically produced OVA (327-339) was mixed with IA$^d$ protein (IA$^d$+OVA). The mixtures were incubated overnight in 50 μl of citrate buffer at pH 5.0, at 37° C. and at a concentration of 10 μg of the Class II molecules and 10 μg of the peptide. Following incubation, the mixtures were neutralized and unbound peptide was removed using a Centricon 10 filter unit.

Figure 3A:
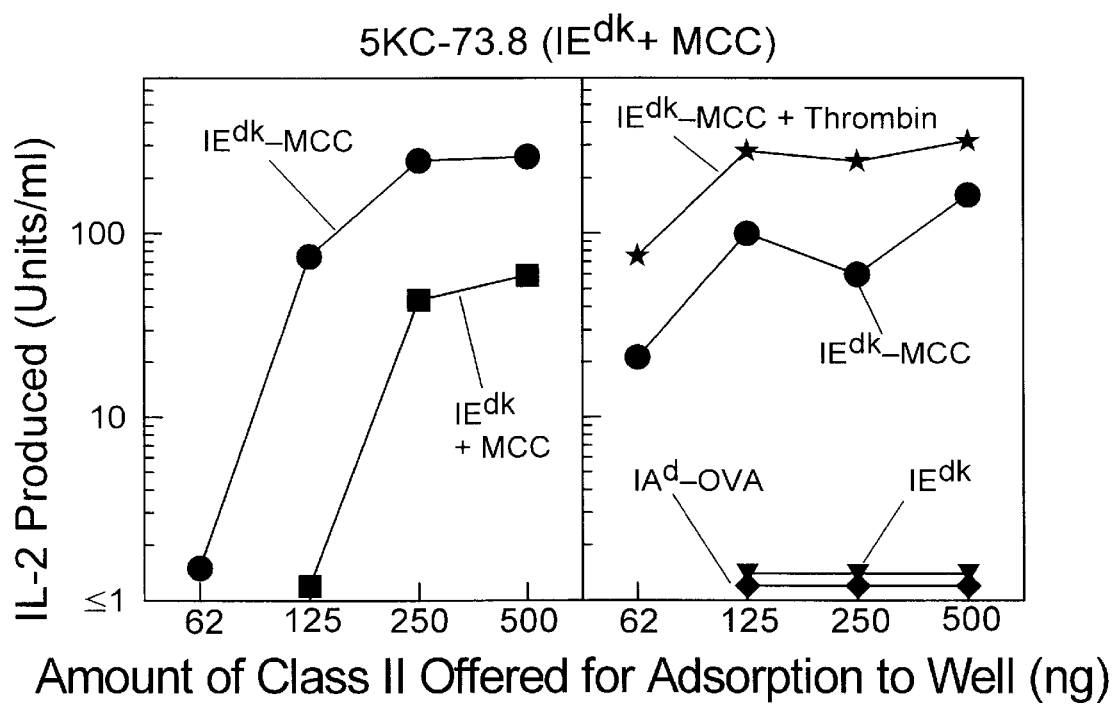
FIG. 3 illustrates the stimulation of T cell hybridomas by purified, immobilized class II protein bound by an antigenic peptide by a linker.

Aliquots of the IE$^{k/d}$-MCC and IA$^d$-OVA protein were digested by a 2 hour incubation of 10 μg of the complex with 2×10$^{-3}$ units of thrombin at pH 6.6. Such conditions digested at least 80% of the complex as assessed by SDS-PAGE. Different amounts of the various Class II preparations were immobilized by overnight non-specific adsorption to the bottom of wells of 96 well Immulon II plates. Either 5KC-73.8 (IE$^{dk}$+MCC specific) (5KC) or DO-11.10 (IA$^d$+OVA specific) T cell hybridomas (10$^5$ cells) were added in 250ul of tissue culture medium to each coated well of the 96-well plate. The plates were cultured overnight and the amount of IL-2 produced by the hybridomas was assessed. The results are shown in FIG. 3. FIG. 3a shows the results of IL-2 production by 5KC-73.8 cells in the presence of IE$^{dk}$-MCC (●, Ie$^{dk}$+MCC (■), thrombin treated IE$^{dk}$-MCC (★), and IE$^{dk}$ (▼) and IA$^d$-OVA (♦) samples as controls. The results indicate that the hybridoma responded better to the covalent IE$^{dk}$-MCC complex than to purified IE$^{dk}$ subsequently loaded with the MCC peptide (IE$^{dk}$+MCC). In addition, cleavage of the linker by thrombin did not affect the ability of the IE$^{dk}$-MCC complex to induce IL-2 production.

Figure 3B:
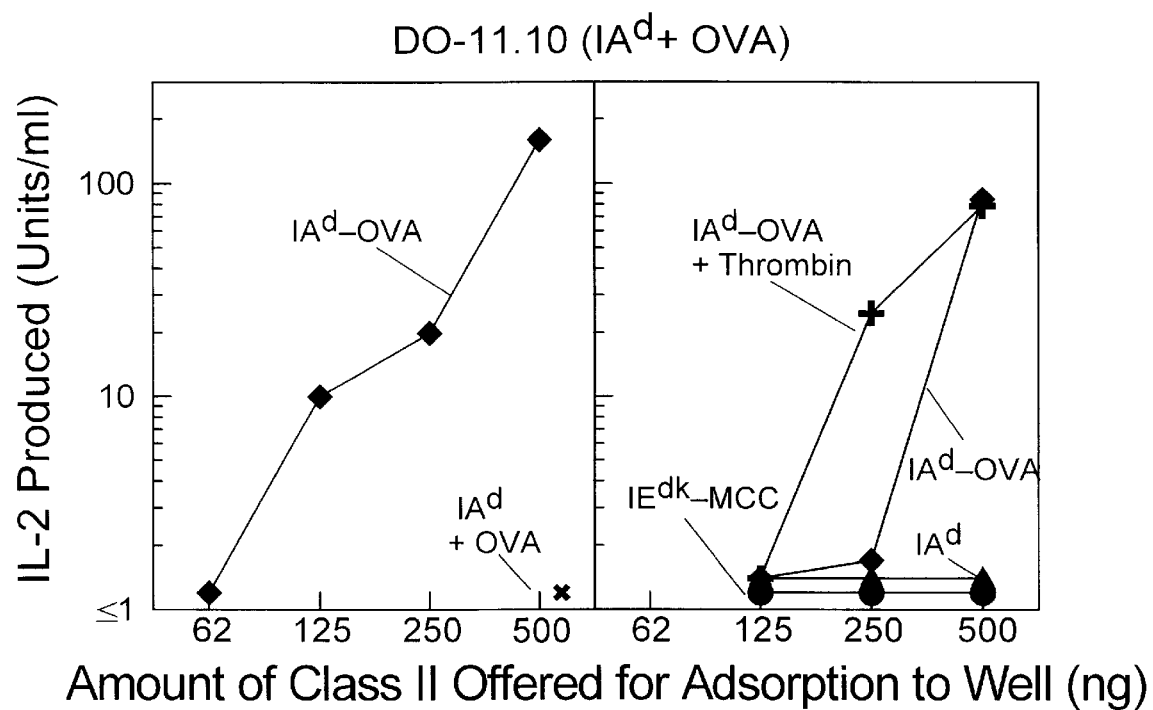

FIG. 3b shows the results of IL-2 production by DO-11.10 cells in the presence of IA$^d$-OVA (■), IA$^d$+OVA (x), thrombin treated IA$^d$-OVA (+), and IE$^{dk}$-MCC (● and IA$^d$ (▲) samples as controls. The results indicate that both IA$^d$-OVA and thrombin treated IA$^d$-OVA induced IL-2 production by the T cell hybridoma. Conversely, IA$^d$+OVA, IE$^{dk}$-MCC and IA$^d$ protein failed to induce an IL-2 response.

Two other T cell hybridomas specific for IA$^d$ plus OVA peptide were tested in similar assays. One responded in the same way as that illustrated above. Another hybridoma failed to respond to IA$^d$-OVA regardless of whether or not the linker had been cleaved with thrombin. It is possible that recognition of the peptide by the receptor on this T cell hybridoma is context sensitive, i.e. it is inhibited in some way by the presence of the few amino acids of the β1 domain of IA$^d$ on the N-terminus of the peptide.

The results shown in FIG. 3 indicate that the a covalent association of peptide and Class II protein by a linker forms a Peptide-MHC complex that can be recognized by T cells specific for the combination. Moreover, the covalently associated Peptide-MHC complex induces a better immune response than complexes formed by mixing the peptide with the MHC protein in solution. The results also indicate that the covalently associated Peptide-MHC complex is more stable than an MHC protein in the absence of peptide. In both cases treatment of the peptide/MHC covalent complex with thrombin to cleave the linker between them only modestly improved T cell hybridoma recognition. This indicates that the linker most likely extends from the C-terminal end of the peptides around the side rather than over the top of the Class II α chain α helix in order to reach the N terminal end of the Class II β chain (see FIG. 1).

Together all these data show that genes coding for peptides covalently associated to MHC Class II proteins by a linker can be expressed as soluble proteins capable of being recognized by T cells. The data also indicate that the peptides linked to the MHC protein form stable complexes more effective at stimulating a T cell response than complexes formed by mixing the peptide with the MHC protein.

Example 2

This Example demonstrates that genes coding for peptides covalently associated to MHC Class II proteins by a linker can be expressed as stable membrane-bound proteins capable of being recognized by T cells.

Using PCR amplification, a hybrid IAβ$^b$ nucleic acid molecule was produced containing sequences encoding amino acid residues 56-73 of IEα$^d$ (IEα$^d$ Peptide (56-73), a linker containing a thrombin cleavage site, and an IAβ$^b$ gene, including the extracellular, transmembrane and cytoplasmic domains. The hybrid molecule was prepared as follows. Referring to Table 5 - (SEQ ID NO:38 and SEQ ID NO:39), a first fragment (fragment 362-363) was produced encoding the leader and the first 4 codons of the β1 domain of IAβ$^b$, and the first 12 codons of the IEα$^d$ peptide using Primer #362 (5' CCCGAGCTCGGGAATTCTTAGAGATG-GCTCTGCAG 3') (SEQ ID NO:36) and #363 (5' TTA-CAACCGGTCACGTGGGACTCGGAGTTTC-GATCGAAGCCTCAGAGGCGGG 3')(SEQ ID NO:37) on an IAβ$^b$ cDNA template. Primer #362 (SEQ ID NO:36) contains an EcoRI

TABLE 5

Aβb with Ead Peptide in pTZ18R

```
         10         20         30         40         50         60         70           80         90        100        110        120
         |          |          |          |          |          |          |            |          |          |          |          |
                                                                              EcoRI
                                            |------76------>               |-\/---362------>
      CAGGAAACAGCTATGACCATGATTACGCCAAGCTTGCATGCCTGCAGGTCGACTCTAGAGGATCCCCGGGTACCGAGCTCGAATTCTTAGAGATGGCTCTGCACATCCCCAGCCTCCTCTCGGCCTGTGTGGTGCTG
                                                                                                              M  A  L  Q  I  P  S  L  L  L  S  A  A  V  V  V  L
                                                                                                              <--------------- Leader ---------------->

130        140        150        160        170        180        190        200        210        220        230        240        250
         |          |          |          |          |          |          |          |          |          |          |          |          |
        EspI                                                 NheI                                         SalI                        BamHI
      |-\/--|                                              |-\/--363------>                             |-\/--364------>            |-\/--365------>
      ATGGTGCTGAGCAGCCCAGGGACTGAGGGCGGAGACTCCGAAGCTTAGCTTTGAGGCTCAGGGGTGCCAACATTGCTGTCGACAAGGCTGGAGGTGGATCCGGTGGAGGGGAAGTGGAGGT
      M  V  L  S  S  P  G  T  E  G  G  D  S  E  A  S  F  E  A  Q  G  A  L  A  N  I  A  V  D  K  A  G  G  G  S  G  G  G  G  E  V  E
                                             <--- B1 ---><----------- Ead Peptide --------------------------------------><-------- Linker --------

260        270        280        290        300        310        320        330        340        350        360        370        380
         |          |          |          |          |          |          |          |          |          |          |          |          |
                  |-----270----->
      GGAGGGTCTGAAAGGCATTTCGTTGTACCAGTTCATGGGCGAGTGCTACTTCACCAACGGGACGCAGCGCATACGATATGACCAGAGACATCTACAACCGGGAGGAGTACGTGCGCTACGACAGCGAC
       G  G  S  E  R  H  F  V  Y  Q  F  M  G  E  C  Y  F  T  N  G  T  Q  R  I  R  Y  V  T  R  Y  I  Y  N  R  E  E  Y  V  R  Y  D  S  D
                  <---- B1 ---->

390        400        410        420        430        440        450        460        470        480        490        500        510
         |          |          |          |          |          |          |          |          |          |          |          |          |
                 BstEII                                                                                                                 BsgI
               |-\/--|                                                                                                               |-\/--|
      CTGGGCGAGCACCGCGCGGTGACCGAGCTGGGGCGGCCCGACGCCGAGTACTGGAACAGCCAGCCGGAGATCCTGGAGCGAACGCGGGCCGAGGTGGACACGGTGTCCAGACACAACTACGAGGGGCCG
       V  G  E  H  R  A  V  T  E  L  G  R  P  D  A  E  Y  W  N  S  Q  P  E  I  L  E  R  T  R  A  E  V  D  T  V  C  R  H  N  Y  E  / G  P 520        530        540        550        560        570        580        590        600        610        620        630        640
         |          |          |          |          |          |          |          |          |          |          |          |          |
                                                                        |-----t----272----->
                                                                      <----c----271-----|
      GAGACCCACACCTCCCTGCGGCGGCTTGAACAGCCCAATGTCGTCATCTCCCTGTCCAGGACAGAGGCCCTCAACCACCACAACACTCTGGTCTGCTCAGTGACAGATTTCTACCCAGCCAAGATCAAA
       E  T  H  T  S  L  R  R  L  E  Q  P  N  V  V  I  S  L  S  R  T  E  A  L  N  H  H  N  T  L  V  C  S  V  T  D  F  Y  P  A  K  I  K
                              <-- β1 --><------- β2 -------|
```

TABLE 5-continued

Aβb with Ead Peptide in pTZ18R

```
     650        AccII 660      670 Esp3I      680           690          700          710          720          730          740          750          760          770
      |           |\ /  |      |\ /|          |            |            |            |            |            |            |            |            |            |
GTGCGCTGGTTCCGGTTCAGGAGGACGGGAATGGGGACTGTCATCCACACAGCTTATTAGGAATGGGGACTGACCTTCCAGGTCCTGGTCATGCTGGAGATGACCCCTCGGCGGGGAGAGAGGTCTAC
 V  R  W  F  R  N  G  Q  E \ E  T  V  G  V  S  S  T  Q  L  I  R  N  G  D  W  T  F  Q  V  L  V  M  L  E  M  T  P  R  R  G  E  V  Y 780          790          800          810          820          830          840          850          860          870          880          890          900
      |            |            |            |\ /|          |            |            |            |            |            |            |            |            |
                                             BstXI                                                 <- -259- -c- -- t a a g c a t  g c g g
ACCTGTCACGTGGAGCATCCAGCTGAAGAGCCTGAAGAGCCCCATCACTGTGGAGTGGAGGGCACAGTCTGAGTCTGCCTGGAGCAAGATGTTCAGGGGCATCGGGGGCTGCGTGCTTGGGGTGATCTTCCTCGGG
      |\ /|
    PmaCI
 T  C  H  V  E  H  P  S  L  K  S  P  I  T  V  E  W  R  A  Q  S  E  S  A  W  S  K  M  L  S  G  I  G  G  C  V  L  G  V  I  F  L  G
                                                                                              -- β2 -----  > <-----------   Transmembrane ----------

910          920          930          940          950          960          970          980          990          1000         1010         1020
      |            |            |            |\ /|          |            |\ /|          |            |\ /|          |            |            |
                                             XhoI                        EcoNI                      EcoRI         HindIII                               <----59-----
CTTGGCCCTTTTCATCCGTCACAGGAGTCAGAAAGGACCTCGAGGCCCTCCTCCAGCAGGGCTTCCTGCAGTGAGAATTCGGAAGCTTGGCACTGGCCCGTCGTTTTACAACGTCGTGACTGGGAAAAC
 L  G  L  F  I  R  H  R  S  Q  K  G  P  P  R  G  P  P  P  A  C  L  L  Q *
----------------------->  <---------------  Cytoplasmic  ------------------- >
``` site and Primer #363 (SEQ ID NO:37) contains an NheI site. Fragment 362-363 was used as a template for a second PCR fragment (fragment 362-364) in which fragment 362-363 was extended by adding sequerces encoding the remainder of the IEα$^d$ peptide and the first 7 codons of the linker were added using Primer #364 (5' GGTGGCCTAGGTGGTGG-TGGAAGTCGGAACAGCTGTCGTTACAACCGGT-CACG3')(SEQ ID NO:40) Primer #364 (SEQ ID NO:40) contains a SalI and a BamHI site.

Using PCR amplification, a third fragment (fragment 365-366) was produced which containing sequences encoding the IAβ$^b$ β (minus the first four codons), β2, transmembrane and cytoplasmic domains. Fragment 365-366 was produced using Primer #365 (5' GGTGGATCCGGTG-GAGGGGGAAGTGGAGGTGGAGGGTCT-GAAAGGCATTTCGTG 3') (SEQ ID NO:41) and Primer #366 (5' CGGTTCGAAGGCTTAAGAGTGACGTC-CTCGGGACG 3')(SEQ ID NO:42) Primer #365 (SEQ ID NO:41) contains a BamHI site and Primer #366 (SEQ ID NO:42) contains both an EcoRI and a HindIII site. A nucleic acid molecule was formed from the above fragments having sequences encoding an IEα$^d$ (56-73) peptide, a linker and an IAβ$^b$ protein, referred to as N-IA$^b$-Ea.

For transfection into B cells, the recombinant molecule pM12-IA$^b$-Ea was produced by digesting fragment 362-364 with EcoRI and BamHI and ligating the digested fragment into EcoRI BamHI digested carrier vector pTZ18R to form a pTZ-IA$^b$-Ea(362-364) construct. Fragment 365-366 was then digested with BamHI and HindIII and the digested fragment was ligated into the pTZ-IA$^b$-Ea(362-364) construct that had been digested with BamHI and HindIII to form a pTZ-IA$^b$-Ea construct. The pTZ-IA$^b$-Ea construct was then digested with EcoRI and subcloned into the expression vector pDOI-5 (obtained from D. Mathis and C. Benoit, containing a class II promoter and enhancer region, a β-globin intron and EcoRI cloning site) to form the recombinant molecule pM12-IA$^b$Ea encoding IA$^b$Ea protein. pM12-IA$^b$Ea recombinant molecules having sequences encoding IA$^b$Ea protein in the correct orientation were identified by nucleic acid sequencing multiple pM12-IA$^b$Ea recombinant molecules.

The recombinant molecule pFIB-IA$^b$Ea was produced for transfection into fibroblast cells by subcloning the pTZIA-$^b$Ea construct described above with EcoRI and subcloning the EcoRI fragment into EcoRI digested expression vector pHβAcPr-1-neo (obtained from S. Hedrick, containing the human β-actin promoter and enhancer, and a sequence encoding neomycin resistance). The orientation of each cloned insert was determined after cloning by nucleic acid sequencing.

Table 6 (SEQ ID NO:43 and SEQ ID NO:44 and SEQ ID NO:45) lists the nucleic acid and protein sequence of the IA β chain from the leader, through the peptide and linker, into the β1 domain. A similar construction was made for IAβ$^b$ without nucleic acid sequences encoding antigenic peptide as controls.

TABLE 6

Construction of IAβ$^b$ with Eα$^d$ Peptide

IAβ$^b$ Alone

```
      EcoRI
      \/
GGGAATTCTTAGATGGCTCTGCAGATCCCCAGCCTCCTCCTCTGCCCTGCTGTGGTGGTGCTGATGGTG
           M   A   L   Q   I   P   S   L   L   L   S   A   A   V   V   V   L   M   V
        <---------------------------------- Leader -------------

CTGAGCAGCCCAGGGACTGAGGGCGGAGACTCCGAAAGGCATTTCGTGTACCAGTTCATGGGCGAGTGCTAC
   L   S   S   P   G   T   E   G   G   D   S   E   R   H   F   V   Y   Q   F   M   G   E   C   Y
   ---------------------->  <--Aβ$^b$  β1 -----  - -
```

IAβ$^b$ with Eα$^d$ Peptide

```
      EcoRI
      \/
GGGAATTCTTAGAGATGGCTCTGCAGATCCCCAGCCCTCTCCTCTCGGCTGCTGTGGTGGTGCTGATGGTG
           M   A   L   Q   I   P   S   L   L   L   S   A   A   V   V   V   L   M   V
        <----------------------------------Leader  ----------
CTGAGCAGCCCAGGGACTGAGGGCGGAGACTCCGAAGCTAGCTTTGAGGCTCAGGGTGCACTGGCCAACATT
   L   S   S   P   G   T   E   G   G   D   S   E   A   S   F   E   A   Q   G   A   L   A   N   I
   ---------------------->  <--β1 -----  > <--------------- Eα$^d$ Peptide      ------

GCTGTCGACAAGGCTGGAGGTGGTGGATCCGGTGGAGGGGGAAGTGGAGGTGGAGGGTCTGAAAGGCATTTC
   A   V   D   K   A   G   G   G   G   S   G   G   G   G   S   G   G   G   S   E   R   H   F
   -------------->  <--------------- Linker     --------------- > <-β1 ---
```

A B cell line M12.C3 was transfected with the recombinant molecule pM12-IA$^b$Ea or a recombinant molecule encoding an IA$^b$ protein. Using standard fluorescence activated cell sorter analysis (FACS analysis), two different antibodies were used to detect expression of IA$^b$-Ea protein on the surface of the M12 cells, an anti-IA$^b$ antibody and an antibody (5A) specific for IA$^b$ protein bound by IEα$^d$ peptide. The results shown in FIG. 4 indicate that the M12.C3 cells transfected with IA$^b$ Ea protein react well with both antibodies. Untransfected M12.C3 cells and normal spleen cells are shown as negative controls. Thus, the IA$^b$-Ea protein is expressed in M12.C3 cells and reaches the cell surface. Moreover, the covalently bound peptide is bound to the peptide-binding groove of the IA$^b$ protein as indicated by the binding of the 5A antibody.

Figure 5A:
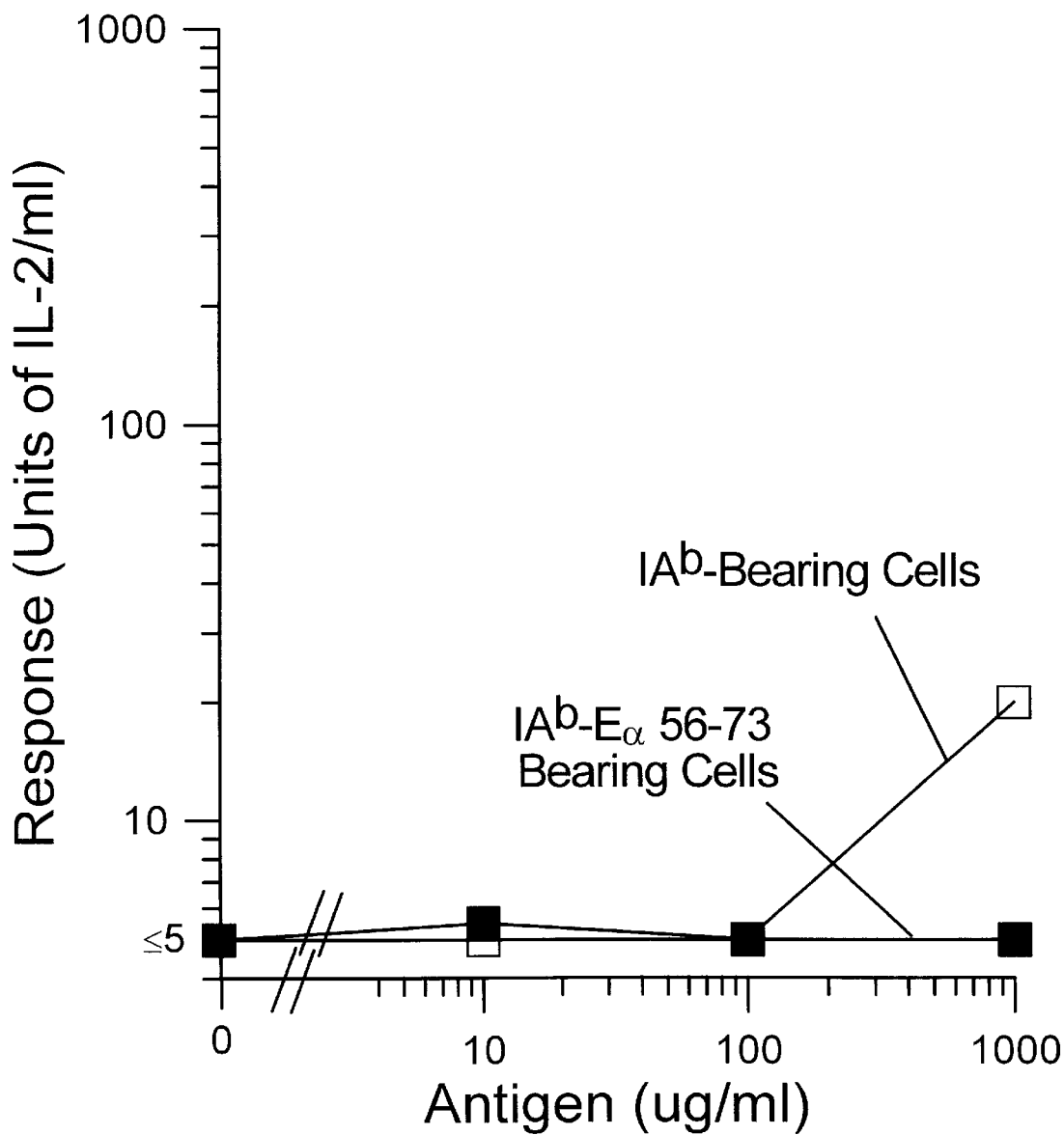
FIG. 5 illustrates the inhibition by covalently associated peptide of OVA and ovalbumin to IA$^b$-Ea protein expressed on M12.C3 cells.
Figure 5B:
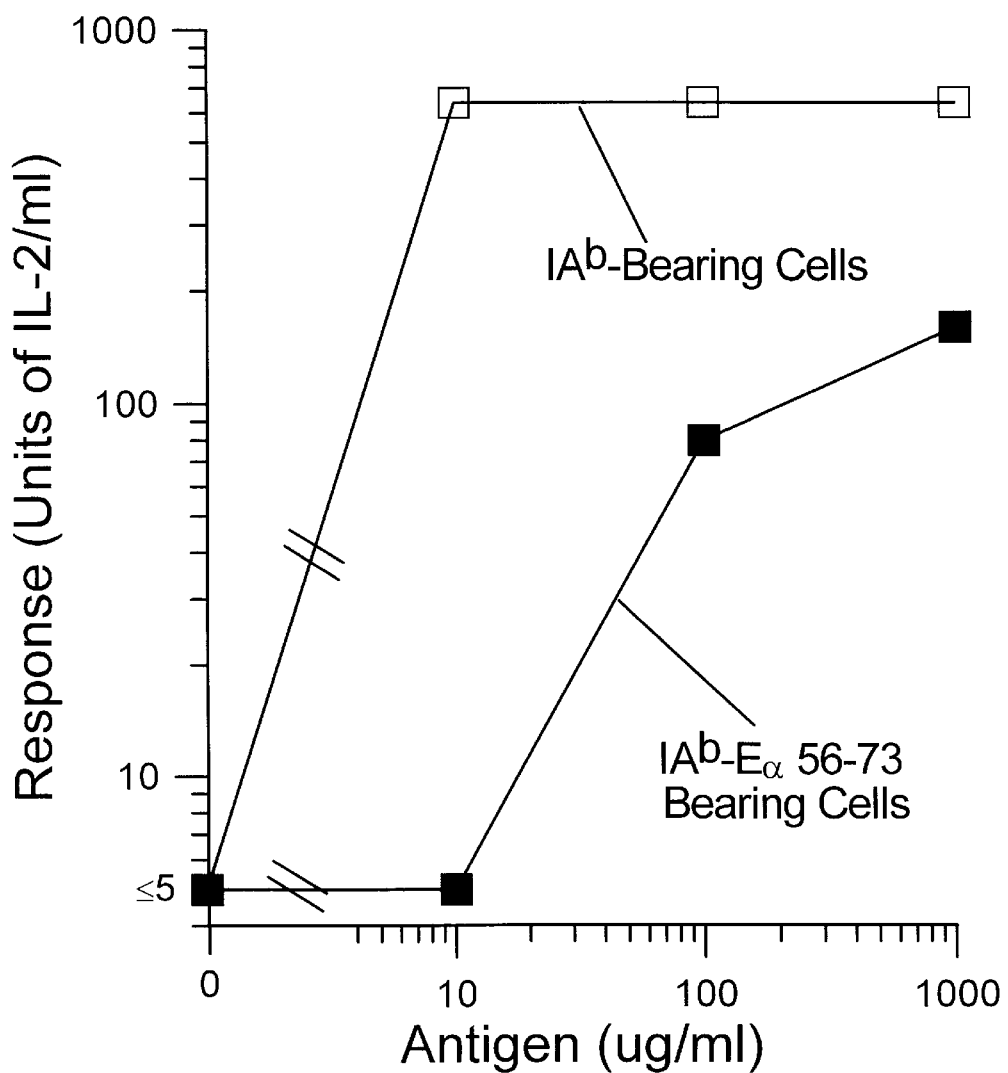

An experiment was performed to determine the extent of binding of the covalently associated IEα$^d$ to the binding site of the associated IA$^b$ protein. M12.C3 cells bearing either IA$^b$-Ea protein or IA$^b$ protein were mixed with T hybridoma cells specific for IA$^b$ protein bound by cOVA peptide (BO.97.10). Increasing concentrations of either cOVA peptide (described in Example 1) or ovalbumin was added to the mixture and the amount of IL-2 produced by the hybridoma was measured. The cOVA peptide is known to be capable of binding to the binding site of $IA^b$ protein. Thus, the COVA peptide will bind to any $IA^b$ protein not bound by peptide. The IL-2 production is a measurement of the amount of $IA^b$ protein bound by cOVA peptide present in the mixture. The results are shown in FIG. 5.

M12.C3 cells bearing $IA^b$-Ea protein (■) did not stimulate IL-2 production by BO.97.10 cells in the presence of ovalbumin. M12.C3 cells bearing $IA^b$ protein (□) did stimulate IL-2 production in the presence of a substantial concentration of ovalbumin. These results indicate that ovalbumin is being taken up by the M12.C3 cells, processed and presented on the cell surface in association with the $IA^b$-Ea protein but not in association with $IA^b$-Ea protein. Thus, the $IA^b$-Ea protein is not available to bind ovalbumin peptide inside the cell, most likely because the binding site of the protein is bound by the covalently associated $IE\alpha^d$ peptide.

As expected, M12.C3 cells bearing $IA^b$ protein (□) did stimulate IL-2 production in the presence of cOVA peptide. M12.C3 cells bearing $IA^b$-Ea protein (■) also stimulated IL-2 production in the presence of cOVA. However, the $IA^b$-Ea protein bearing cells required about 10-fold more cOVA and stimulated about 10-fold less IL-2 production than the $IA^b$ protein bearing cells. Thus, only about 10% of the $IA^b$-Ea protein was bound by cOVA peptide and about 90% of the $IA^b$-Ea protein had $IE\alpha^d$ bound to the binding site of the $IA^b$ protein. The results also indicate that the covalently associated $IE\alpha^d$ peptide of the $IA^b$-Ea protein is bound in the $IA^b$ binding site in a stable manner.

Figure 6:
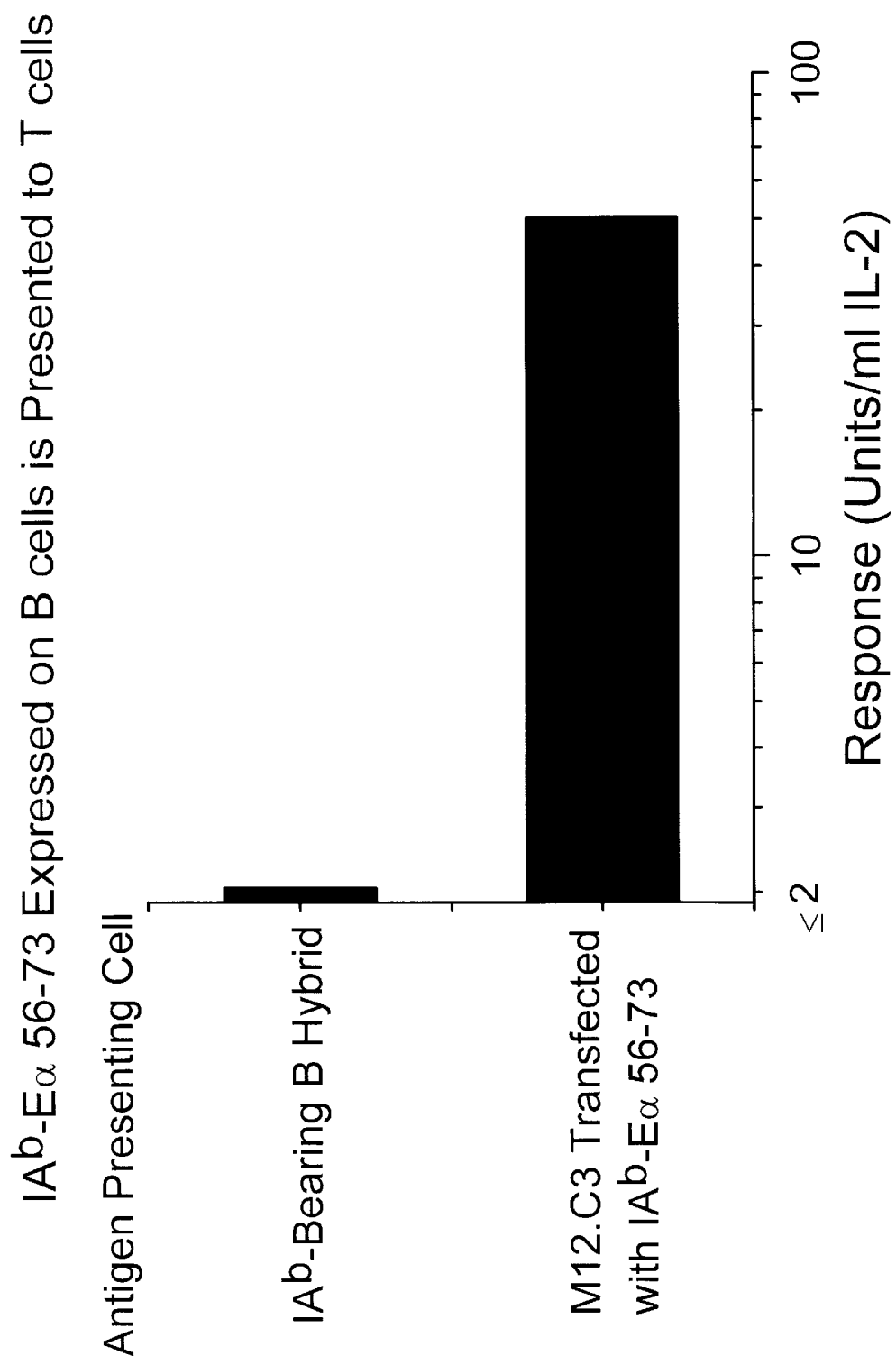
FIG. 6 illustrates stimulation of T cell hybridomas IA$^b$-Ea protein bearing M12.C3 cells.

The ability of $IA^b$-Ea protein bearing M12.C3 cells to present peptide was tested by measuring IL-2 production by a T cell hybridoma specific for $IA^b$-Ea protein. M12.C3 cells bearing $IA^b$-Ea protein or $IA^b$ protein ($10^5$ cells/well) were mixed with BE-20.6 T hybridoma cells ($10^5$ cells/well) and cultured for 24 hours. Following incubation, the amount of IL-2 produced by the hybridomas was measured. The results indicate that $IA^b$-Ea protein M12.C3 cells were capable of inducing IL-2 production by the hybridoma while $IA^b$ protein bearing M12.C3 cells were not capable of inducing IL-2 production (see FIG. 6). Thus, the covalently bound peptide is bound to the peptide-binding groove of the $IA^b$ protein and expressed on the surface of the B cell in a manner such that the complex can induce a T cell response.

In a second experiment, fibroblasts were transfected with the recombinant molecule pFIB-$IA^b$-Ea or a recombinant molecule encoding an $IA^b$ protein were transfected into fibroblast cells. Expression of $IA^b$-Ea protein on the surface of the fibroblasts was analyzed by FACS analysis using the same antibodies described above. As shown in FIG. 7, the fibroblasts transfected with the recombinant molecule encoding $IA^b$-Ea protein react well with both anti-$IA^b$ antibody and antibody specific for $IA^b$ protein bound by $IE\alpha^d$ peptide (5A). Thus, the proteins encoded by the transfected $IA^b$-Ea recombinant molecule were well expressed in fibroblast cells and the $IA^b$-Ea protein reaches the cell surface of the fibroblast.

Figure 8:
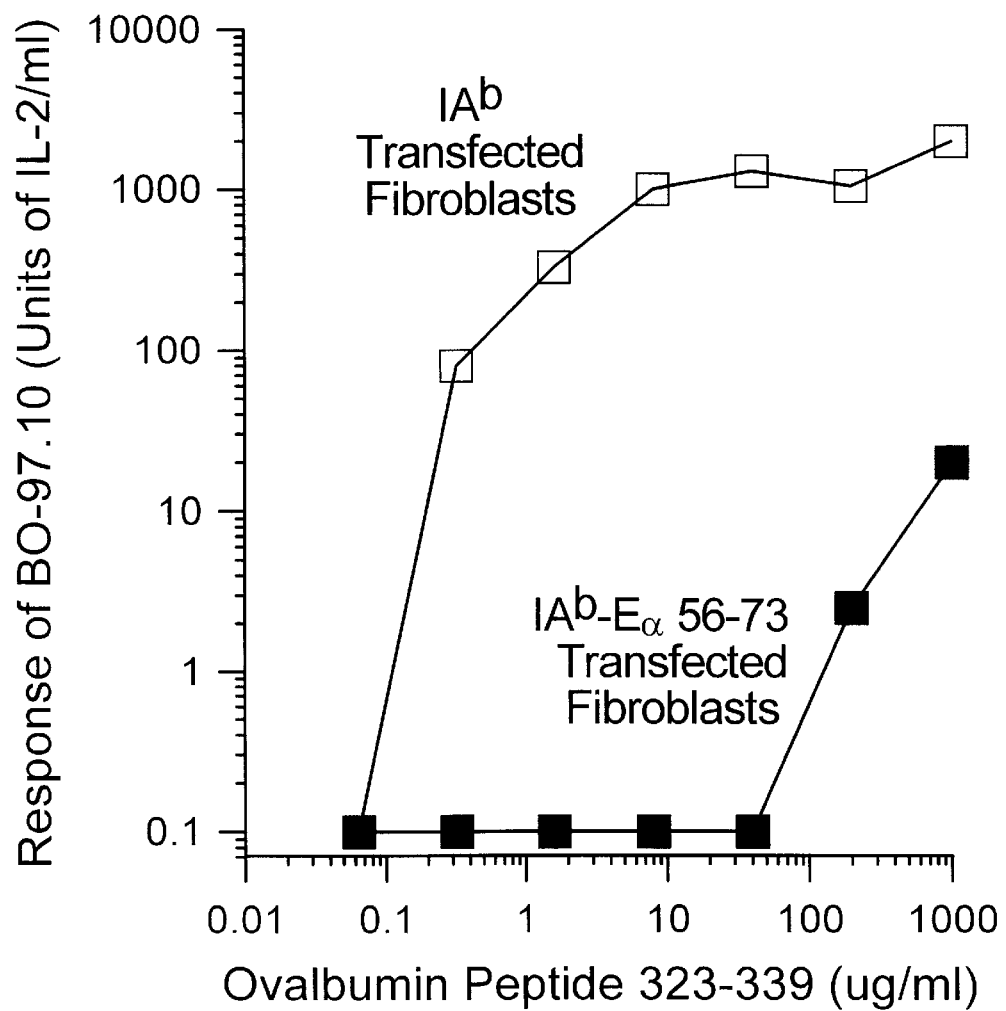
FIG. 8 illustrates the inhibition by covalently associated peptide of OVA binding to IA$^b$-Ea protein expressed on fibroblast cells.

Similar to the experiments performed with the B cells, fibroblast cells bearing $IA^b$-Ea protein or $IA^b$ protein were tested to determine the extent of binding of the covalently associated $IE\alpha^d$ to the binding site of the $IA^b$ protein. Fibroblasts bearing either $IA^b$-Ea protein or $IA^b$ protein were mixed with BO.97.10 T hybridoma cells. Increasing concentrations of cOVA peptide was added to the mixture and the amount of IL-2 produced by the hybridoma was measured. The results are shown in FIG. 8. As expected, the fibroblasts bearing $IA^b$ protein (□) did stimulate IL-2 production in the presence of cOVA peptide. Fibroblasts bearing $IA^b$-Ea protein (■) stimulated about 10-fold less IL-2 production and required about 10-fold more cOVA peptide. Thus, similar to the $IA^b$-Ea protein produced in B cells, about 90% of the $IA^b$-Ea protein produced in fibroblasts are bound by $IE\alpha^d$ peptide.

Figure 9:
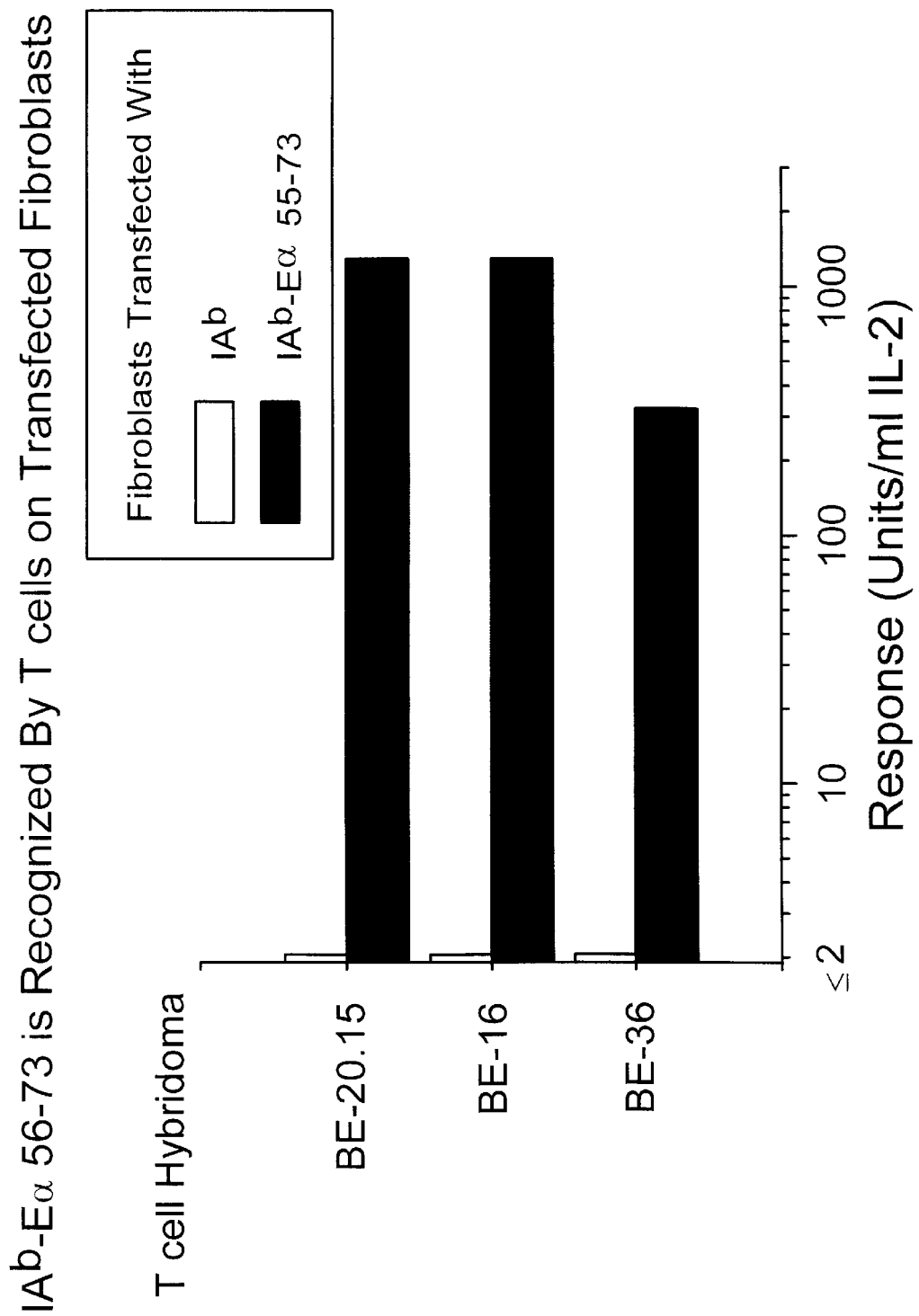
FIG. 9 illustrates stimulation of T cell hybridomas by IA$^b$Ea bearing fibroblast cells.

Fibroblast cells bearing $IA^b$-Ea protein or $IA^b$ protein were tested for their ability to induce IL-2 production by three different T cell hybridomas, BE-20.15, BE-16 or BE-36. The hybridoma cells and the fibroblast cells were incubated according to the method described above and the amount of IL-2 production was measured. The results shown in FIG. 9 indicate that fibroblast cells bearing $IA^b$-Ea protein were capable of inducing IL-2 production while fibroblasts bearing $IA^b$ protein did not induce IL-2 production. These results demonstrate that MHC protein that has a peptide covalently associated via a linker, can be expressed in a cell type that does not typically express MHC protein, and that the Peptide-MHC complex can be recognized by a hybridoma, resulting in stimulation of IL-2 production.

Together all these data show that genes coding for peptides linked to MHC Class II proteins can be expressed as membrane-bound protein in cells. The covalently bound peptide can bind to the groove of the MHC protein and be recognized by antibodies or T cells.

What is claimed is:

1. An isolated Peptide-L-MHC heterodimer comprising:
   a) an MHC segment of said heterodimer which forms a peptide binding groove, comprising at least a portion of an MHC class II β chain and at least a portion of an MHC class II α chain;
   b) an antigenic peptide comprising from about 5 to about 40 amino acid residues which binds to said peptide binding groove; and
   c) a linker comprising an amino acid sequence of at least about 15 amino acid residues, wherein said peptide is covalently linked by said linker to the N-terminus of one of said MHC class II α and β chains, said linker facilitating the binding of said peptide to said peptide binding groove such that said peptide and said MHC segment form a conformation that is recognized by a T cell receptor without substantially hindering interaction between said Peptide-L- MHC heterodimer and said T cell receptor;
   wherein said antigenic peptide, linker and at least one of said MHC class II α and β chains is encoded by a nucleic acid molecule, said nucleic acid molecule including a nucleic acid sequence encoding a signal segment attached to the N-terminus of said antigenic peptide.

2. An isolated Peptide-L-MHC heterodimer comprising:
   a) an MHC segment of said heterodimer which forms a peptide binding groove, comprising at least a portion of an MHC class I α chain and at least a portion of an MHC class I β2m chain;
   b) an antigenic peptide comprising from about 8 to about 20 amino acid residues which binds to said peptide binding groove; and
   c) a linker comprising an amino acid sequence of at least about 8 amino acid residues, wherein said peptide is covalently linked by said linker to the N-terminus of one of said MHC class I α and β2m chains, facilitating the binding of said peptide to said peptide binding groove such that said peptide and said MHC segment form a conformation that is recognized by a T cell receptor without substantially hindering interaction between said Peptide-L-MHC heterodimer and said T cell receptor;
   wherein said antigenic peptide, linker and at least one of said MHC class I α and β2m chains is encoded by a nucleic acid molecule, said nucleic acid molecule including a nucleic acid sequence encoding a signal segment attached to the N-terminus of said antigenic peptide.

3. The Peptide-L-MHC heterodimer of claim 1 or 2, wherein said peptide is at least a portion of an antigen selected from the group consisting of autoantigens, infectious antigens, toxins, and allergens.

4. The Peptide-L-MHC heterodimer of claim 1, wherein said peptide is selected from the group consisting of: Arg-Ala-Asp-Leu-Ile-Ala-Tyr-Leu-Lys-Gln-Ala-Thr-Lys (SEQ ID NO:1), Val-His-Ala-Ala-His-Ala-Glu-Ile-Asn-Glu-Ala-Gly-Arg (SEQ ID NO:2) and Ala-Ser-Phe-Glu-Ala-Gln-Gly-Ala-Leu-Ala-Asn-[Iso]Ile-Ala-Val-Asp-Lys-Ala (SEQ ID NO:5).

5. The Peptide-L-MHC heterodimer of claim 1 or 2, wherein said linker is processable.

6. The Peptide-L-MHC heterodimer of claim 1 or 2, wherein said linker is substantially neutral.

7. The Peptide-L-MHC heterodimer of claim 1 or 2, wherein said linker comprises residues selected from the group consisting of glycine, alanine, serine, valine, threonine and proline.

8. The Peptide-L-MHC heterodimer of claim 1 or 2, wherein said linker comprises Gly-Gly-Gly-Gly-Ser-Gly-Gly-Gly-Gly-Ser (SEQ ID NO:7).

9. The Peptide-L-MHC heterodimer of claim 1 or 2, wherein said linker comprises Gly-Gly-Gly-Gly-Ser-Leu-Val-Pro-Arg-Gly-Ser-Gly-Gly-Gly-Gly-Ser (SEQ ID NO:6).

10. The Peptide-L-MHC heterodimer of claim 1 or 2, wherein said Peptide-L-MHC heterodimer is secreted from a cell that produces said Peptide-L-MHC heterodimer.

11. The Peptide-L-MHC heterodimer of claim 1 or 2, wherein said Peptide-L-MHC heterodimer is anchored to an artificial or natural lipid-containing substrate.

12. The Peptide-L-MHC heterodimer of claim 11, wherein said lipid-containing substrate is selected from the group consisting of cells, cellular membranes, liposomes and micelles.

13. The Peptide-L-MHC heterodimer of claim 1 or 2, wherein said Peptide-L-MHC heterodimer is anchored to the plasma membrane of a mammalian cell.

14. The Peptide-L-MHC heterodimer of claim 1 or 2, wherein said nucleic acid molecule encodes a Peptide-L-MHC heterodimer further comprising at least one transmembrane segment which anchors said Peptide-L-MHC heterodimer to a lipid-containing substrate.

15. The Peptide-L-MHC heterodimer of claim 1 or 2, wherein said nucleic acid molecule is operatively linked to an expression vector to form a recombinant molecule.

16. The Peptide-L-MHC heterodimer of claim 15, wherein said Peptide-L-MHC recombinant molecule is transformed into a host cell to produce a recombinant cell which expresses said recombinant molecule.

17. The Peptide-L-MHC heterodimer of claim 16, wherein said host cell is selected from the group consisting of bacterial, fungal, insect and mammalian cells.

18. The Peptide-L-MHC heterodimer of claim 16, wherein said host cell stimulates a T cell response.

19. The Peptide-L-MHC heterodimer of claim 16, wherein said host cell does not stimulate a T cell response.

20. The Peptide-L-MHC heterodimer of claim 16, wherein said host cell is selected from the group consisting of antigen presenting cells, fibroblasts, red blood cells, pluripotent progenitor cells, epithelial cells and neural cells.

21. The Peptide-L-MHC heterodimer of claim 1 or 2 produced by a method comprising:
   a) culturing a cell transformed with a nucleic acid molecule comprising a sequence encoding said Peptide-L-MHC heterodimer, said step of culturing being conducted to produce said Peptide-L-MHC heterodimer; and
   b) recovering said Peptide-L-MHC heterodimer.

22. A formulation which suppresses T cell activity comprising a Peptide-L-MHC heterodimer comprising:

(a) an MHC segment of said heterodimer which forms a peptide binding groove, comprising at least a portion of an MHC class II β chain and at least a portion of an MHC class II α chain;

(b) an antigenic peptide comprising from about 5 to about 40 amino acid residues which binds to said peptide binding groove; and (c) a linker comprising an amino acid sequence of at least about 15 amino acid residues, wherein said peptide is covalently linked by said linker to the N-terminus of one of said MHC class II α and β chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;

wherein said antigenic peptide, linker and at least one of said MHC class II α and β chains is encoded by a nucleic acid molecule, said nucleic acid molecule including a nucleic acid sequence encoding a signal segment attached to the N-terminus of said antigenic peptide;

wherein said heterodimer is anchored to the plasma membrane of a cell that does not stimulate a T cell response.

23. A formulation which suppresses T cell activity comprising a Peptide-L-MHC heterodimer comprising:

(a) an MHC segment of said heterodimer which forms a peptide binding groove, comprising at least a portion of an MHC class I α chain and at least a portion of an MHC class I β2m chain;

(b) an antigenic peptide comprising from about 8 to about 20 amino acid residues which binds to said peptide binding groove; and (c) a linker comprising an amino acid sequence of at least about 8 amino acid residues, wherein said peptide is covalently linked by said linker to the N-terminus of one of said MHC class I α and β2m chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;

wherein said antigenic peptide, linker and at least one of said MHC class I α and β2m chains is encoded by a nucleic acid molecule, said nucleic acid molecule including a nucleic acid sequence encoding a signal segment attached to the N-terminus of said antigenic peptide;

wherein said heterodimer is anchored to the plasma membrane of a cell that does not stimulate a T cell response.

24. The formulation of claim 22 or 23, wherein said cell is selected from the group consisting of red blood cells, fibroblasts, pluripotent progenitor cells, epithelial cells and neural cells.

25. A formulation which stimulates T cell activity comprising a Peptide-L-MHC heterodimer comprising:

(a) an MHC segment of said heterodimer which forms a peptide binding groove, comprising at least a portion of an MHC class II β chain and at least a portion of an MHC class II α chain;

(b) an antigenic peptide comprising from about 5 to about 40 amino acid residues which binds to said peptide binding groove; and (c) a linker comprising an amino acid sequence of at least about 15 amino acid residues, wherein said peptide is covalently linked by said linker to the N-terminus of one of said MHC class II α and β chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;

wherein said antigenic peptide, linker and at least one of said MHC class II α and β chains is encoded by a nucleic acid molecule, said nucleic acid molecule including a nucleic acid sequence encoding a signal segment attached to the N-terminus of said antigenic peptide;

wherein said heterodimer is anchored to the plasma membrane of a cell that stimulates a T cell response.

26. A formulation which stimulates T cell activity comprising a Peptide-L-MHC heterodimer comprising:

(a) an MHC segment of said heterodimer which forms a peptide binding groove, comprising at least a portion of an MHC class I α chain and at least a portion of an MHC class I β2m chain;

(b) an antigenic peptide comprising from about 8 to about 20 amino acid residues which binds to said peptide binding groove; and (c) a linker comprising an amino acid sequence of at least about 8 amino acid residues, wherein said peptide is covalently linked by said linker to the N-terminus of one of said MHC class I α and β2m chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;

wherein said antigenic peptide linker and at least one of said MHC class I α and β2m chains is encoded by a nucleic acid molecule, said nucleic acid molecule including a nucleic acid sequence encoding a signal segment attached to the N-terminus of said antigenic peptide;

wherein said heterodimer is anchored to the plasma membrane of a cell that stimulates a T cell response.

27. The formulation of claim 25 or 26, wherein said cell that stimulates a T cell response is selected from the group consisting of macrophages, B cells and dendritic cells.

28. A formulation which suppresses T cell activity comprising a Peptide-L-MHC heterodimer comprising:

(a) an MHC segment of said heterodimer which forms a peptide binding groove, comprising at least a portion of an MHC class II β chain and at least a portion of an MHC class II α chain;

(b) an antigenic peptide comprising from about 5 to about 40 amino acid residues which binds to said peptide binding groove; and (c) a linker comprising an amino acid sequence of at least about 15 amino acid residues, wherein said peptide is covalently linked by said linker to the N-terminus of one of said MHC class II α and β chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;

wherein said antigenic peptide, linker and at least one of said MHC class II α and β chains is encoded by a nucleic acid molecule, said nucleic acid molecule including a nucleic acid sequence encoding a signal segment attached to the N-terminus of said antigenic peptide;

wherein said heterodimer is secreted from a cell that produces said heterodimer.

29. A formulation which suppresses T cell activity comprising a Peptide-L-MHC heterodimer comprising:
   (a) an MHC segment of said heterodimer which forms a peptide binding groove, comprising at least a portion of an MHC class I α chain and at least a portion of an MHC class I β2m chain;
   (b) an antigenic peptide comprising from about 8 to about 20 amino acid residues which binds to said peptide binding groove; and
   (c) a linker comprising an amino acid sequence of at least about 8 amino acid residues, wherein said peptide is covalently linked by said linker to the N-terminus of one of said MHC class I α and β2m chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;

wherein said antigenic peptide, linker and at least one of said MHC class I α and β2m chains is encoded by a nucleic acid molecule, said nucleic acid molecule including a nucleic acid sequence encoding a signal segment attached to the N-terminus of said antigenic peptide;

wherein said heterodimer is secreted from a cell that produces said heterodimer.

30. A nucleic acid molecule comprising a sequence encoding a Peptide-L-MHC heterodimer comprising:
   (a) an MHC segment of said heterodimer which forms a peptide binding groove, comprising at least a portion of an MHC class II β chain and at least a portion of an MHC class II α chain;
   (b) an antigenic peptide comprising from about 5 to about 40 amino acid residues which binds to said peptide binding groove; and
   (c) a linker comprising an amino acid sequence of at least about 15 amino acid residues, wherein said peptide is covalently linked by said linker to the N-terminus of one of said MHC class II α and β chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;
   wherein said nucleic acid molecule comprises a nucleic acid sequence encoding a signal segment covalently attached to the N-terminus of said antigenic peptide.

31. A nucleic acid molecule comprising a sequence encoding a Peptide-L-MHC heterodimer comprising:
   (a) an MHC segment of said heterodimer which forms a peptide binding groove, comprising at least a portion of an MHC class I α chain and at least a portion of an MHC class I β2m chain;
   (b) an antigenic peptide comprising from about 8 to about 20 amino acid residues which binds to said peptide binding groove; and
   (c) a linker comprising an amino acid sequence of at least about 8 amino acid residues, wherein said peptide is covalently linked by said linker to the N-terminus of one of said MHC class I α and β2m chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;
   wherein said nucleic acid molecule comprises a nucleic acid sequence encoding a signal segment covalently attached to the N-terminus of said antigenic peptide.

32. The nucleic acid molecule of claim 30 or 31, wherein said nucleic acid molecule further comprises a transmembrane segment.

33. The nucleic acid molecule of claim 30 or 31, wherein said nucleic acid molecule is operatively linked to an expression vector to form a recombinant molecule.

34. A recombinant cell comprising a recombinant molecule comprising a nucleic acid molecule operatively linked to an expression vector, said nucleic acid molecule comprising a sequence encoding a Peptide-L-MHC heterodimer comprising;
   (a) an MHC segment of said heterodimer which forms a peptide binding groove, comprising at least a portion of an MHC class II β chain and at least a portion of an MHC class II α chain;
   (b) an antigenic peptide comprising from about 5 to about 40 amino acid residues which binds to said peptide binding groove; and
   (c) a linker comprising an amino acid sequence of at least about 15 amino acid residues, wherein said peptide is covalently linked by said linker to the N-terminus of one of said MHC class II α and β chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;
   wherein said nucleic acid molecule comprises a nucleic acid sequence encoding a signal segment covalently attached to the N-terminus of said antigenic peptide.

35. A recombinant cell comprising a recombinant molecule comprising a nucleic acid molecule operatively linked to an expression vector, said nucleic acid molecule comprising a sequence encoding a Peptide-L-MHC heterodimer comprising:
   (a) an MHC segment of said heterodimer which forms a peptide binding groove, comprising at least a portion of an MHC class I α chain and at least a portion of an MHC class I β2m chain;
   (b) an antigenic peptide comprising from about 8 to about 20 amino acid residues which binds to said peptide binding groove; and (c) a linker comprising an amino acid sequence of at least about 8 amino acid residues, wherein said peptide is covalently linked by said linker to the N-terminus of one of said MHC class I α and β2m chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;
   wherein said nucleic acid molecule comprises a nucleic acid sequence encoding a signal segment covalently attached to the N-terminus of said antigenic peptide.

36. The cell of claim 34 or 35, wherein said cell expresses said Peptide-L-MHC heterodimer.

37. The cell of claim 34 or 35, wherein said cell is selected from the group consisting of a bacterial, fungal, insect and mammalian cells.

38. The cell of claim 34 or 35, wherein said cell is selected from the group consisting of a mammalian cell and an insect cell.

39. The cell of claim 34 or 35, wherein said cell stimulates a T cell response.

40. The cell of claim 34 or 35, wherein said cell does not stimulate a T cell response.

41. The cell of claim 34 or 35, wherein said cell is selected from the group consisting of an antigen presenting cell, a fibroblast, a red blood cell, a pluripotent progenitor cell, epithelial cells and neural cells.

42. The cell of claim 34 or 35, wherein said cell is used to treat a disease that at least in part is caused by abnormal stimulation or suppression of the immune system.

43. A pharmaceutical reagent comprising an isolated Peptide-L-MHC heterodimer comprising:
   (a) an MHC segment of said heterodimer which forms a peptide binding groove, comprising at least a portion of an MHC class II β chain and at least a portion of an MHC class II α chain;
   (b) an antigenic peptide comprising from about 5 to about 40 amino acid residues which binds to said peptide binding groove;
   (c) a linker comprising an amino acid sequence of at least about 15 amino acid residues, wherein said peptide is covalently linked by said linker to the N-terminus of one of said MHC class II α and β chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;
   wherein said antigenic peptide, linker and at least one of said MHC class II α and β chains is encoded by a nucleic acid molecule, said nucleic acid molecule including a nucleic acid sequence encoding a signal segment attached to the N-terminus of said antigenic peptide.

44. A pharmaceutical reagent comprising an isolated Peptide-L-MHC heterodimer comprising:
   (a) an MHC segment of said heterodimer which forms a peptide binding groove, comprising at least a portion of an MHC class I α chain and at least a portion of an MHC class I β2m chain;
   (b) an antigenic peptide comprising from about 8 to about 20 amino acid residues which binds to said peptide binding groove; and
   (c) a linker comprising an amino acid sequence of at least about 8 amino acid residues, wherein said peptide is covalently linked by said linker to the N-terminus of one of said MHC class I α and β2m chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;
   wherein said antigenic peptide, linker and at least one of said MHC class I α and β2m chains is encoded by a nucleic acid molecule, said nucleic acid molecule including a nucleic acid sequence encoding a signal segment attached to the N-terminus of said antigenic peptide.

45. The pharmaceutical reagent of claim 43 or 44, wherein said pharmaceutical reagent further comprises a suitable carrier that presents said Peptide-L-MHC heterodimer to said T cell receptor.

46. The pharmaceutical reagent of claim 45, wherein said carrier comprises artificial or natural lipid-containing membrane.

47. The pharmaceutical reagent of claim 45, wherein said carrier is selected from the group consisting of cellular membranes, liposomes and micelles.

48. The pharmaceutical reagent of claim 45, wherein said carrier comprises a mammalian cell.

49. The pharmaceutical reagent of claim 43 or 44, wherein said Peptide-L-MHC heterodimer is soluble.

50. A method for producing a Peptide-L-MHC$_{\alpha+\beta}$ heterodimer, comprising:
   a) culturing a cell transformed with at least one nucleic acid molecule comprising a sequence encoding a Peptide-L-MHC$_{\alpha+\beta}$ heterodimer, comprising:
      (i) an MHC segment of said heterodimer comprising at least a portion of an MHC class II β chain and at least a portion of an MHC class II α chain which form a peptide binding groove;
      (ii) an antigenic peptide comprising from about 5 to about 40 amino acid residues which binds to said peptide binding groove; and
      (iii) a linker comprising an amino acid sequence of at least about 15 amino acid residues, wherein said peptide is covalently linked by said linker to the N-terminus of one of said MHC class II α and β chains, said linker facilitating the binding of said peptide to said peptide binding groove such that said peptide and said peptide binding groove form a conformation that is recognized by a T cell receptor without substantially hindering interaction between said Peptide-L-MHC$_{\alpha+\beta}$ heterodimer and said T cell receptor;
   wherein said antigenic peptide, linker and at least one of said MHC class II α and β chains is encoded by a nucleic acid molecule, said nucleic acid molecule including a nucleic acid sequence encoding a signal segment attached to the N-terminus of said antigenic peptide;
   said step of culturing being conducted to produce said Peptide-L-MHC$_{\alpha+\beta}$ heterodimer; and
   b) recovering said Peptide-L-MHC$_{\alpha+\beta}$ heterodimer.

51. A method for producing a Peptide-L-MHC$_{\alpha+\beta 2m}$ heterodimer, comprising:
   a) culturing a cell transformed with at least one nucleic acid molecule comprising a sequence encoding a Peptide-L-MHC$_{\alpha+\beta 2m}$ heterodimer, comprising:
      (i) an MHC segment of said heterodimer comprising at least a portion of an MHC class I α chain and at least a portion of an MHC class I β2m chain which form a peptide binding groove;
      (ii) an antigenic peptide comprising from about 8 to about 20 amino acid residues which binds to said peptide binding groove; and
      (iii) a linker comprising an amino acid sequence of at least about 8 amino acid residues, wherein said peptide is covalently linked by said linker to the N-terminus of one of said MHC class I α and β2m chains, said linker facilitating the binding of said peptide to said peptide binding groove such that said peptide and said peptide binding groove form a conformation that is recognized by a T cell receptor without substantially hindering interaction between said Peptide-L-MHC$_{\alpha+\beta 2m}$ heterodimer and said T cell receptor;

wherein said antigenic peptide, linker and at least one of said MHC class I α and β2m chains is encoded by a nucleic acid molecule, said nucleic acid molecule including a nucleic acid sequence encoding a signal segment attached to the N-terminus of said antigenic peptide;

said step of culturing being conducted to produce said Peptide-L-MHC$_{\alpha+\beta 2m}$ heterodimer; and b) recovering said Peptide-L-MHC$_{\alpha+\beta 2m}$ heterodimer.

52. A method for producing a Peptide-L-MHC$_{\alpha+\beta}$ heterodimer anchored to the plasma membrane of a cell comprising:

a) culturing a cell transformed with at least one nucleic acid molecule having a sequence encoding a Peptide-L-MHC$_{\alpha+\beta}$ heterodimer comprising:
(i) an MHC segment of said heterodimer comprising at least a portion of an MHC class II α chain protein having at least a portion of a transmembrane domain and a cytoplasmic domain and at least a portion of an MHC class II β chain having at least a portion of a transmembrane domain and a cytoplasmic domain which form a peptide binding groove;
(ii) an antigenic peptide comprising from about 5 to about 40 amino acid residues which binds to said peptide binding groove; and
(iii) a linker comprising an amino acid sequence of at least about 15 amino acid residues, wherein said peptide is covalently linked by said linker to the N-terminus of one of said MHC class II α and β chains, said linker facilitating the binding of said peptide to said peptide binding groove such that said peptide and said MHC segment form a conformation that is recognized by a T cell receptor without substantially hindering the interaction of said Peptide-L-MHC$_{\alpha+\beta}$ heterodimer and said T cell receptor;

wherein said antigenic peptide, linker and at least one of said MHC class II α and β chains is encoded by a nucleic acid molecule, said nucleic acid molecule including a nucleic acid sequence encoding a signal segment attached to the N-terminus of said antigenic peptide;

said step of culturing being conducted to produce said Peptide-L-MHC$_{\alpha+\beta}$ heterodimer anchored to the plasma membrane of said cell; and b) recovering said cell.

53. A method for producing a Peptide-L-MHC$_{\alpha+\beta 2m}$ heterodimer anchored to the plasma membrane of a cell comprising:

a) culturing a cell transformed with at least one nucleic acid molecule comprising a sequence encoding a Peptide-L-MHC$_{\alpha+\beta 2m}$ heterodimer comprising:
(i) an MHC segment of said heterodimer comprising at least a portion of an MHC class I β2m protein having at least a portion of a transmembrane domain and a cytoplasmic domain and at least a portion of an MHC class I α chain having at least a portion of a transmembrane domain and a cytoplasmic domain which form a peptide binding groove;
(ii) an antigenic peptide comprising from about 8 to about 20 amino acid residues which binds to said peptide binding groove; and
(iii) a linker comprising an amino acid sequence of at least about 8 amino acid residues, wherein said peptide is covalently linked by said linker to the N-terminus of one of said MHC class I α and β2m chains, said linker facilitating the binding of said peptide to said peptide binding groove such that said peptide and said MHC segment form a conformation that is recognized by a T cell receptor without substantially hindering the interaction of said Peptide-L-MHC$_{\alpha+\beta 2m}$ heterodimer and said T cell receptor;

wherein said antigenic peptide, linker and at least one of said MHC class I α and β2m chains is encoded by a nucleic acid molecule, said nucleic acid molecule including a nucleic acid sequence encoding a signal segment attached to the N-terminus of said antigenic peptide;

said step of culturing being conducted to produce said Peptide-L-MHC$_{\alpha+\beta 2m}$ heterodimer anchored to the plasma membrane of said cell; and b) recovering said cell.

54. A method to regulate an immune response comprising administering to an animal an effective amount of an isolated Peptide-L-MHC heterodimer comprising:

a) an MHC segment of said heterodimer which forms a peptide binding groove, comprising at least a portion of an MHC class II β chain and at least a portion of an MHC class II α chain;

b) an antigenic peptide comprising from about 5 to about 40 amino acid residues which binds to said peptide binding groove; and c) a linker comprising an amino acid sequence of at least about 15 amino acid residues, said peptide being covalently linked to the N-terminus of one of said MHC class II α and β chains of said MHC segment by said linker, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;

wherein said antigenic peptide, linker and at least one of said MHC class II α and β chains is encoded by a nucleic acid molecule, said nucleic acid molecule including a nucleic acid sequence encoding a signal segment attached to the N-terminus of said antigenic peptide.

55. A method to regulate an immune response comprising administering to an animal an effective amount of an isolated Peptide-L-MHC heterodimer comprising:

a) an MHC segment of said heterodimer which forms a peptide binding groove, comprising at least a portion of an MHC class I α chain and at least a portion of an MHC class I β2m chain;

b) an antigenic peptide comprising from about 8 to about 20 amino acid residues which binds to said peptide binding groove; and c) a linker comprising an amino acid sequence of at least about 8 amino acid residues, wherein said peptide is covalently linked by said linker to the N-terminus of one of said MHC class I α and β2m chains, said linker facilitating the binding of said peptide to said peptide binding groove such that said peptide and said MHC segment form a conformation that is recognized by a T cell receptor without substantially hindering interaction between said Peptide-L-MHC heterodimer and said T cell receptor;

wherein said antigenic peptide, linker and at least one of said MHC class I α and β2m chains is encoded by a nucleic acid molecule, said nucleic acid molecule including a nucleic acid sequence encoding a signal segment attached to the N-terminus of said antigenic peptide.

56. The method of claim 54 or 55, wherein said immune response is stimulated by said heterodimer.

57. The method of claim 54 or 55, wherein said immune response is suppressed by said heterodimer.

* * * * *